(12) United States Patent
Bosanac et al.

(10) Patent No.: US 10,570,118 B2
(45) Date of Patent: Feb. 25, 2020

(54) ISOQUINOLONES AS BTK INHIBITORS

(71) Applicant: Boehringer Ingelheim International GmbH, Ingelheim am Rhein (DE)

(72) Inventors: Todd Bosanac, New Milford, CT (US); Joerg Bentzien, White Plains, NY (US); Michael Jason Burke, Newtown, CT (US); Darren Todd DiSalvo, New Milford, CT (US); Wang Mao, Milford, CT (US); Fariba Soleymanzadeh, Danbury, CT (US); John A. Westbrook, Woodbridge, CT (US); Zhaoming Xiong, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/069,046

(22) PCT Filed: Jan. 12, 2017

(86) PCT No.: PCT/US2017/013100
§ 371 (c)(1),
(2) Date: Jul. 10, 2018

(87) PCT Pub. No.: WO2017/123695
PCT Pub. Date: Jul. 20, 2017

(65) Prior Publication Data
US 2019/0023686 A1  Jan. 24, 2019

Related U.S. Application Data

(60) Provisional application No. 62/278,085, filed on Jan. 13, 2016.

(51) Int. Cl.
| | | |
|---|---|---|
| *C07D 401/04* | (2006.01) | |
| *C07D 401/10* | (2006.01) | |
| *C07D 401/14* | (2006.01) | |
| *C07D 471/04* | (2006.01) | |
| *C07D 487/04* | (2006.01) | |
| *A61K 31/4725* | (2006.01) | |

(52) U.S. Cl.
CPC .................. *C07D 401/14* (2013.01)

(58) Field of Classification Search
None
See application file for complete search history.

(56) References Cited

U.S. PATENT DOCUMENTS

| | | |
|---|---|---|
| 7,560,571 B2 | 7/2009 | Ronan et al. |
| 8,377,946 B1 | 2/2013 | Chen et al. |
| 8,557,803 B2 | 10/2013 | Yamamoto et al. |
| 9,926,299 B2 | 3/2018 | Han et al. |
| 9,975,882 B2 | 5/2018 | Bosanac et al. |
| 2004/0198986 A1 | 10/2004 | Adams et al. |
| 2008/0045542 A1 | 2/2008 | Ronan et al. |
| 2008/0076921 A1 | 3/2008 | Honigberg et al. |
| 2009/0012309 A1 | 1/2009 | Adams et al. |
| 2011/0003806 A1 | 1/2011 | Hirose et al. |
| 2014/0045813 A1 | 2/2014 | Bentzien et al. |
| 2016/0207906 A1 | 7/2016 | Kawahata et al. |
| 2016/0340339 A1 | 11/2016 | Bentzien et al. |

FOREIGN PATENT DOCUMENTS

| | | |
|---|---|---|
| CA | 2784647 A1 | 7/2011 |
| EP | 2543375 A1 | 1/2013 |
| WO | 199740019 A1 | 10/1997 |
| WO | 2003015776 A1 | 2/2003 |
| WO | 2007117692 A2 | 10/2007 |
| WO | 2008039218 A2 | 4/2008 |
| WO | 2008121742 A2 | 10/2008 |
| WO | 2010012690 A1 | 2/2010 |
| WO | 2010055304 A2 | 5/2010 |
| WO | 2010090716 A1 | 8/2010 |
| WO | 2011082732 A1 | 7/2011 |
| WO | 2011152351 A1 | 12/2011 |
| WO | 2012021615 A1 | 2/2012 |
| WO | 2012156334 A1 | 11/2012 |

(Continued)

OTHER PUBLICATIONS

Hartkamp et al. International Journal of Interferon, Cytokine and Mediator Research 2015:7 27-34. (Year: 2015).*
Seiler et al. Expert Opinion on Investigational Drugs, 2017 vol. 26, No. 8, 909-915 (Year: 2017).*
Abstract in English for WO 2011/082732, publication date Jul. 14, 2011.
Akinleye, A. et al., "Ibrutinib and novel BTK inhibitors in clinical develoopment." Journal of Hematology & Oncology, 2013, 6:59, pp. 1-9.
Chakravarty, S. et al., "Kinase inhibitors: A new tool for the treatment of rheumatoid arthritis." Clinical Immunology, 2013, vol. 148, pp. 66-78.
International Search Report and Written Opinion for PCT/US2013/054096 dated Sep. 30, 2013.

(Continued)

*Primary Examiner* — Emily A Bernhardt
(74) *Attorney, Agent, or Firm* — Atabak R. Royaee

(57) ABSTRACT

The present invention encompasses compounds of the formula (I) wherein the groups R1, R2, R3, R4 and R5 are defined herein, which are suitable for the treatment of diseases related to Bruton's tyrosine kinase (BTK), and processes for making these compounds, pharmaceutical preparations containing these compounds, and their methods of use.

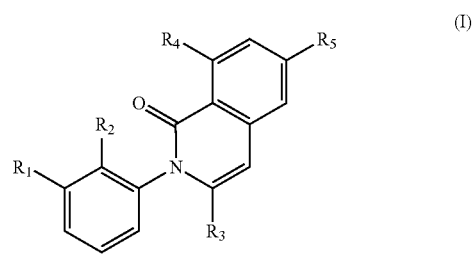

12 Claims, No Drawings

(56) References Cited

FOREIGN PATENT DOCUMENTS

| WO | 2013113097 A1 | 8/2013 |
| WO | 2013157022 A1 | 10/2013 |
| WO | 2014025976 A1 | 2/2014 |
| WO | 2014040965 A1 | 3/2014 |
| WO | 2014068527 A1 | 5/2014 |
| WO | 2014082598 A1 | 6/2014 |
| WO | 2015033888 A1 | 3/2015 |

OTHER PUBLICATIONS

International Search Report and Written Opinion for PCT/US2014/026113, dated Jun. 2, 2014.
International Search Report and Written Opinion for PCT/US2014/026966, dated Jul. 22, 2014.
International Search Report and Written Opinion for PCT/US2015/012590 dated Mar. 25, 2015.
International Search Report for PCT/US2015/012590 dated Mar. 25, 2015.
International Search Report PCT/US2016/066799 dated Jul. 12, 2017. 4 pgs.
International Search Report PCT/US2017/013100 dated Mar. 2, 2017.
Summary of Pfizer Oral Presentation, "Targeted covalent reversible inhibitors for Bruton's Tyrosine Kinase." Presented by Suvit Thaisrivongs on Apr. 16, 2013.
Whang, J. et al., "Bruton's tyrosine kinase inhibitors for the treatment of rheumatoid arthritis." Drug Discovery Today, 2014, pp. 1-5.

* cited by examiner

ISOQUINOLONES AS BTK INHIBITORS

BACKGROUND OF THE INVENTION

1. Technical Field

The present invention relates to novel compounds which inhibit BTK and their use as medicaments.

2. Background Information

Members of the protein kinase family of human enzymes play important regulatory roles in a multitude of distinct signal transduction processes due to their post-translational modification of specific proteins via the addition of a phosphate group (Hunter, Cell 1987, 50, 823-829). Bruton's tyrosine kinase (BTK) is a member of the Tec family of tyrosine kinases and plays a critical role in B cell development, activation and antibody production.

The contribution of BTK to B cell biology is exemplified in the X-linked agammaglobulinemia (XLA) immunodeficiency in humans (reviewed in Lindvall, Immunol. Rev. 2005, 203, 200-215) that display attenuated calcium signaling upon B cell receptor (BCR) engagement, lack mature B cells in the periphery due to block between pro- and pre-B cell stage and have lower levels of circulating antibodies than normal healthy subjects. The outcome of recent clinical trials with B cell depleting anti-CD20 molecules in diseases such as rheumatoid arthritis (RA) and multiple sclerosis (MS) support the hypothesis that B cells offer an important intervention node for controlling autoimmune disorders (Townsend, Immunol. Rev. 2010, 237, 264-283). As such, attenuation of B cell activation and proliferation via inhibition of BTK may offer similar therapeutic benefit and is consistent with the demonstrated resistance of BTK-deficient mice to collagen induced arthritis (Jansson, Clin. Exp. Immunol. 1993, 94, 459-465) and experimental autoimmune encephalitis (Svensson, Eur. J. Immunol. 2002, 32, 1939-1946 and Mangla, Blood 2004, 104, 1191-1197). Similarly, the clinical efficacy observed with a neutralizing antibody to the B cell stimulating factor BlyS supports a role for B cells in the pathophysiology of systemic lupus erythematosus (SLE) (La Cava, Expert Opin. Biol. Ther. 2010, 10, 1555-1561). Given the necessity for BTK for the production of autoantibodies, including anti-DNA antibodies, in murine models of SLE (Steinberg, J. Clin. Invest. 1982, 70, 587-597; Golding, J. Immunol. 1983, 130, 1043-1046; Scribner, J. Immunol. 1987, 138, 3611-3617; Seldin, J. Exp. Med. 1987, 166, 1585-1590; Takeshita, Int. Immunol. 1998, 10, 435-4444; Whyburn, J. Immunol. 2003, 171, 1850-1858), BTK inhibitors may offer therapeutic benefit to SLE patients.

Within myeloid cells, BTK signal transduction is necessary for the stimulated release of inflammatory cytokines such as TNFα from stimulated monocytes (Horwood, J. Exp. Med. 2003, 197, 1603-1611) and for optimal actin cytoskeletal organization and lacunar bone resorption in isolated osteoclasts (Danks, J. Bone Miner. Res. 2010, 26, 182-192). Bone marrow derived mast cells lacking BTK exhibit impaired activation-induced degranulation and cytokine release. Given the role of BTK in signal transduction processes across multiple cell types implicated in the pathogenesis of autoimmune and allergic disorders, inhibition of BTK activity may provide clinical benefit in diseases such as RA, MS, SLE, lupus nephritis, Sjogren's disease, vasculitis, asthma and allergic disorders.

Currently, various BTK inhibitors are known in the art. However, there still remains a need for additional novel compounds that are highly selective for BTK inhibition.

SUMMARY OF THE INVENTION

The invention comprises a novel class of isoquinolone compounds and methods for making and using the same. These compounds are useful for the treatment of autoimmune and allergic disorders in that they exhibit good inhibitory effect upon BTK.

In a first generic embodiment, there is provided a compound of the formula (I)

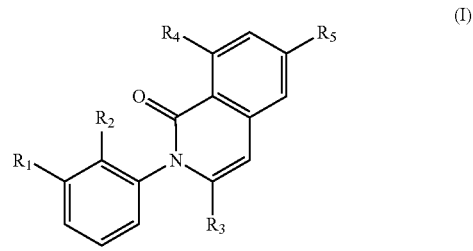

wherein $R_1$ is chosen from

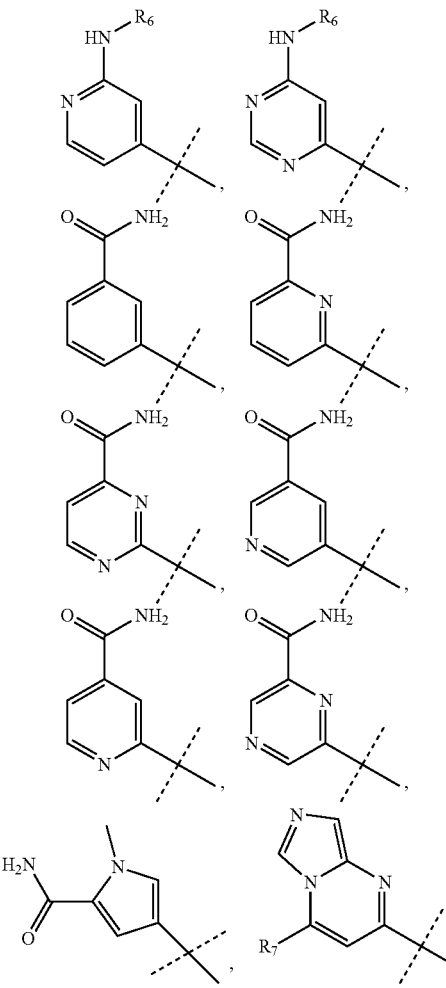

3
-continued

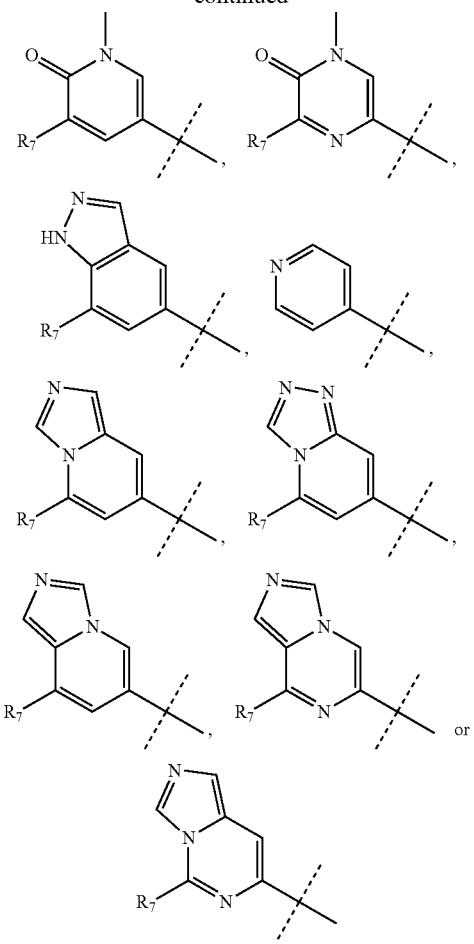

wherein $R_6$ is H or $CH_3$ and;

$R_7$ is H, $NH_2$, —NH—$C_{1-4}$ alkyl or —NH—$C_{3-4}$ cycloalkyl, or —NH-Heterocycle $R_2$ is chosen from H, F, Cl, $CH_3$, or $CH_2OH$;

$R_3$ is chosen from;

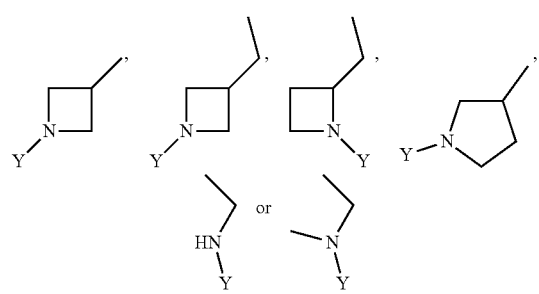

wherein Y is CN,

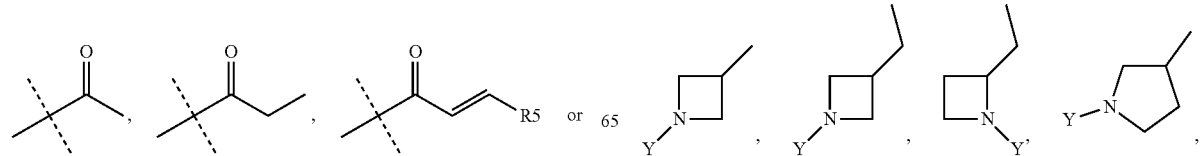

4
-continued

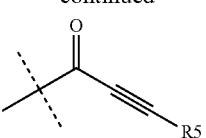

$R_4$ is chosen from H, F, Cl or OMe each $R_5$ is independently chosen from H, $C_{1-4}$ alkyl, or $C_{3-4}$ cycloalkyl;

each group defined above for $R_1$-$R_5$ is, where possible, partially or fully halogentated; or a pharmaceutically acceptable salt or hydrate thereof.

In a further embodiment, there is provided a compound of the formula (I) according to the embodiment herein-above and in which:

$R_1$ is chosen from

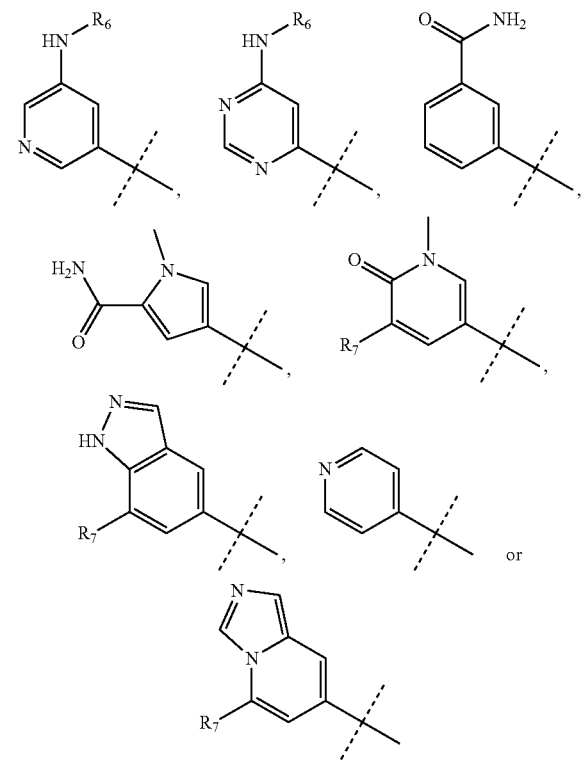

wherein $R_6$ is H or $CH_3$ and;

$R_7$ is H, $NH_2$, —NH—$C_{1-4}$ alkyl or —NH—$C_{3-4}$ cycloalkyl, or —NH-Heterocycle $R_2$ is chosen from H, F, Cl, $CH_3$, or $CH_2OH$;

$R_3$ is chosen from;

-continued

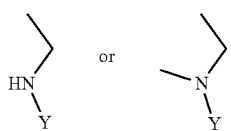

wherein Y is CN,

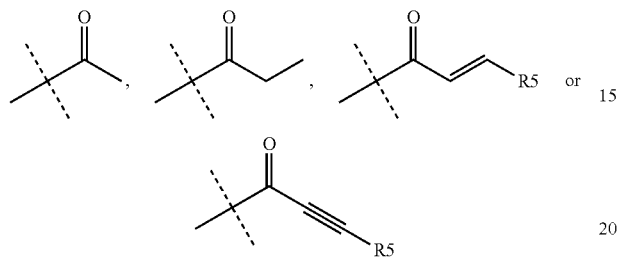

R₄ is chosen from H, F, Cl or OMe each R₅ is independently chosen from H, $C_{1-4}$ alkyl, or $C_{3-4}$ cycloalkyl;

each group defined above for R₁-R₅ is, where possible, partially or fully halogentated; or a pharmaceutically acceptable salt or hydrate thereof.

In a further embodiment, there is provided a compound of the formula (I) according to the embodiment herein-above and in which:

R₁ is chosen from

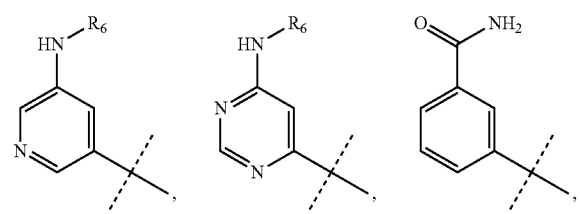

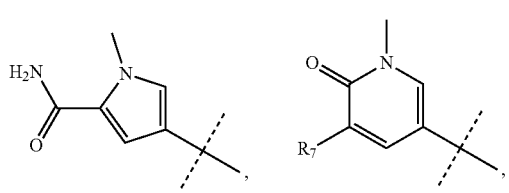

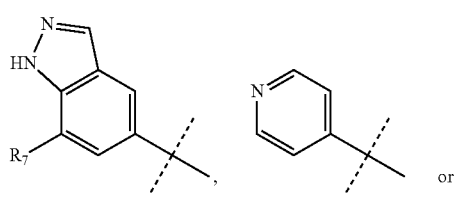

-continued

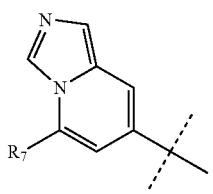

wherein R₆ is H or CH₃ and;

R₇ is H or NH₂

R₂ is chosen from H, F, Cl, CH₃ or CH₂OH;

R₃ is chosen from;

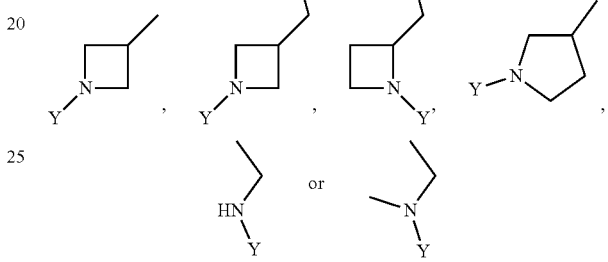

wherein Y is CN,

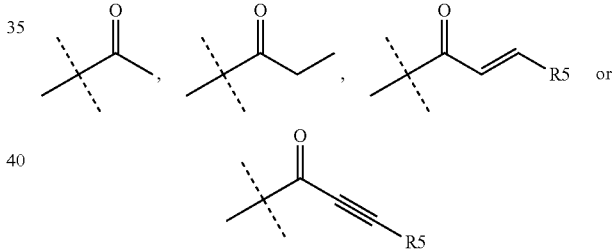

R₄ is chosen from H, F, Cl or OMe each R₅ is independently chosen from H, $C_{1-4}$ alkyl, or $C_{3-4}$ cycloalkyl;

each group defined above for R₁-R₅ is, where possible, partially or fully halogentated; or a pharmaceutically acceptable salt or hydrate thereof.

In a further embodiment, there is provided a compound of the formula (I) according to the embodiment herein-above and in which:

R₁ is chosen from

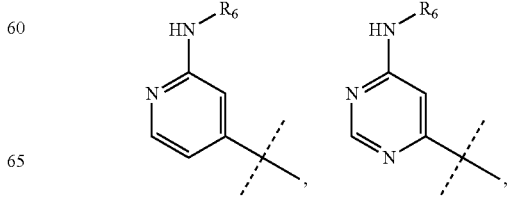

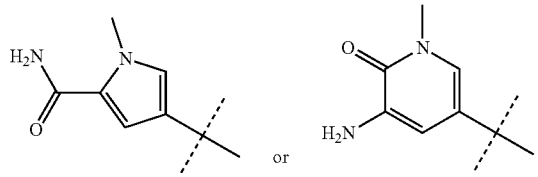

or wherein R_6 is H or CH_3 and;

R_2 is CH_2OH;

R_3 is chosen from;

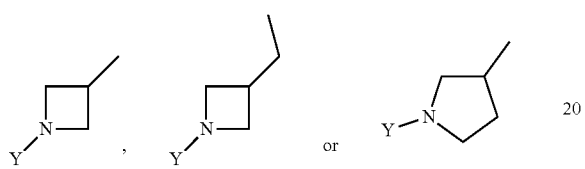

wherein Y is

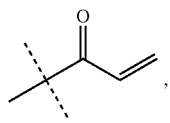

R_4 is chosen from H or F each $R_5$ is independently chosen from H, $C_{1-4}$ alkyl, or $C_{3-4}$ cycloalkyl;

each group defined above for $R_1$-$R_5$ is, where possible, partially or fully halogentated; or a pharmaceutically acceptable salt or hydrate thereof.

In a further embodiment, there is provided a compound of the formula (I) according to the embodiment herein-above, such as that shown in the following Table, which are made in view of the general schemes, examples and methods described herein.

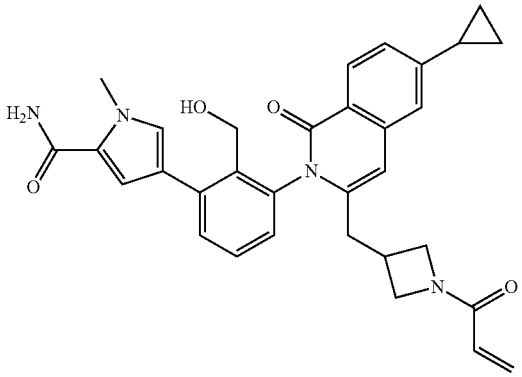 [SMILES: C=CC(=O)N1CC(Cc2cc3cc(C4CC4)ccc3c(=O)n2-c2cccc(-c3cc(C(N)=O)n(C)c3)c2CO)C1]

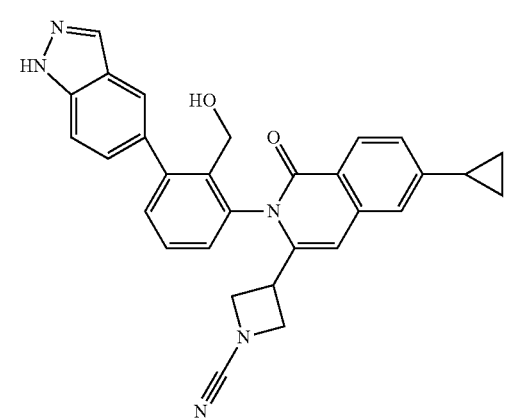 [SMILES: N#CN1CC(c2cc3cc(C4CC4)ccc3c(=O)n2-c2cccc(-c3ccc4[nH]ncc4c3)c2CO)C1]

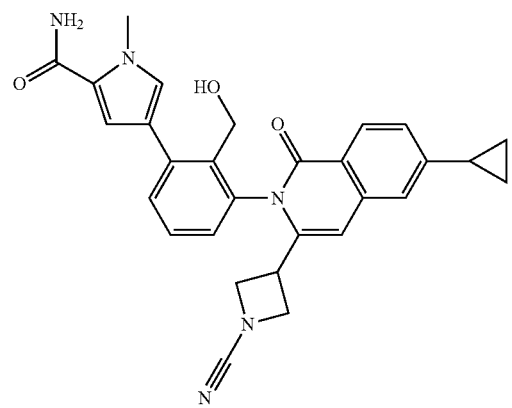

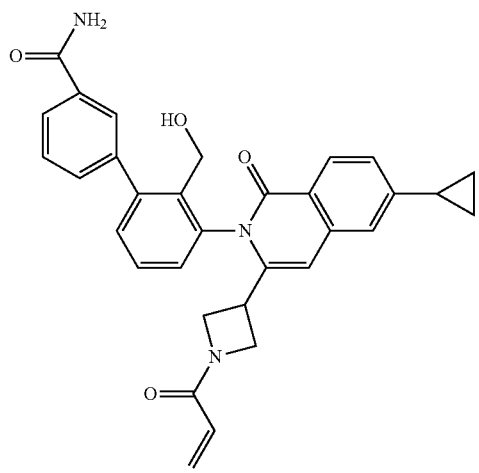 [SMILES: C=CC(=O)N1CC(c2cc3cc(C4CC4)ccc3c(=O)n2-c2cccc(-c3cccc(C(N)=O)c3)c2CO)C1]

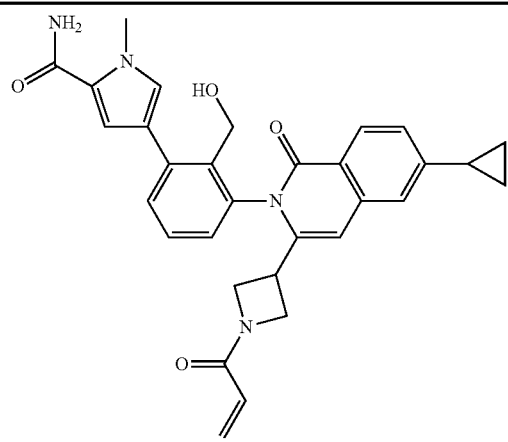
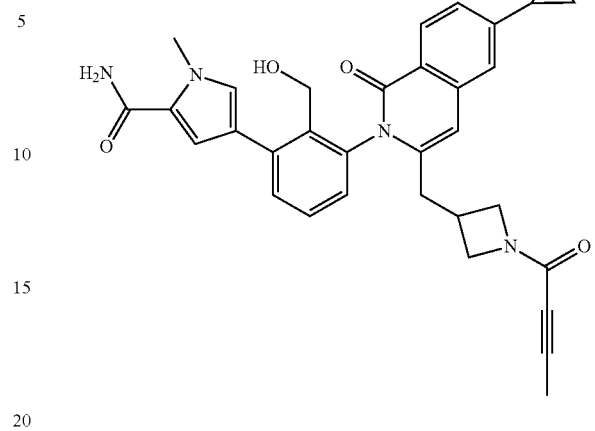
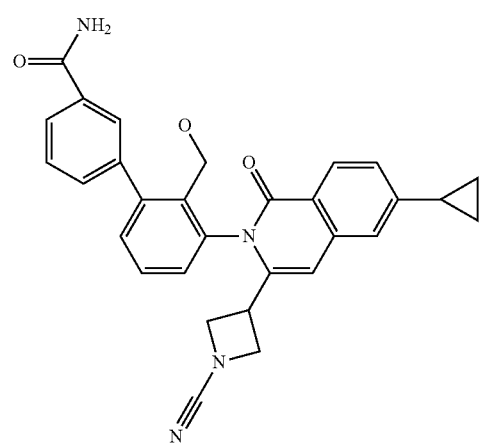 [SMILES: N#CN1CC(c2cc3cc(C4CC4)ccc3c(=O)n2-c2cccc(-c3cccc(C(N)=O)c3)c2CO)C1]
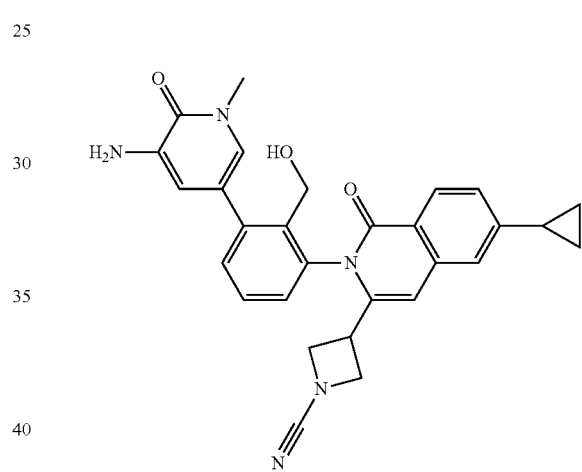
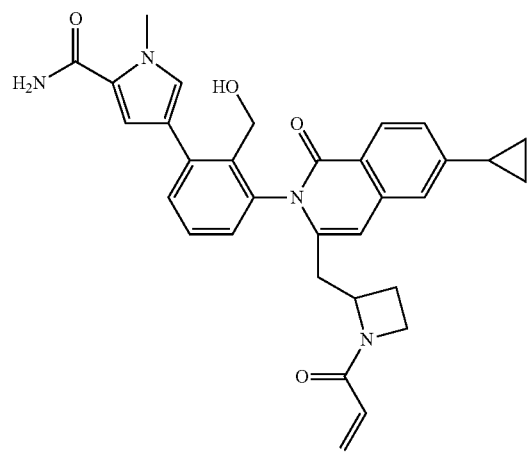 [SMILES: C=CC(=O)N1CCC1Cc1cc2cc(C3CC3)ccc2c(=O)n1-c1cccc(-c2cc(C(N)=O)n(C)c2)c1CO]
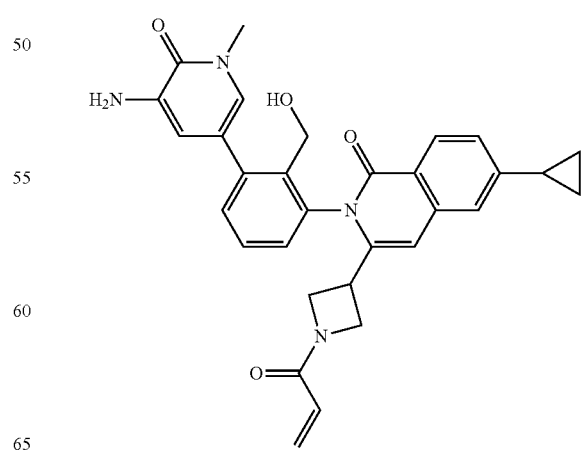

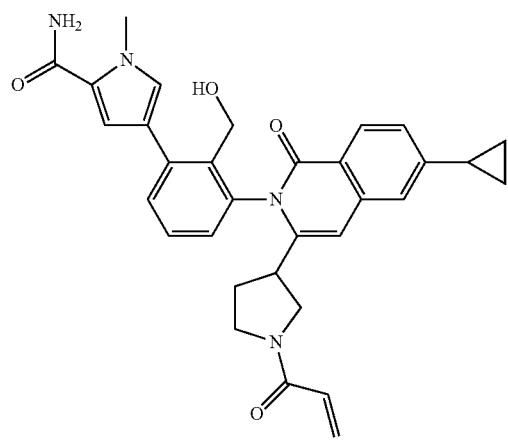 [SMILES: C=CC(=O)N1CCC(c2cc3cc(C4CC4)ccc3c(=O)n2-c2cccc(-c3cc(C(N)=O)n(C)c3)c2CO)C1]
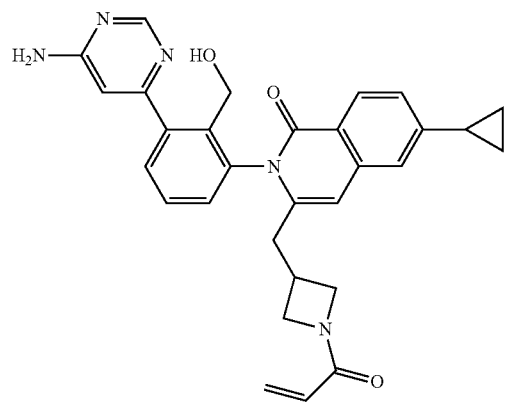
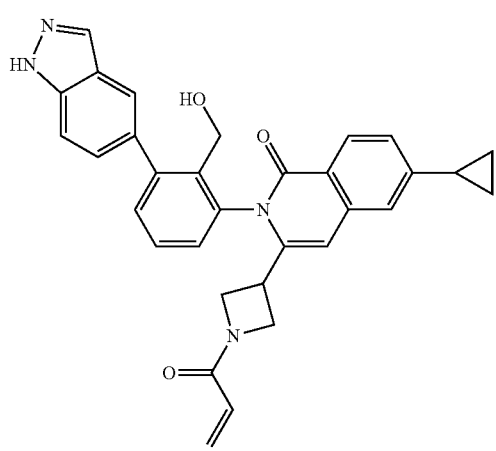 [SMILES: C=CC(=O)N1CC(c2cc3cc(C4CC4)ccc3c(=O)n2-c2cccc(-c3ccc4[nH]ncc4c3)c2CO)C1]
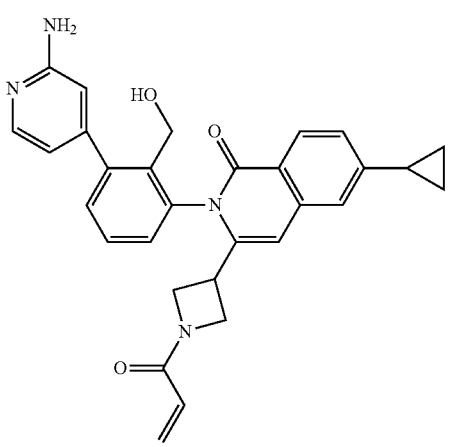
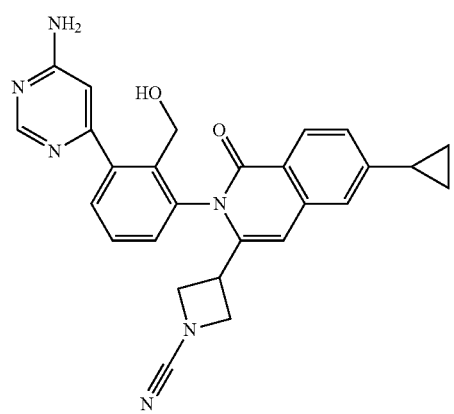 [SMILES: N#CN1CC(c2cc3cc(C4CC4)ccc3c(=O)n2-c2cccc(-c3cc(N)ncn3)c2CO)C1]

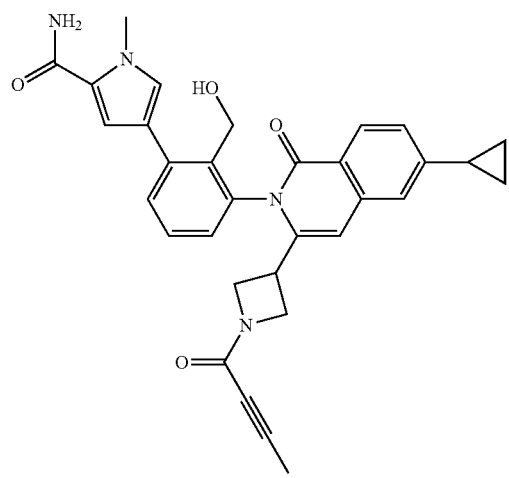 [SMILES: CC#CC(=O)N1CC(c2cc3cc(C4CC4)ccc3c(=O)n2-c2cccc(-c3cc(C(N)=O)n(C)c3)c2CO)C1]
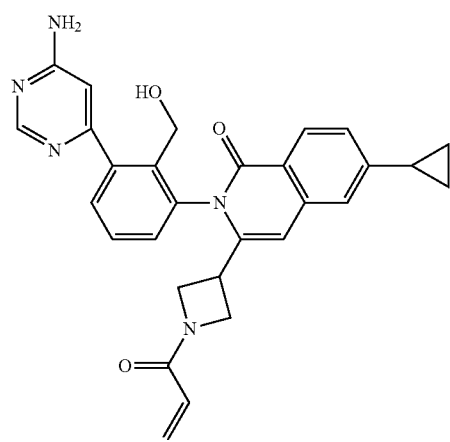
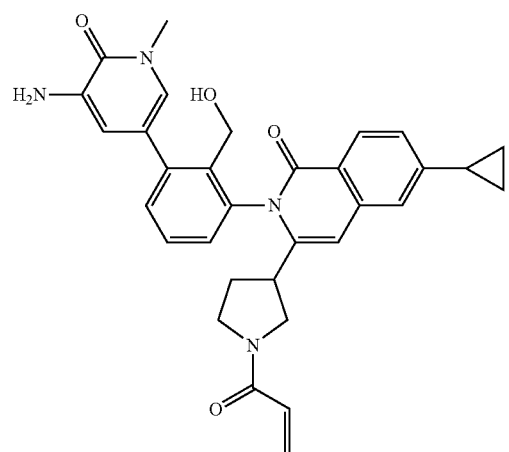 [SMILES: C=CC(=O)N1CCC(c2cc3cc(C4CC4)ccc3c(=O)n2-c2cccc(-c3cc(N)c(=O)n(C)c3)c2CO)C1]
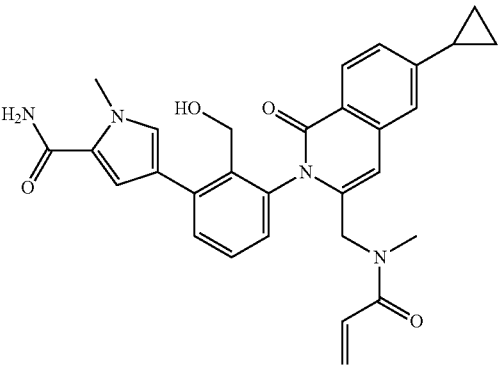 [SMILES: C=CC(=O)N(C)Cc1cc2cc(C3CC3)ccc2c(=O)n1-c1cccc(-c2cc(C(N)=O)n(C)c2)c1CO]
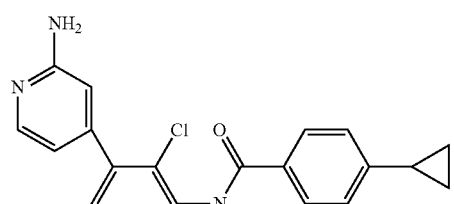
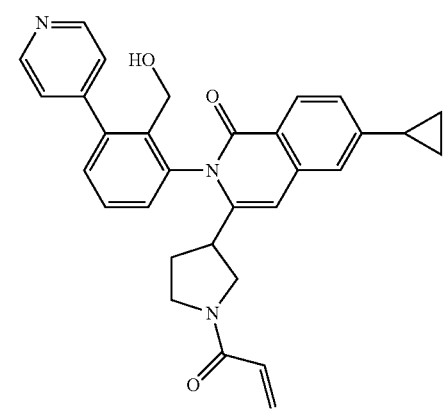 [SMILES: C=CC(=O)N1CCC(c2cc3cc(C4CC4)ccc3c(=O)n2-c2cccc(-c3ccncc3)c2CO)C1]
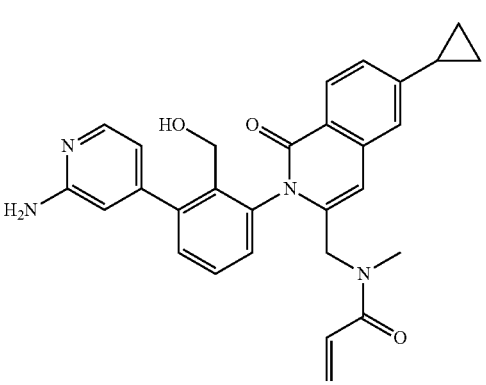 [SMILES: C=CC(=O)N(C)Cc1cc2cc(C3CC3)ccc2c(=O)n1-c1cccc(-c2ccnc(N)c2)c1CO]

15
-continued
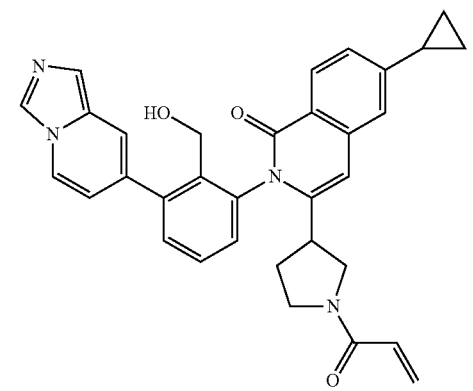 [SMILES: C=CC(=O)N1CCC(c2cc3cc(C4CC4)ccc3c(=O)n2-c2cccc(-c3ccn4cncc4c3)c2CO)C1]
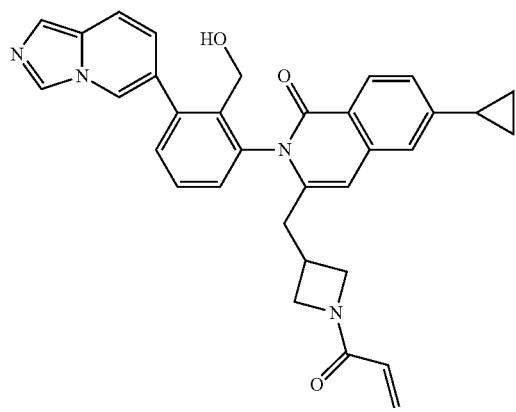 [SMILES: C=CC(=O)N1CC(Cc2cc3cc(C4CC4)ccc3c(=O)n2-c2cccc(-c3ccc4cncn4c3)c2CO)C1]
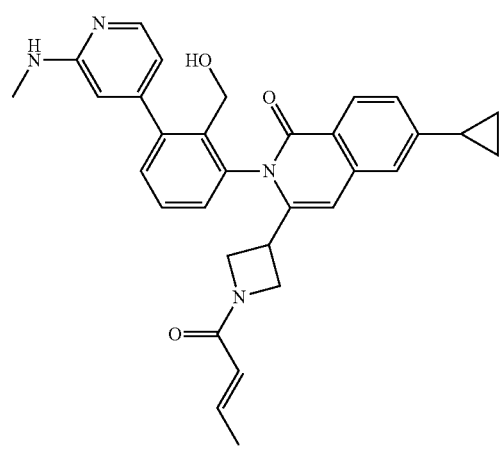 [SMILES: C/C=C/C(=O)N1CC(c2cc3cc(C4CC4)ccc3c(=O)n2-c2cccc(-c3ccnc(NC)c3)c2CO)C1]
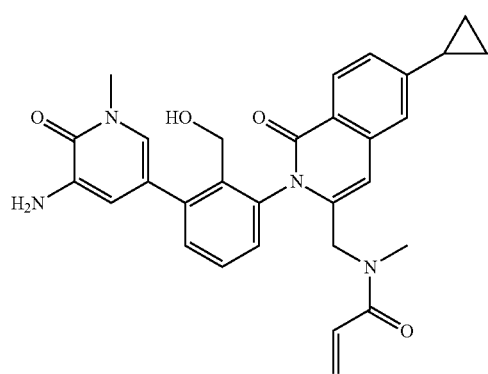 [SMILES: C=CC(=O)N(C)Cc1cc2cc(C3CC3)ccc2c(=O)n1-c1cccc(-c2cc(N)c(=O)n(C)c2)c1CO]
16
-continued
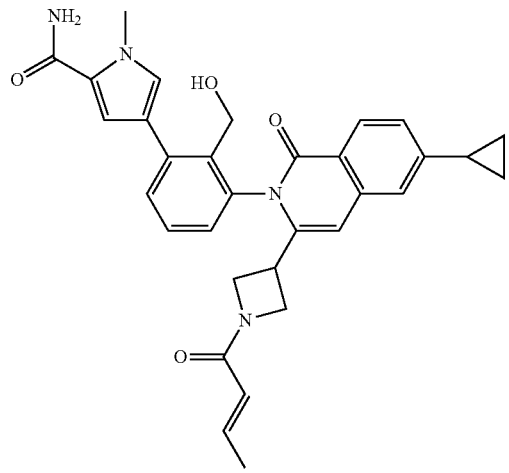 [SMILES: C/C=C/C(=O)N1CC(c2cc3cc(C4CC4)ccc3c(=O)n2-c2cccc(-c3cc(C(N)=O)n(C)c3)c2CO)C1]
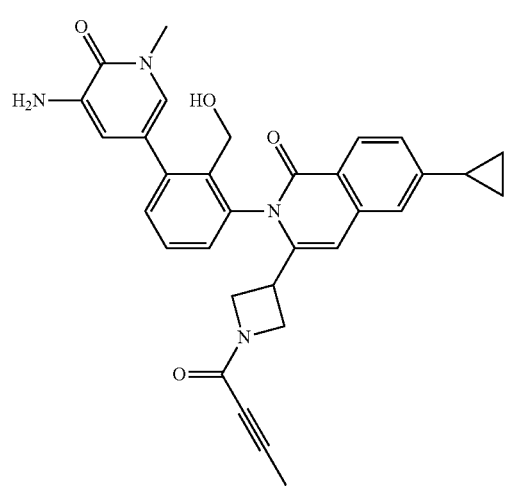 [SMILES: CC#CC(=O)N1CC(c2cc3cc(C4CC4)ccc3c(=O)n2-c2cccc(-c3cc(N)c(=O)n(C)c3)c2CO)C1]
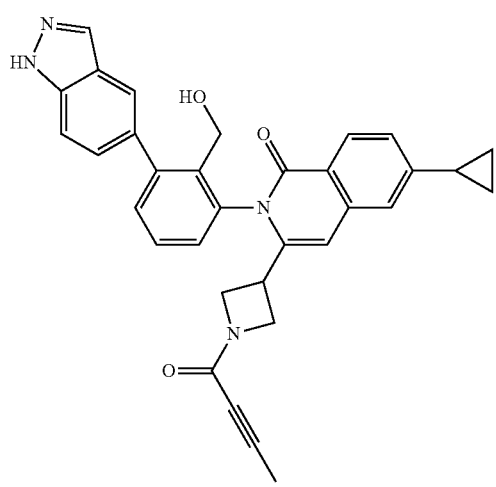 [SMILES: CC#CC(=O)N1CC(c2cc3cc(C4CC4)ccc3c(=O)n2-c2cccc(-c3ccc4[nH]ncc4c3)c2CO)C1]

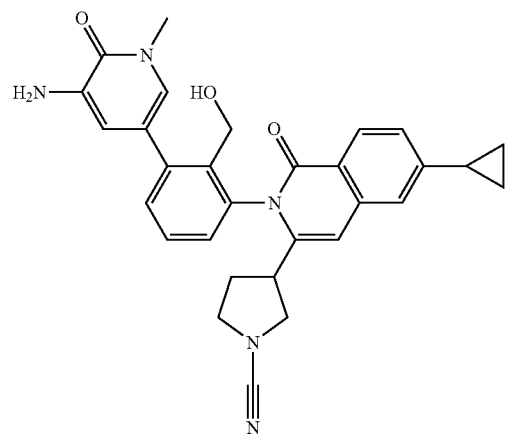 [SMILES: Cn1cc(-c2cccc(-n3c(C4CCN(C#N)C4)cc4cc(C5CC5)ccc4c3=O)c2CO)cc(N)c1=O]
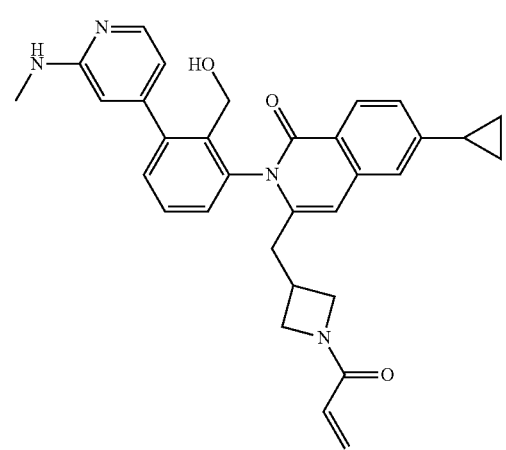 [SMILES: C=CC(=O)N1CC(Cc2cc3cc(C4CC4)ccc3c(=O)n2-c2cccc(-c3ccnc(NC)c3)c2CO)C1]
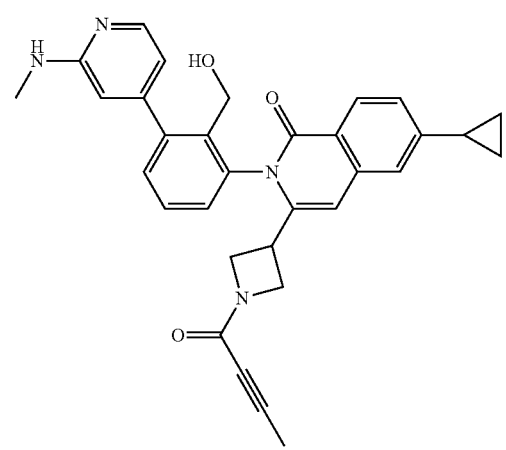 [SMILES: CC#CC(=O)N1CC(c2cc3cc(C4CC4)ccc3c(=O)n2-c2cccc(-c3ccnc(NC)c3)c2CO)C1]
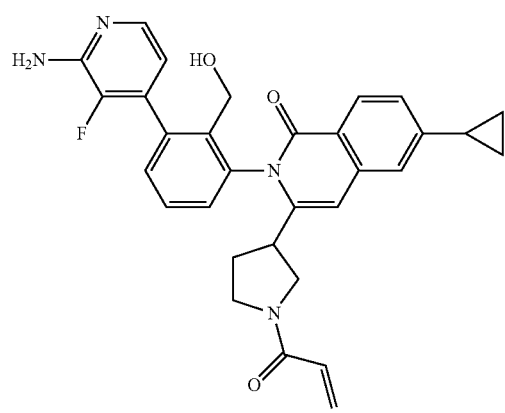 [SMILES: C=CC(=O)N1CCC(c2cc3cc(C4CC4)ccc3c(=O)n2-c2cccc(-c3ccnc(N)c3F)c2CO)C1]
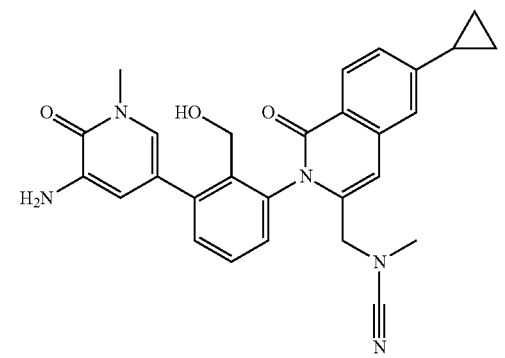 [SMILES: CN(C#N)Cc1cc2cc(C3CC3)ccc2c(=O)n1-c1cccc(-c2cc(N)c(=O)n(C)c2)c1CO]
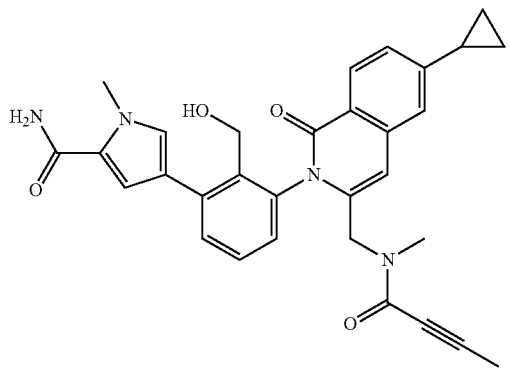 [SMILES: CC#CC(=O)N(C)Cc1cc2cc(C3CC3)ccc2c(=O)n1-c1cccc(-c2cc(C(N)=O)n(C)c2)c1CO]

19
-continued

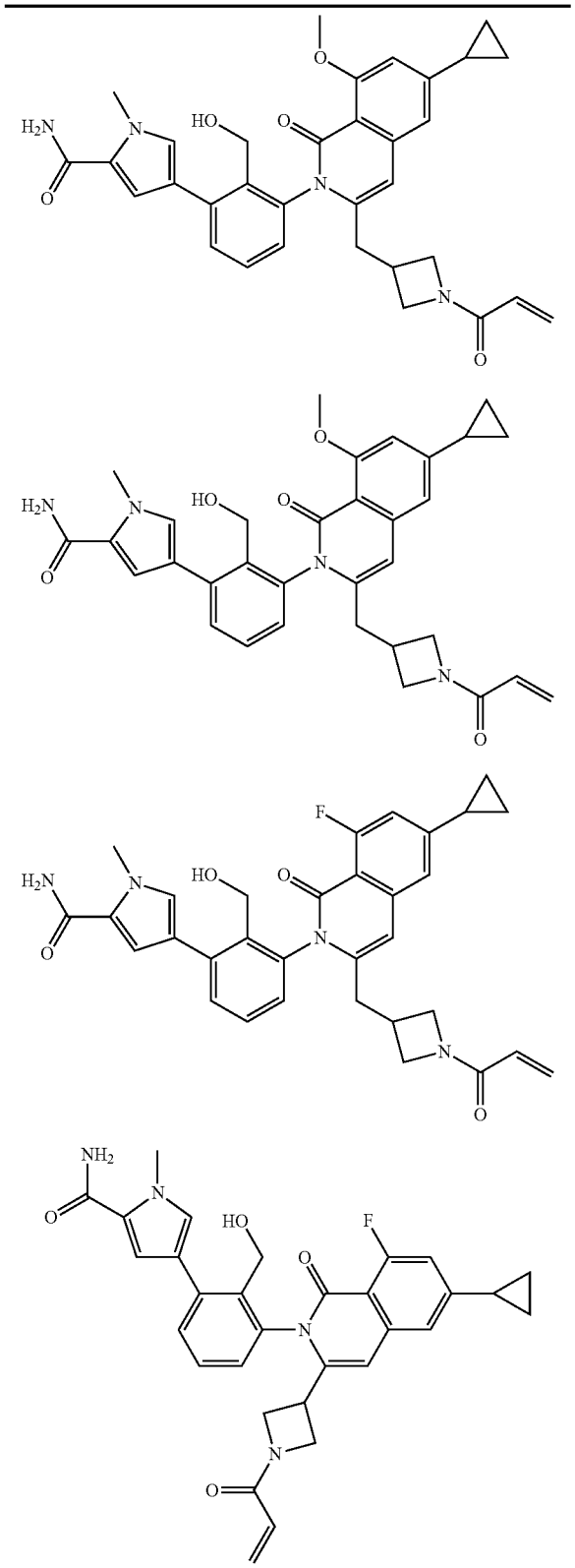

or the pharmaceutically acceptable salts thereof.

In a second generic embodiment, there is provided a pharmaceutical composition comprising a therapeutically effective amount of a compound according to the first generic embodiment or any of its related embodiments or a pharmaceutically acceptable salt or hydrate thereof.

In a third generic embodiment, there is provided a method of treating a disease chosen from rheumatoid arthritis, systemic lupus erythromatosis, lupus nephritis, Sjogren's disease, vasculitis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis or uveitis in a patient, comprising administering to the patient a therapeutically effective amount of a compound according to the first generic embodiment or any of its related embodiments or a pharmaceutically acceptable salt or hydrate thereof.

DETAILED DESCRIPTION OF THE INVENTION

In a first generic embodiment, there is provided a compound of the formula (I)

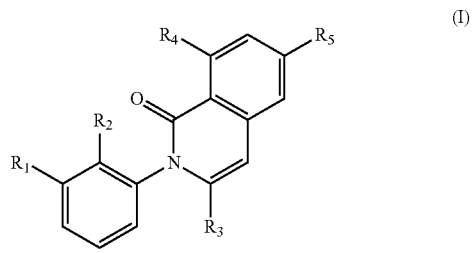

wherein $R_1$ is chosen from

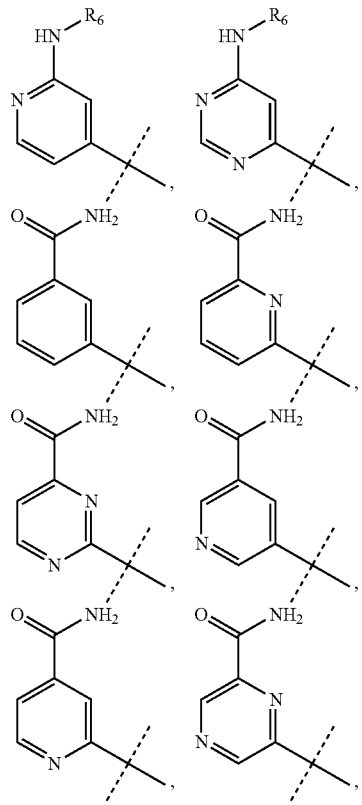

-continued

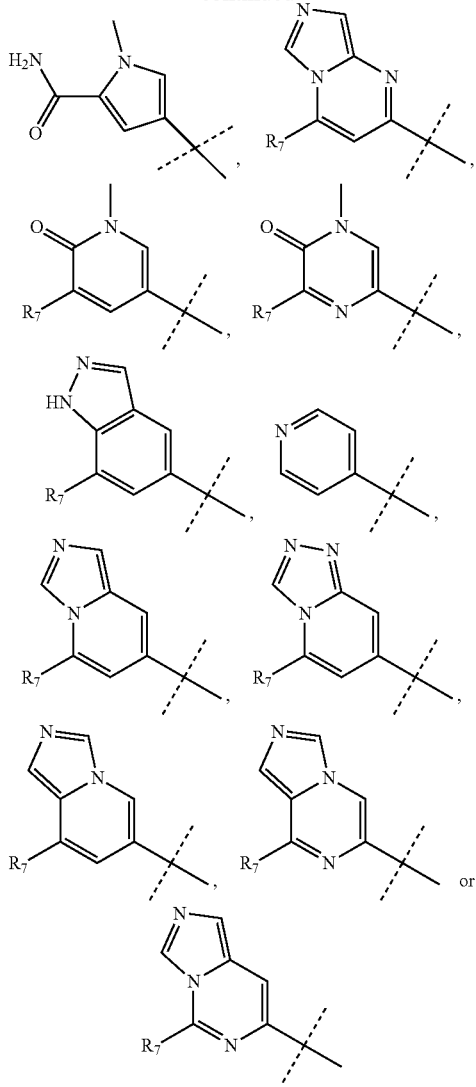

wherein R$_6$ is H or CH$_3$ and;
R$_7$ is H, NH$_2$, —NH—C$_{1-4}$ alkyl or —NH—C$_{3-4}$ cycloalkyl, or —NH-Heterocycle
R$_2$ is chosen from H, F, Cl, CH$_3$, or CH$_2$OH;
R$_3$ is chosen from;

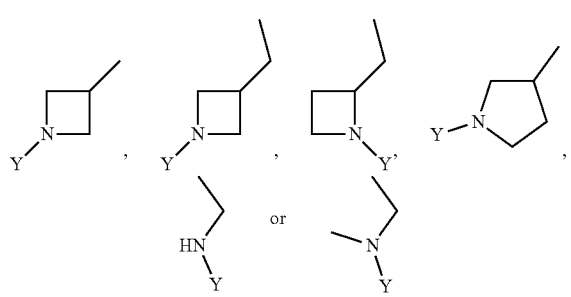

wherein Y is CN,

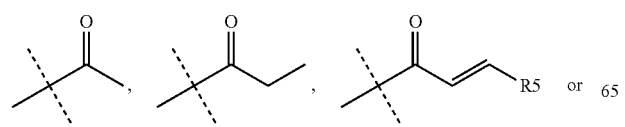

-continued

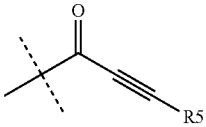

R$_4$ is chosen from H, F, Cl or OMe
each R$_5$ is independently chosen from H, C$_{1-4}$ alkyl, or C$_{3-4}$ cycloalkyl;
each group defined above for R$_1$-R$_5$ is, where possible, partially or fully halogentated; or a pharmaceutically acceptable salt or hydrate thereof.

In a further embodiment, there is provided a compound of the formula (I) according to the embodiment herein-above and in which:
R$_1$ is chosen from

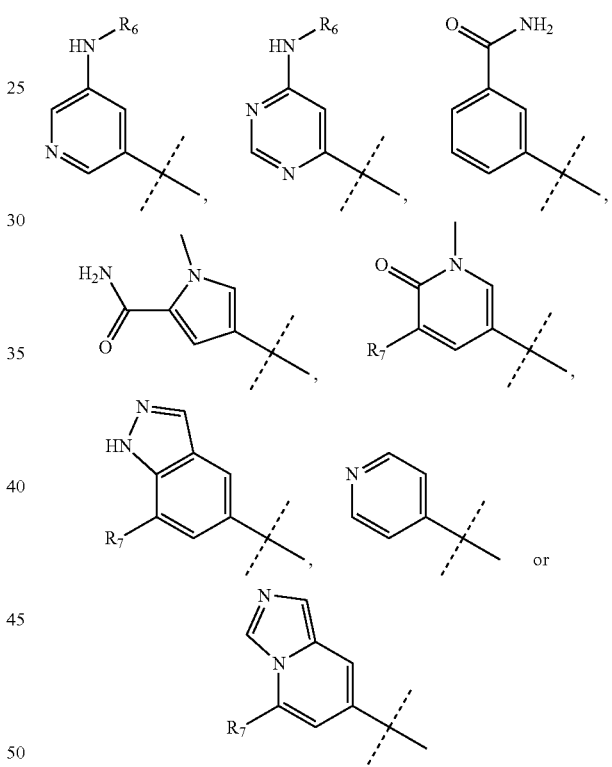

wherein R$_6$ is H or CH$_3$ and;
R$_7$ is H, NH$_2$, —NH—C$_{1-4}$ alkyl or —NH—C$_{3-4}$ cycloalkyl, or —NH-Heterocycle
R$_2$ is chosen from H, F, Cl, CH$_3$, or CH$_2$OH;
R$_3$ is chosen from;

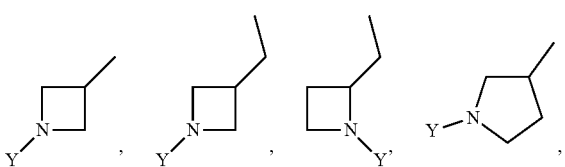

23
-continued

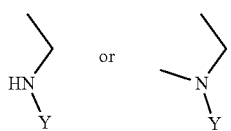

wherein Y is CN,

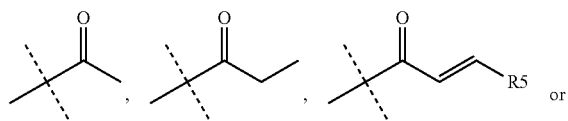

24
-continued

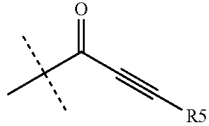

$R_4$ is chosen from H, F, Cl or OMe each $R_5$ is independently chosen from H, $C_{1-4}$ alkyl, or $C_{3-4}$ cycloalkyl;

each group defined above for $R_1$-$R_5$ is, where possible, partially or fully halogentated; or a pharmaceutically acceptable salt or hydrate thereof.

The invention provides made compounds in Table I which are made in view of the general schemes, examples and methods described herein.

Table of compounds and Biological activity

| Example | Structure | BTK IC$_{50}$ (nM) | HPLC Method | RT (min) | m/z |
|---|---|---|---|---|---|
| 1 | 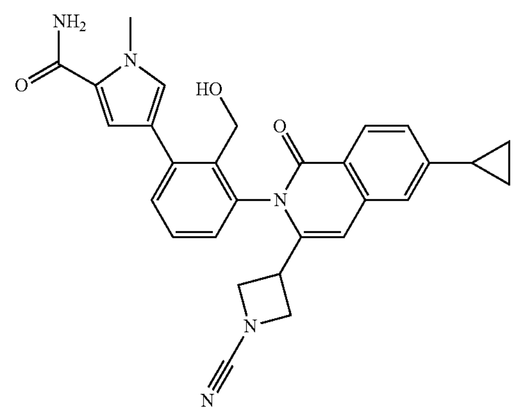 [SMILES: Cn1cc(-c2cccc(-n3c(C4CN(C#N)C4)cc4cc(C5CC5)ccc4c3=O)c2CO)cc1C(N)=O] | 0.7 | A | 1.91 | 492.2 (M − H) |
| 2 | 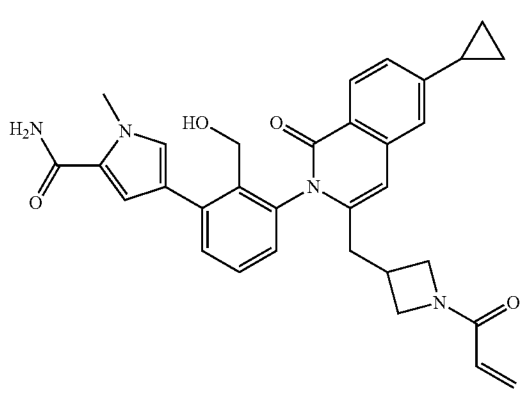 [SMILES: C=CC(=O)N1CC(Cc2cc3cc(C4CC4)ccc3c(=O)n2-c2cccc(-c3cc(C(N)=O)n(C)c3)c2CO)C1] | 4.0 | B | 0.8 | 537.3 (M + H) |

-continued

Table of compounds and Biological activity

| Example | Structure | BTK IC$_{50}$ (nM) | HPLC Method | RT (min) | m/z |
|---------|-----------|--------------------|-------------|----------|-----|
| 3 | 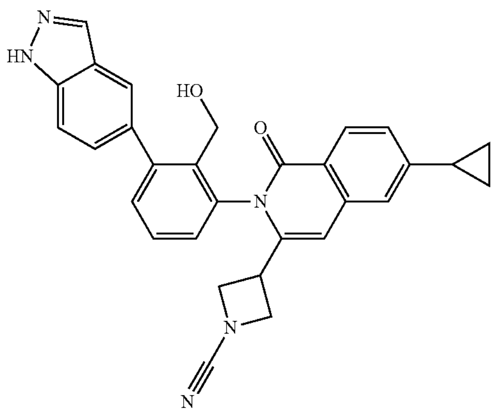 [SMILES: N#CN1CC(c2cc3cc(C4CC4)ccc3c(=O)n2-c2cccc(-c3ccc4[nH]ncc4c3)c2CO)C1] | 1.9 | A | 2.1 | 486.0 (M − H) |
| 4 | 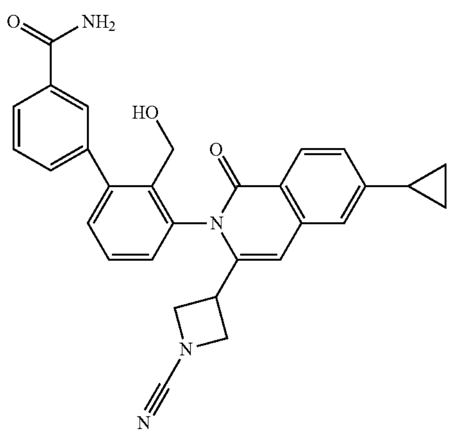 [SMILES: N#CN1CC(c2cc3cc(C4CC4)ccc3c(=O)n2-c2cccc(-c3cccc(C(N)=O)c3)c2CO)C1] | 5.0 | A | 1.89 | 489.3 (M − H) |
| 5 | 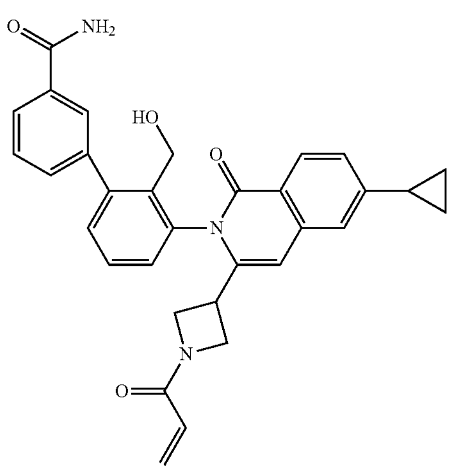 [SMILES: C=CC(=O)N1CC(c2cc3cc(C4CC4)ccc3c(=O)n2-c2cccc(-c3cccc(C(N)=O)c3)c2CO)C1] | 5.2 | A | 1.66 | 518.3 (M − H) |

-continued

Table of compounds and Biological activity

| Example | Structure | BTK IC$_{50}$ (nM) | HPLC Method | RT (min) | m/z |
|---|---|---|---|---|---|
| 6 | 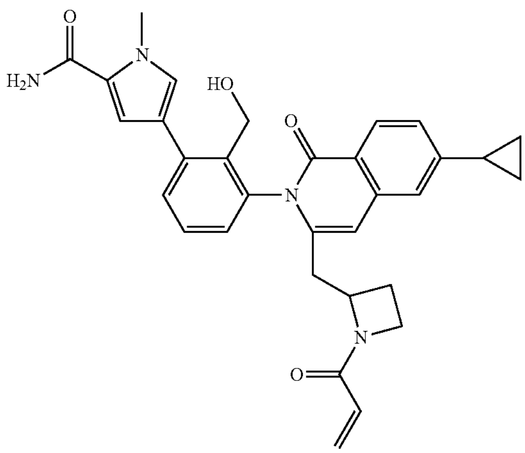 [SMILES: C=CC(=O)N1CCC1Cc1cc2cc(C3CC3)ccc2c(=O)n1-c1cccc(-c2cc(C(N)=O)n(C)c2)c1CO] | 3.9 | A | 1.82 | 535.2 (M − H) |
| 7 | 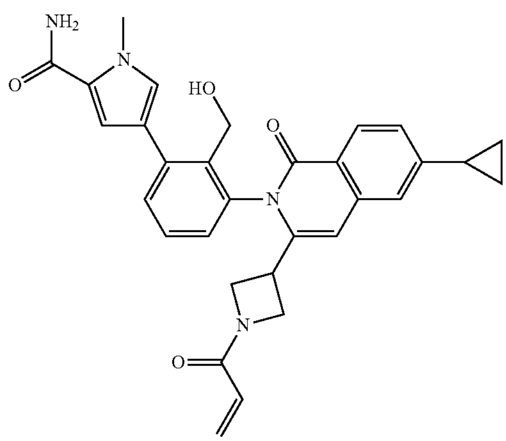 [SMILES: C=CC(=O)N1CC(c2cc3cc(C4CC4)ccc3c(=O)n2-c2cccc(-c3cc(C(N)=O)n(C)c3)c2CO)C1] | 0.7 | A | 1.54 | 523.3 (M + H) |
| 8 | 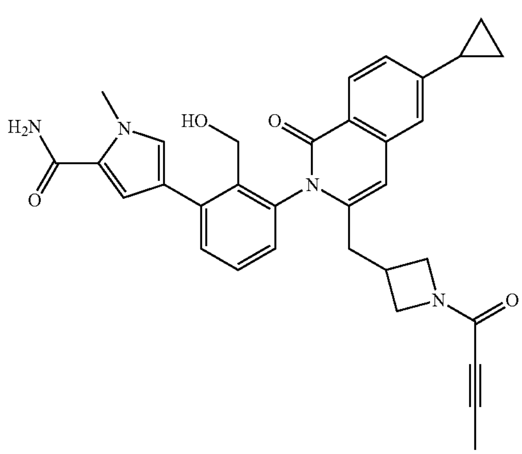 [SMILES: CC#CC(=O)N1CC(Cc2cc3cc(C4CC4)ccc3c(=O)n2-c2cccc(-c3cc(C(N)=O)n(C)c3)c2CO)C1] | 11 | B | 0.84 | 549.3 (M + H) |

-continued

Table of compounds and Biological activity

| Example | Structure | BTK IC$_{50}$ (nM) | HPLC Method | RT (min) | m/z |
|---|---|---|---|---|---|
| 9 | 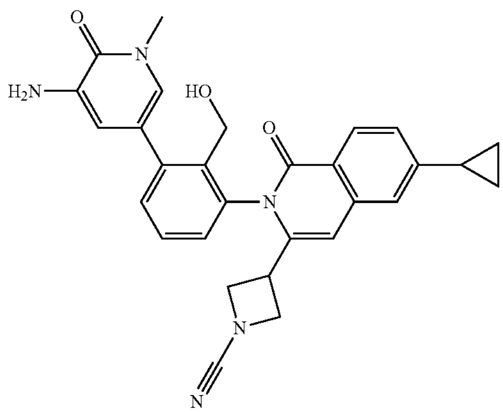 [SMILES: Cn1cc(-c2cccc(-n3c(C4CN(C#N)C4)cc4cc(C5CC5)ccc4c3=O)c2CO)cc(N)c1=O] | 2.6 | A | 1.74 | 492.2 (M − H) |
| 10 | 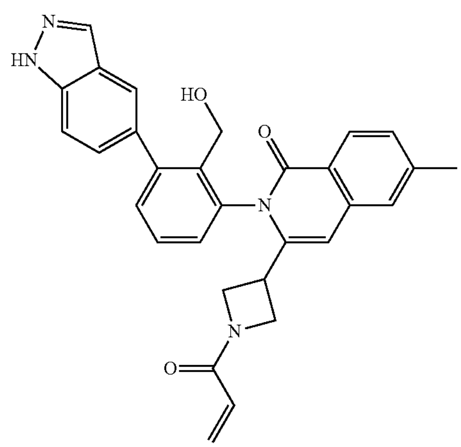 [SMILES: C=CC(=O)N1CC(c2cc3cc(C)ccc3c(=O)n2-c2cccc(-c3ccc4[nH]ncc4c3)c2CO)C1] | 3.1 | A | 1.84 | 515.2 (M − H) |
| 11 | 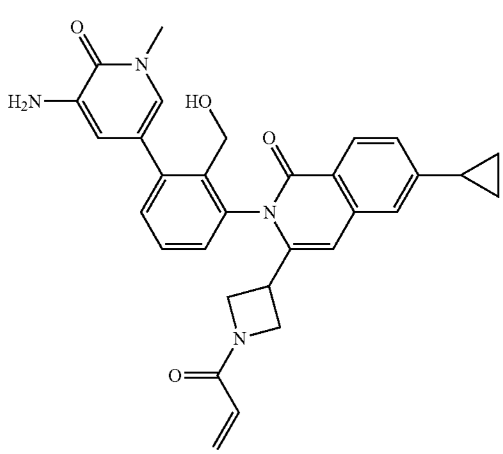 [SMILES: C=CC(=O)N1CC(c2cc3cc(C4CC4)ccc3c(=O)n2-c2cccc(-c3cc(N)c(=O)n(C)c3)c2CO)C1] | 1.9 | A | 1.47 | 521.0 (M − H) |

-continued

Table of compounds and Biological activity

| Example | Structure | BTK IC$_{50}$ (nM) | HPLC Method | RT (min) | m/z |
|---|---|---|---|---|---|
| 12 | 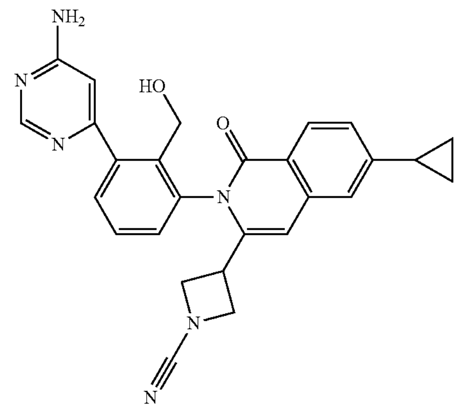 [SMILES: N#CN1CC(c2cc3cc(C4CC4)ccc3c(=O)n2-c2cccc(-c3cc(N)ncn3)c2CO)C1] | 3.3 | B | 0.97 | 463.2 (M − H) |
| 13 | 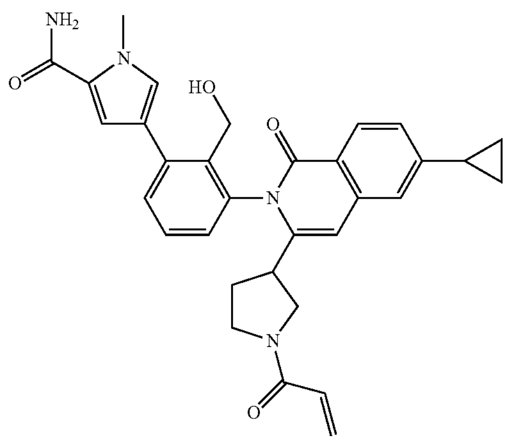 [SMILES: C=CC(=O)N1CCC(c2cc3cc(C4CC4)ccc3c(=O)n2-c2cccc(-c3cc(C(N)=O)n(C)c3)c2CO)C1] | 2.4 | B | 0.78, 0.82 | 537.3 (M + H) |
| 14 | 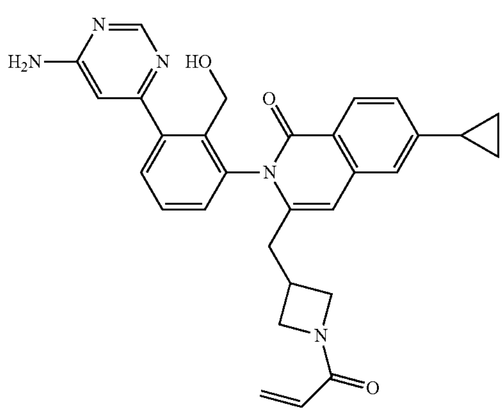 [SMILES: C=CC(=O)N1CC(Cc2cc3cc(C4CC4)ccc3c(=O)n2-c2cccc(-c3cc(N)ncn3)c2CO)C1] | 19 | A | 0.57 | 508.2 (M + H) |

-continued

Table of compounds and Biological activity

| Example | Structure | BTK IC$_{50}$ (nM) | HPLC Method | RT (min) | m/z |
|---------|-----------|--------------------|-----------|----------|-----|
| 15 | 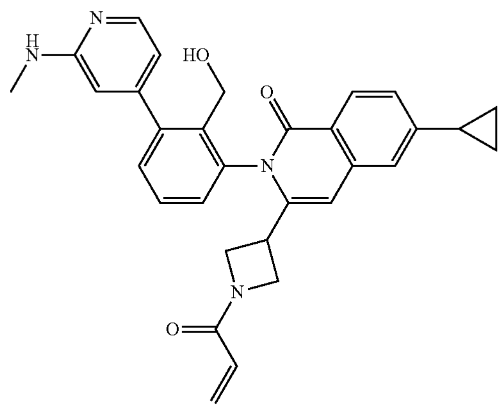 [SMILES: C=CC(=O)N1CC(c2cc3cc(C4CC4)ccc3c(=O)n2-c2cccc(-c3ccnc(NC)c3)c2CO)C1] | 4.2 | A | 1.02 | 507.3 (M + H) |
| 16 | 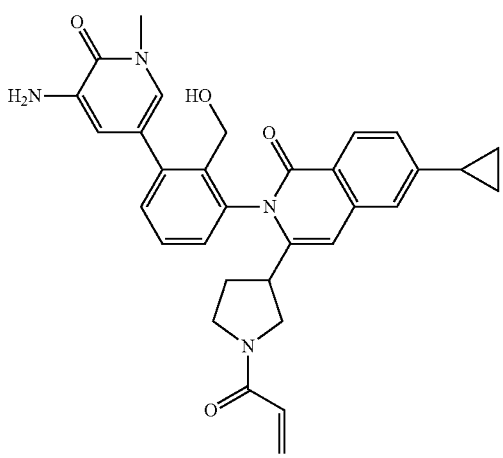 [SMILES: C=CC(=O)N1CCC(c2cc3cc(C4CC4)ccc3c(=O)n2-c2cccc(-c3cc(N)c(=O)n(C)c3)c2CO)C1] | 20 | A | 1.55, 1.66 | 537.3 (M + H) |
| 17 | 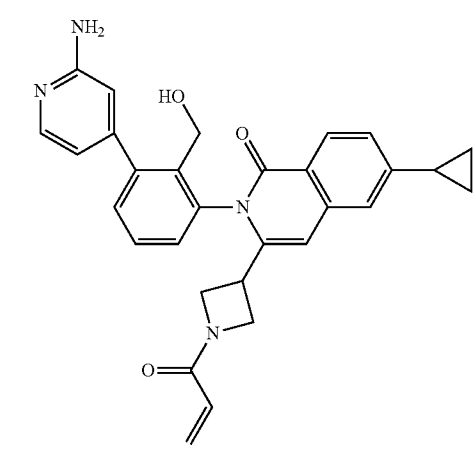 [SMILES: C=CC(=O)N1CC(c2cc3cc(C4CC4)ccc3c(=O)n2-c2cccc(-c3ccnc(N)c3)c2CO)C1] | 0.9 | A | 0.94 | 491.9 (M − H) |

-continued
Table of compounds and Biological activity
| Example | Structure | BTK IC$_{50}$ (nM) | HPLC Method | RT (min) | m/z |
|---|---|---|---|---|---|
| 18 | 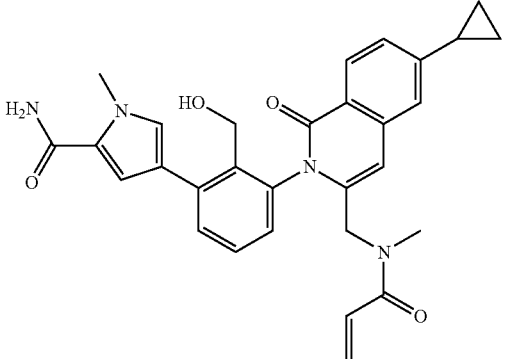 [SMILES: C=CC(=O)N(C)Cc1cc2cc(C3CC3)ccc2c(=O)n1-c1cccc(-c2cc(C(N)=O)n(C)c2)c1CO] | 59 | B | 0.78 | 511.2 (M + H) |
| 19 | 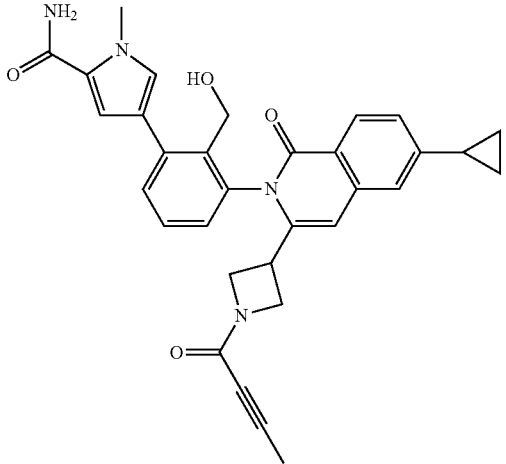 [SMILES: CC#CC(=O)N1CC(c2cc3cc(C4CC4)ccc3c(=O)n2-c2cccc(-c3cc(C(N)=O)n(C)c3)c2CO)C1] | 64 | A | 1.93 | 533.3 (M − H) |
| 20 | 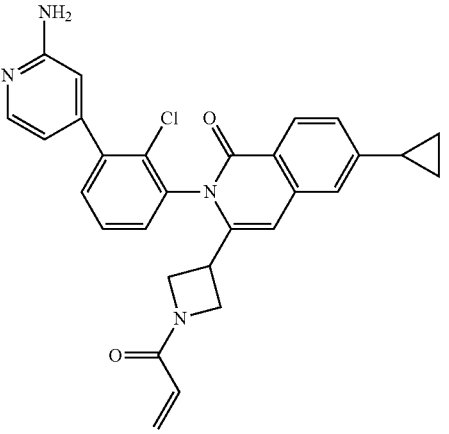 [SMILES: C=CC(=O)N1CC(c2cc3cc(C4CC4)ccc3c(=O)n2-c2cccc(-c3ccnc(N)c3)c2Cl)C1] | 8.9 | A | 0.95 | 497.2 (M + H) |

-continued

Table of compounds and Biological activity

| Example | Structure | BTK IC$_{50}$ (nM) | HPLC Method | RT (min) | m/z |
|---|---|---|---|---|---|
| 21 | 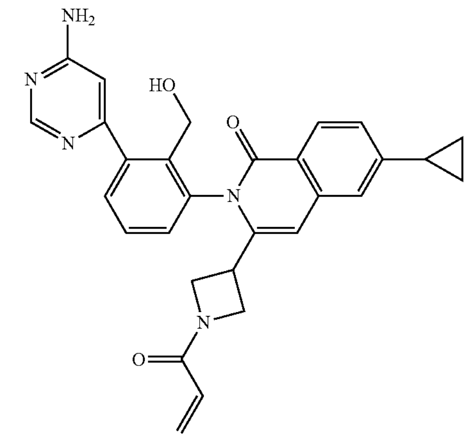 [SMILES: C=CC(=O)N1CC(c2cc3cc(C4CC4)ccc3c(=O)n2-c2cccc(-c3cc(N)ncn3)c2CO)C1] | 0.48 | A | 0.89 | 492.2 (M − H) |
| 22 | 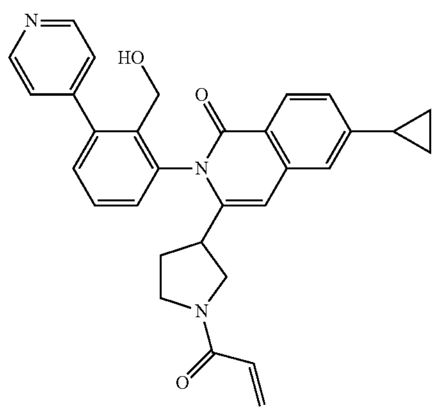 [SMILES: C=CC(=O)N1CCC(c2cc3cc(C4CC4)ccc3c(=O)n2-c2cccc(-c3ccncc3)c2CO)C1] | 37 | A | 0.93, 1.02 | 492.0 (M + H) |
| 23 | 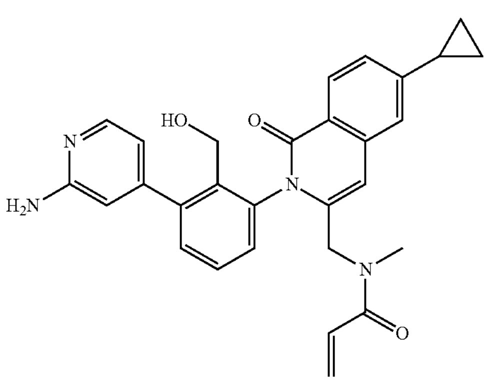 [SMILES: C=CC(=O)N(C)Cc1cc2cc(C3CC3)ccc2c(=O)n1-c1cccc(-c2ccnc(N)c2)c1CO] | 120 | B | 0.51 | 481.2 (M + H) |

-continued

Table of compounds and Biological activity

| Example | Structure | BTK IC$_{50}$ (nM) | HPLC Method | RT (min) | m/z |
|---------|-----------|--------------------|-------------|----------|-----|
| 24 | 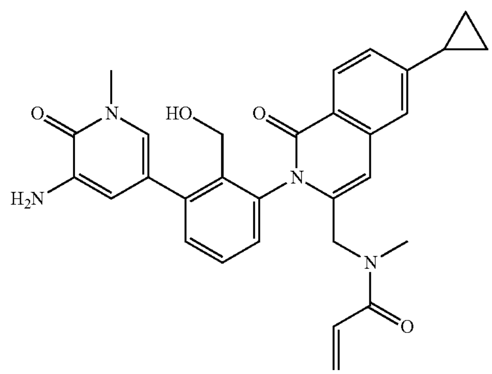 [SMILES: C=CC(=O)N(C)Cc1cc2cc(C3CC3)ccc2c(=O)n1-c1cccc(-c2cc(N)c(=O)n(C)c2)c1CO] | 140 | B | 0.77 | 511.2 (M + H) |
| 25 | 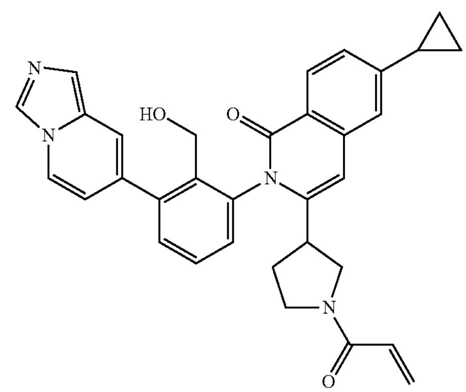 [SMILES: C=CC(=O)N1CCC(c2cc3cc(C4CC4)ccc3c(=O)n2-c2cccc(-c3ccn4cncc4c3)c2CO)C1] | 160 | A | 1.05 | 531.0 (M + H) |
| 26 | 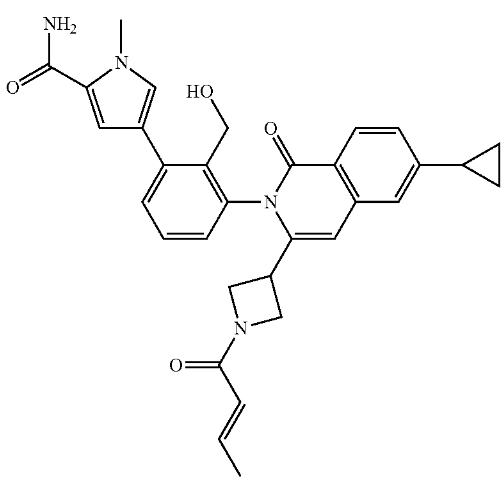 [SMILES: C/C=C/C(=O)N1CC(c2cc3cc(C4CC4)ccc3c(=O)n2-c2cccc(-c3cc(C(N)=O)n(C)c3)c2CO)C1] | 230 | B | 0.83 | 537.2 (M + H) |

-continued
Table of compounds and Biological activity
| Example | Structure | BTK IC$_{50}$ (nM) | HPLC Method | RT (min) | m/z |
|---------|-----------|--------------------|-------------|----------|-----|
| 27 | 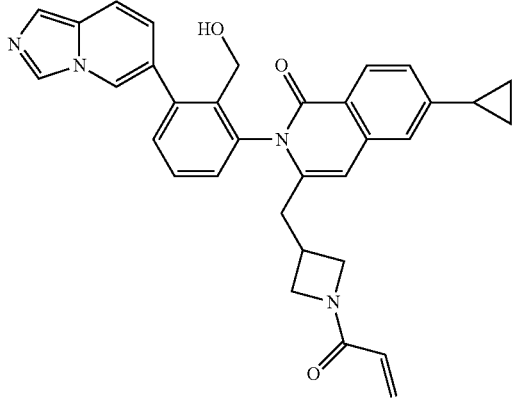 [SMILES: C=CC(=O)N1CC(Cc2cc3cc(C4CC4)ccc3c(=O)n2-c2cccc(-c3ccc4cncn4c3)c2CO)C1] | 310 | A | 1.12 | 531.4 (M + H) |
| 28 | 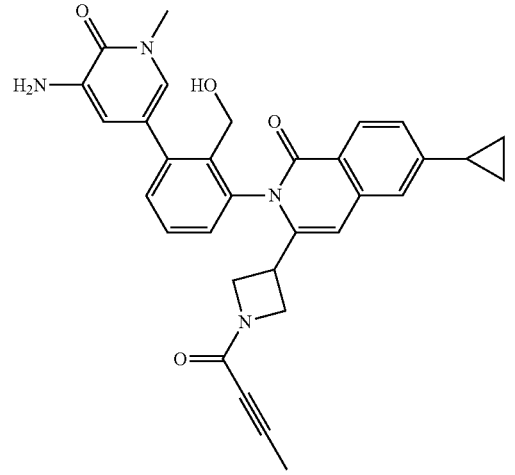 [SMILES: CC#CC(=O)N1CC(c2cc3cc(C4CC4)ccc3c(=O)n2-c2cccc(-c3cc(N)c(=O)n(C)c3)c2CO)C1] | 310 | A | 1.67 | 533.2 (M − H) |
| 29 | 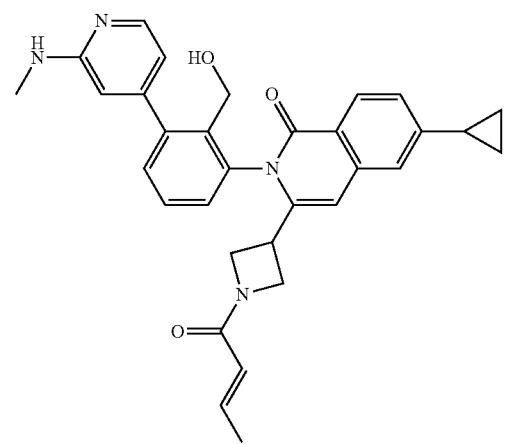 [SMILES: C/C=C/C(=O)N1CC(c2cc3cc(C4CC4)ccc3c(=O)n2-c2cccc(-c3ccnc(NC)c3)c2CO)C1] | 440 | B | 0.56 | 521.0 (M + H) |

-continued

Table of compounds and Biological activity

| Example | Structure | BTK IC$_{50}$ (nM) | HPLC Method | RT (min) | m/z |
|---|---|---|---|---|---|
| 30 | 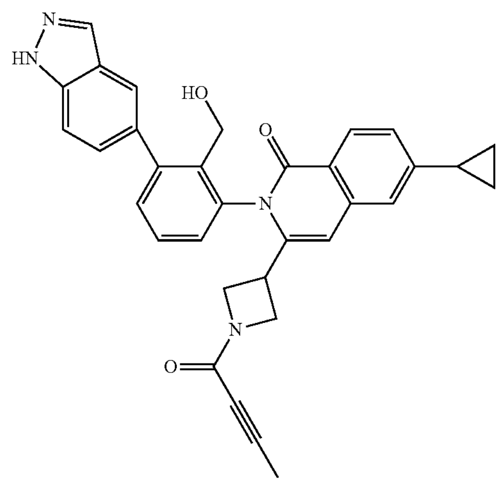 [SMILES: CC#CC(=O)N1CC(c2cc3cc(C4CC4)ccc3c(=O)n2-c2cccc(-c3ccc4[nH]ncc4c3)c2CO)C1] | 450 | A | 1.96 | 527.2 (M − H) |
| 31 | 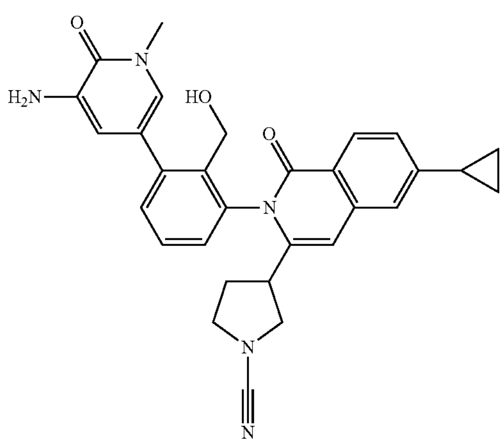 [SMILES: Cn1cc(-c2cccc(-n3c(C4CCN(C#N)C4)cc4cc(C5CC5)ccc4c3=O)c2CO)cc(N)c1=O] | 480 | A | 1.63, 1.71 | 506.2 (M − H) |
| 32 | 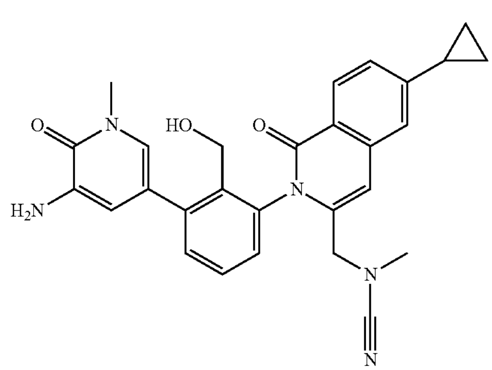 [SMILES: CN(C#N)Cc1cc2cc(C3CC3)ccc2c(=O)n1-c1cccc(-c2cc(N)c(=O)n(C)c2)c1CO] | 490 | B | 0.76 | 482.2 (M + H) |

-continued

Table of compounds and Biological activity

| Example | Structure | BTK IC$_{50}$ (nM) | HPLC Method | RT (min) | m/z |
|---|---|---|---|---|---|
| 33 | 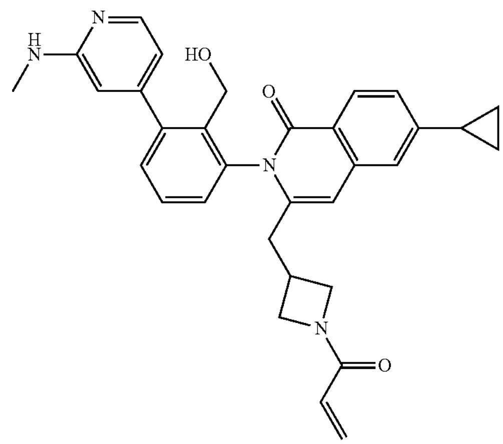 [SMILES: C=CC(=O)N1CC(Cc2cc3cc(C4CC4)ccc3c(=O)n2-c2cccc(-c3ccnc(NC)c3)c2CO)C1] | 510 | B | 0.54 | 521.2 (M + H) |
| 34 | 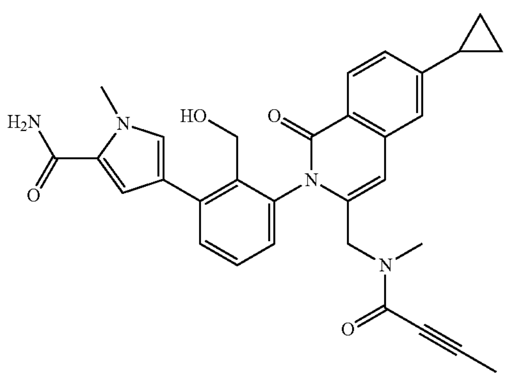 [SMILES: CC#CC(=O)N(C)Cc1cc2cc(C3CC3)ccc2c(=O)n1-c1cccc(-c2cc(C(N)=O)n(C)c2)c1CO] | 530 | B | 0.81 | 523.2 (M + H) |
| 35 | 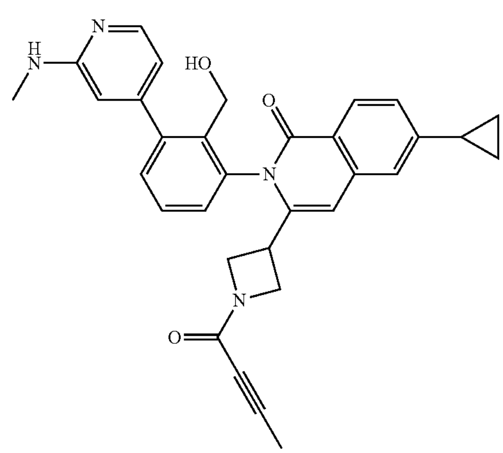 [SMILES: CC#CC(=O)N1CC(c2cc3cc(C4CC4)ccc3c(=O)n2-c2cccc(-c3ccnc(NC)c3)c2CO)C1] | 530 | B | 0.56 | 519.2 (M + H) |

Table of compounds and Biological activity
| Example | Structure | BTK IC$_{50}$ (nM) | HPLC Method | RT (min) | m/z |
|---|---|---|---|---|---|
| 36 | 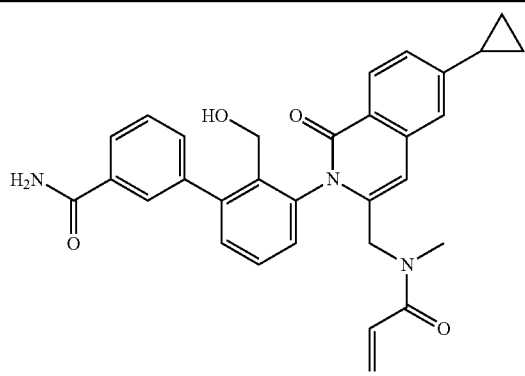 | 580 | B | 0.78 | 508.2 (M + H) |
| 37 | 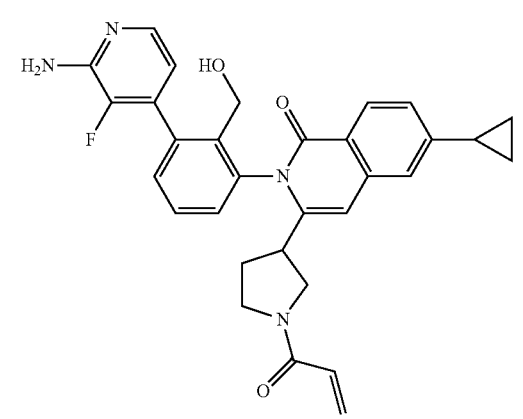 [SMILES: C=CC(=O)N1CCC(c2cc3cc(C4CC4)ccc3c(=O)n2-c2cccc(-c3ccnc(N)c3F)c2CO)C1] | 620 | B | 0.71, 0.74 | 525.3 (M + H) |
| 38 | 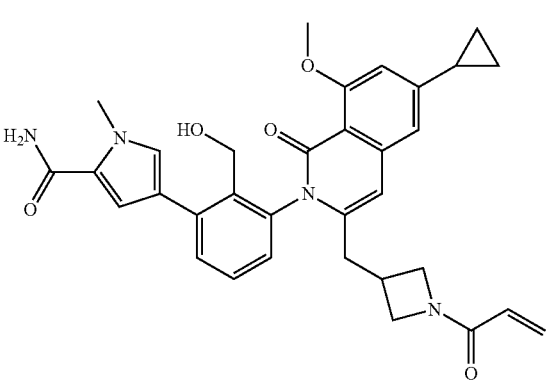 [SMILES: C=CC(=O)N1CC(Cc2cc3cc(C4CC4)cc(OC)c3c(=O)n2-c2cccc(-c3cc(C(N)=O)n(C)c3)c2CO)C1] | 250 | A | 1.71 | 567.3 (M + H) |
| 39 | 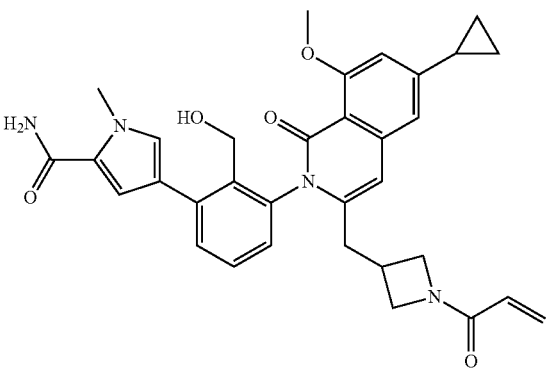 [SMILES: C=CC(=O)N1CC(Cc2cc3cc(C4CC4)cc(OC)c3c(=O)n2-c2cccc(-c3cc(C(N)=O)n(C)c3)c2CO)C1] | 110 | B | 0.84, 0.87 | 549.2 (M + H) |

-continued

Table of compounds and Biological activity

| Example | Structure | BTK IC$_{50}$ (nM) | HPLC Method | RT (min) | m/z |
|---|---|---|---|---|---|
| 40 | 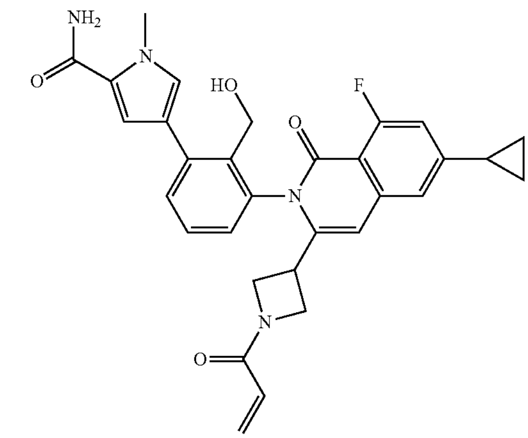 [SMILES: C=CC(=O)N1CC(c2cc3cc(C4CC4)cc(F)c3c(=O)n2-c2cccc(-c3cc(C(N)=O)n(C)c3)c2CO)C1] | 0.42 | B | 0.77 | 541.1 (M + H) |
| 41 | 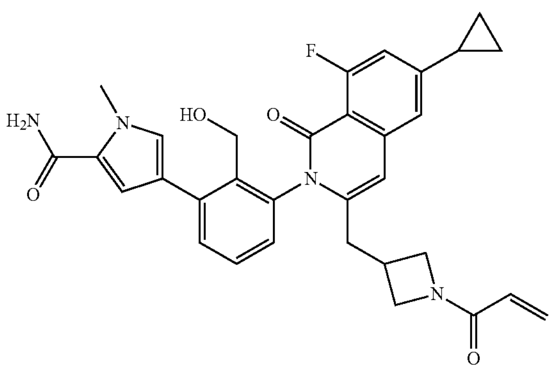 [SMILES: C=CC(=O)N1CC(Cc2cc3cc(C4CC4)cc(F)c3c(=O)n2-c2cccc(-c3cc(C(N)=O)n(C)c3)c2CO)C1] | 0.71 | A | 1.85 | 555.3 (M + H) |
| 42 | 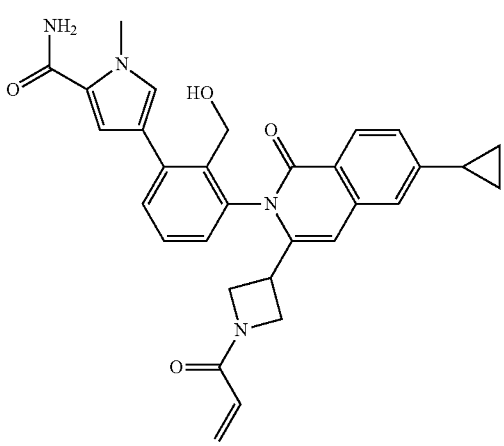 [SMILES: C=CC(=O)N1CC(c2cc3cc(C4CC4)ccc3c(=O)n2-c2cccc(-c3cc(C(N)=O)n(C)c3)c2CO)C1] | 560 | B | 0.8 | 523.2 (M + H) |

Table of compounds and Biological activity

| Example | Structure | BTK IC$_{50}$ (nM) | HPLC Method | RT (min) | m/z |
|---|---|---|---|---|---|
| 43 | 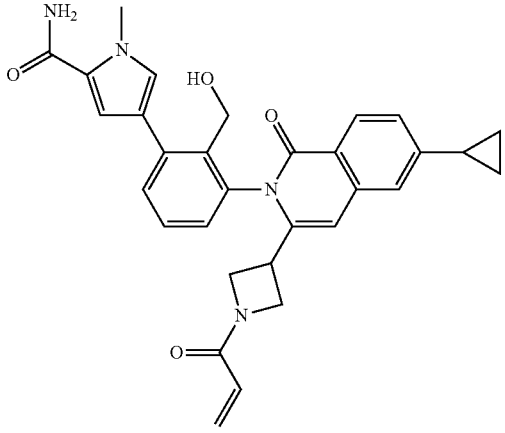 [SMILES: C=CC(=O)N1CC(c2cc3cc(C4CC4)ccc3c(=O)n2-c2cccc(-c3cc(C(N)=O)n(C)c3)c2CO)C1] | 0.56 | B | 0.8 | 523.2 (M + H) |

* Compounds 42 and 43 are atropisomers of Example 7 or the pharmaceutically acceptable salts thereof.

The present invention further relates to metabolites, and prodrugs of compounds of the formula (I).

The present invention further relates to a pharmaceutically acceptable salt of a compound of the formula (I) with inorganic or organic acids or bases.

In another aspect the invention relates to compounds of formula (I)—or the pharmaceutically acceptable salts thereof—as medicaments.

In another aspect the invention relates to compounds of formula (I)—or the pharmaceutically acceptable salts thereof—for use in a method for treatment of a patient.

In another aspect the invention relates to compounds of formula (I)—or the pharmaceutically acceptable salts thereof—for use in the treatment of autoimmune diseases and allergic disorders.

In another aspect the invention relates to the use of compounds of formula (I)—or the pharmaceutically acceptable salts thereof—for preparing a pharmaceutical composition for the treatment of autoimmune diseases and allergic disorders.

In another aspect the invention relates to a method for the treatment of autoimmune diseases and allergic disorders comprising administering a therapeutically effective amount of a compound of formula (I)—or one of the pharmaceutically acceptable salts thereof—to a patient.

In another aspect the invention relates to a pharmaceutical preparation containing as active substance one or more compounds of formula (I)—or the pharmaceutically acceptable salts thereof—optionally in combination with conventional excipients and/or carriers.

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x carbon atoms.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-4}$ alkyl" includes for example $H_3C$—, $H_3C$—$CH_2$—, $H_3C$—$CH_2$—$CH_2$—, $H_3C$—$CH$ ($CH_3$)—, $H_3C$—$CH_2$—$CH_2$—$CH_2$—, $H_3C$—$CH_2$—$CH$ ($CH_3$)—, $H_3C$—$CH(CH_3)$—$CH_2$—, $H_3C$—$C(CH_3)_2$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), etc.

By the terms propyl, butyl, etc. without any further definition are meant saturated hydrocarbon groups with the corresponding number of carbon atoms, wherein all isomeric forms are included.

An alkyl group when halogenated will become a haloalkyl group. Haloalkyl is derived from an alkyl by replacing one or more hydrogen atoms of the hydrocarbon chain independently of one another by halogen atoms, which may be identical or different. If a haloalkyl is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CHFCH_2CH_3$, —$CHFCH_2CF_3$ etc.

Halogen relates to fluorine, chlorine, bromine and/or iodine atoms.

All cyclic and acyclic systems defined in this section hereinabove shall be understood to be optionally partially or fully halogenated where possible and unless otherwise indicated.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, atropisomers, etc.) and racemates thereof as well as mixtures in different proportions of the separate enantiomers, mixtures of diastereomers, mixtures of atropisomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Examples of atropisomers of compounds from the instant invention are:

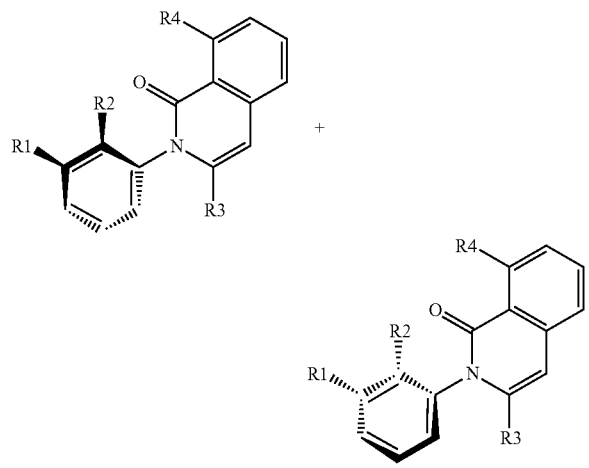

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

In a representation such as for example

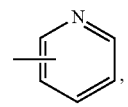

the solid line means that the ring system may be attached to the molecule via the carbon atom 1, 2 or 3, and is thus equivalent to the following representation

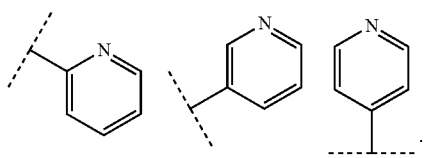

By a therapeutically effective amount for the purposes of this invention is meant a quantity of substance that is capable of obviating symptoms of illness or alleviating these symptoms, or which prolong the survival of a treated patient.

| List of abbreviations | |
|---|---|
| Ac | Acetyl |
| ACN | Acetonitrile |
| aq | Aqueous |
| ATP | adenosine triphosphate |
| Bn | Benzyl |
| Bu | Butyl |
| Boc | tert-butyloxycarbonyl |
| cat | Catalyst |
| conc | concentrated |
| d | day(s) |
| TLC | thin layer chromatography |
| DIEA | N,N-diisopropylethylamine |
| DMAP | 4-N,N-dimethylaminopyridine |
| DMA | N,N-dimethylacetamide |
| DME | 1,2-dimethoxyethane |
| DMF | N,N-dimethylformamide |
| DMSO | Dimethylsulphoxide |
| dppf | 1.1'-bis(diphenylphosphino)ferrocene |
| EDC | 1-Ethyl-3-(3-dimethylaminopropyl)carbodiimide |
| ESI | electron spray ionization |
| Et | Ethyl |
| $Et_2O$ | diethyl ether |
| EtOAc | ethyl acetate |
| EtOH | Ethanol |
| h | hour(s) |
| HATU | O-(7-azabenzotriazol-1-yl)-N,N,N',N'-tetramethyl-uronium hexafluorophosphate |
| Hep | Heptane |
| HPLC | high performance liquid chromatography |
| i | Iso |
| LC | liquid chromatography |
| LiHMDS | lithium bis(trimethylsilyl)amide |
| sln. | Solution |
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf ($R_f$) | retention factor |
| RP | reversed phase |
| RT | Retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMP | 2,2,6,6-tetramethylpiperidine |
| TMS | Trimethylsilyl |
| TRIS | tris(hydroxymethyl)-aminomethane |
| Ts | p-Tosyl |
| TsOH | p-toluenesulphonic acid |
| UV | Ultraviolet |

Features and advantages of the present invention will become apparent from the following detailed examples which illustrate the fundamentals of the invention by way of example without restricting its scope:

Preparation of the Compounds According to the Invention

General Synthetic Methods

Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid or 0.1% TFA and used one of the following columns:
a) Waters Sunfire OBD C18 5 µm 30×150 mm column.
b) Waters XBridge OBD C18 5 µm 30×150 mm column.
c) Waters ODB C8 5 µm 19×150 mm column.
d) Waters Atlantis ODB C18 5 µm 19×50 mm column
e) Waters Atlantis T3 OBD 5 µm 30×100 mm column.
f) Phenomenex Gemini Axia C18 5 µm 30×100 mm column.

HPLC Methods:
Analytical LC/MS Analysis Method A:
ESI +/− ion mode 80-1000 Da
Column: CSH C18 2.1×50 mm, 1.7 um particle diameter
Gradient:

| Time (min) | 95% Water/5% ACN (0.05% formic acid) | ACN (0.05% formic acid) | Flow (ml/min) |
|---|---|---|---|
| 0 | 90 | 10 | 0.8 |
| 4.45 | 0 | 100 | 0.8 |
| 4.58 | 0 | 100 | 0.8 |

Analytical LC/MS Analysis Method B:
ESI +/− ion mode 80-1000 Da
Column: CSH C18 2.1×50 mm, 1.7 um particle diameter
Gradient:

| Time (min) | 95% Water/5% ACN (0.05% formic acid %) | ACN (0.05% formic acid) | Flow (ml/min) |
|---|---|---|---|
| 0 | 90 | 10 | 0.8 |
| 1.19 | 0 | 100 | 0.8 |
| 1.70 | 0 | 100 | 0.8 |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared as shown in Scheme Ia and Ib below.

Scheme Ia:

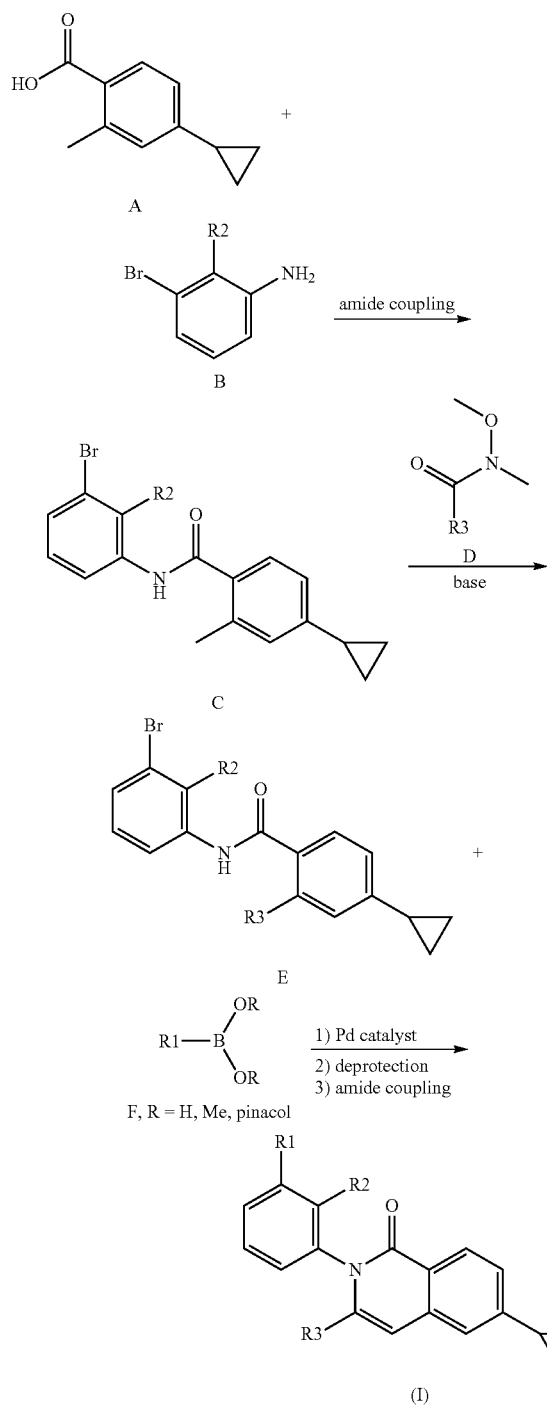

In scheme Ia, carboxylix acid A and aniline B are coupled together using standard amide coupling conditions to give amide C. Treatment of amide C with base followed by Weinreb amide D give isoquinoline E. Isoquinoline E and boronic acid or boronic ester F are subjected to a palladium catalysed cross-cupling reaction followed by a deprotetion of protecting groups and a final amide coupling to afford the compound of general formula (I).

SYNTHETIC EXAMPLES

Method 1

Synthesis of Intermediate I-1

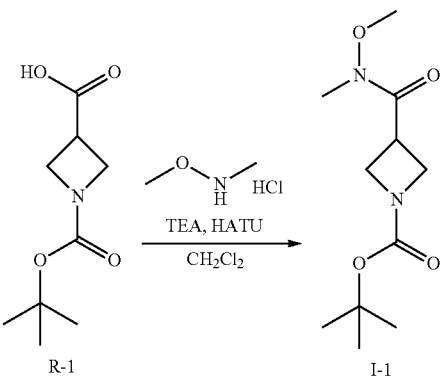

A solution of R-1 (50 g, 250 mmol) and HATU (104 g, 270 mmol) in $CH_2Cl_2$ (8000 mL) is treated with TEA (135 mL, 1000 mmol). The mixture is stirred for 16 h then washed with saturated aqueous ammonium chloride and filtered through a phase separator. The organics are collected and volatiles are removed in vacuo to afford a crude residue that is purified by flash chromatography ($SiO_2$, 12% EtOAc in heptane to 100% EtOAc) to afford I-1 (46 g, 76%) m/z 245.1 [M+H].

The following intermediates are prepared in similar fashion from the corresponding carboxylic acids:

| Structure | Intermediate | m/z |
|---|---|---|
| 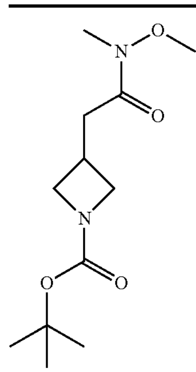 | I-2 | 259.1 [M + H] |
| 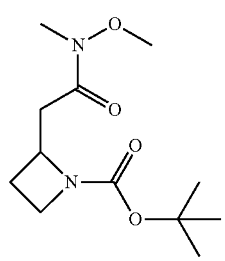 [SMILES: CON(C)C(=O)CC1CCN1C(=O)OC(C)(C)C] | I-3 | 259.1 [M + H] |

| Structure | Intermediate | m/z |
|---|---|---|
| 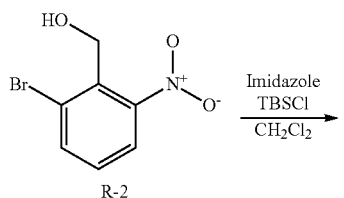 | I-4 | 259 [M + H] |
| 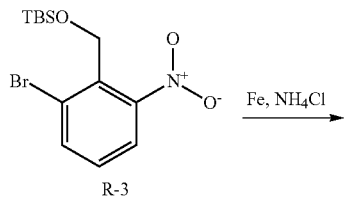 | I-5 | 233.1 [M + H] |

Method 2

Synthesis of Intermediate I-6

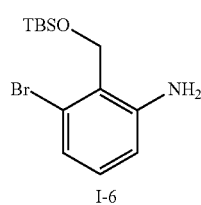

To a solution of R-2 (19 g, 82 mol) in $CH_2Cl_2$ (200 mL) is added imidazole (11.1 g, 164 mol) and TBSCl (18.5 g, 123 mmol). The mixture is stirred at ambient temperature for 1 h then filtered. The filtrate is collected and volatiles removed n vacuo. The residue is diluted with EtAOc and washed with water, 1N aq HCl and brine then dried over $Na_2SO_4$, filtered, and concentrated. The residue is purified by flash chromatography ($SiO_2$, heptane to 15% EtOAc in heptane) to give I-6 (28 g, 99%) m/z 346.0 [M+H].

Method 3

Synthesis of Intermediate I-7

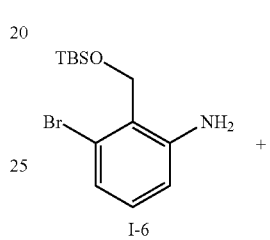

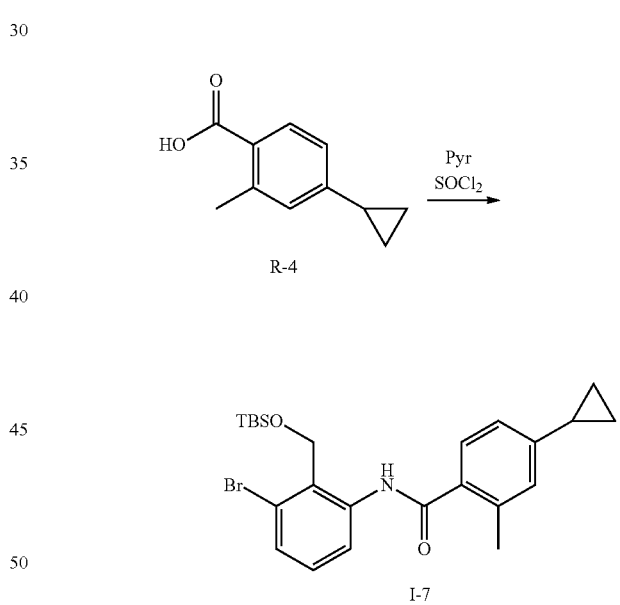

To R-4 (3.5 g, 20 mmol) is added thionyl chloride (20 mL). The mixture is heated at 70° C. for 2 h then thionyl chloride is removed in vacuo. The resulting acid chloride is dissolved in Pyr (16 mL) and treated with I-6 (7.5 g, 24 mmol) and stirred for 1 h at ambient temperature. The mixture is then acidified with 1N aq HCl, extracted with EtOAc, washed with saturated aq $NaHCO_3$, brine, dried with $Na_2SO_4$, filtered and concentrated. The residue is purified by flash chromatography ($SiO_2$, heptane to 50% EtOAc in heptane) to give I-7 (8 g, 85%).

Method 4

Synthesis of Intermediate I-8

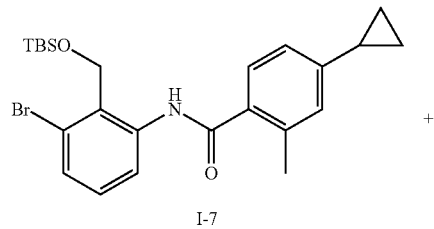

I-7

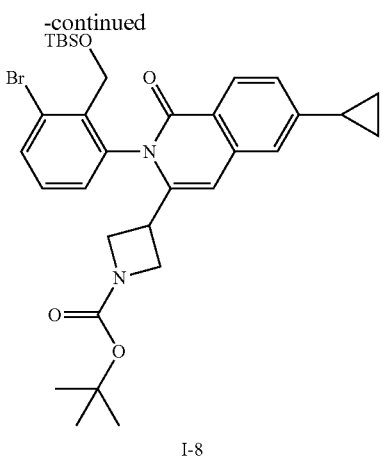

I-8

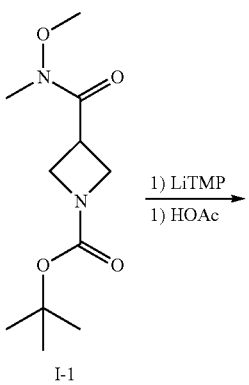

I-1

A solution of TMP (27 mL, 158 mmol) in THF (600 mL) is cooled to −20° C. and treated with a 2.7M n-BuLi solution in heptane (53 mL). The mixture is stirred for 10 min then a solution of I-7 (15 g, 31.6 mmol) in THF (80 mL) is added dropwise. The mixture is stirred at −20° C. for 30 min then treated with a solution of I-1 (15.5 g, 63 mmol) in THF (50 mL). The mixture is allowed to warm to ambient temperature and stirred for 1 h. The mixture is treated with saturated aq NH$_4$Cl, extracted with EtOAc, washed with brine, dried over Na$_2$SO$_4$, filtered and concentrated. The residue is dissolved in acetic acid (200 mL) and heated at 85° C. for 1 h then concentrated in vacuo to afford a residue that is purified by flash chromatography (SiO$_2$, Hep to 20% EtOAc in Hep) to afford I-8 (9.0 g, 45%) m/z 641.2 [M+H].

The following intermediates are prepared in similar fashion from I-2 to I-5:

| Structure | Intermediate | m/z |
|---|---|---|
| 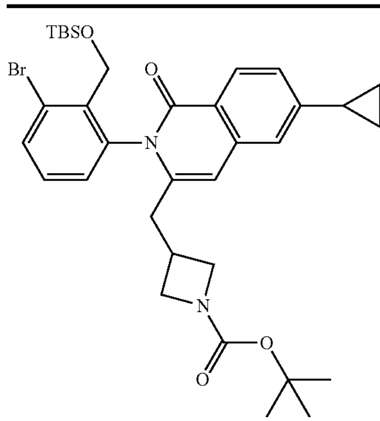 | I-9 | 655.3 [M + H] |
| 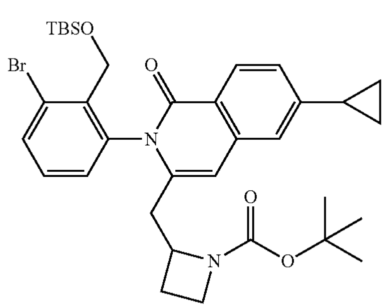 [SMILES: CC(C)(C)OC(=O)N1CCC1Cc1cc2cc(C3CC3)ccc2c(=O)n1-c1cccc(Br)c1CO[Si](C)(C)C(C)(C)C] | I-10 | 655.3 [M + H] |

-continued
| Structure | Intermediate | m/z |
|---|---|---|
| 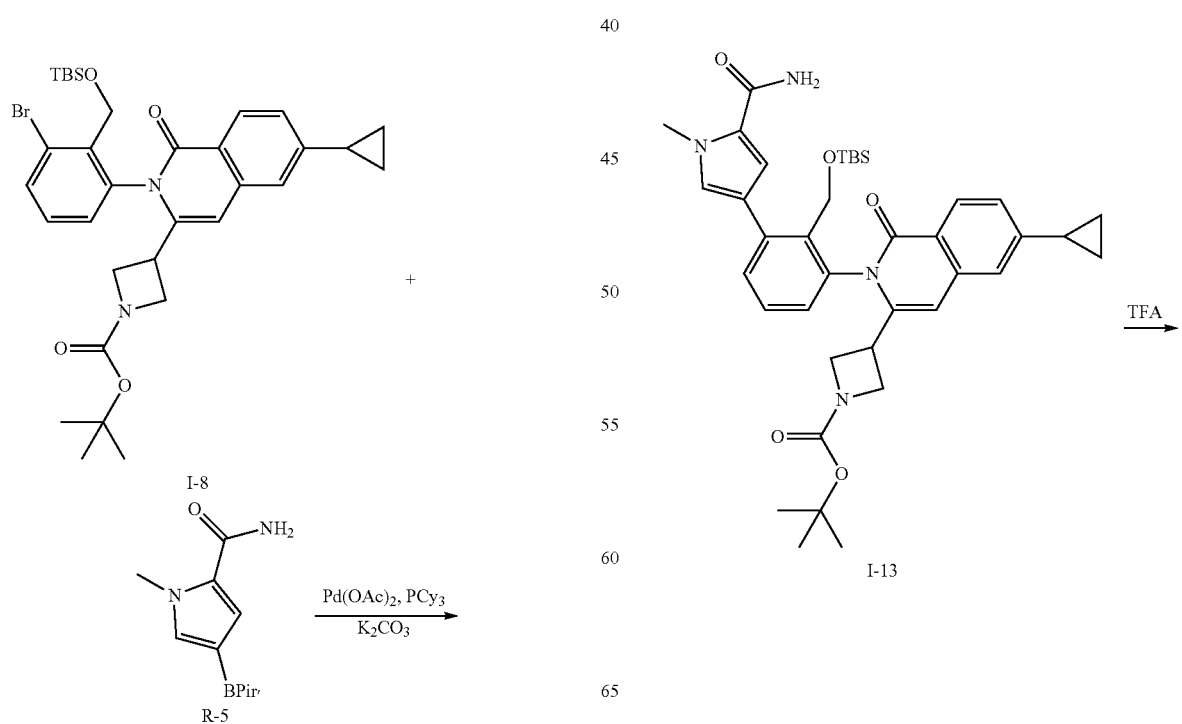 | I-11 | 655.3 [M + H] |
| 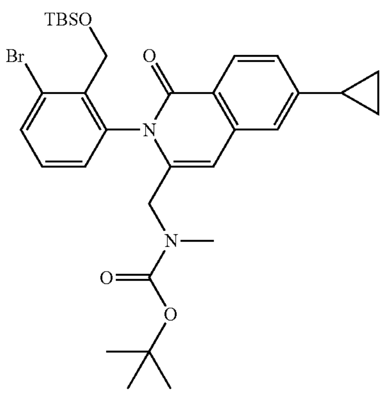 [SMILES: CN(Cc1cc2cc(C3CC3)ccc2c(=O)n1-c1cccc(Br)c1CO[Si](C)(C)C(C)(C)C)C(=O)OC(C)(C)C] | I-12 | 629.1 [M + H] |
Method 5
Synthesis of Intermediate I-14

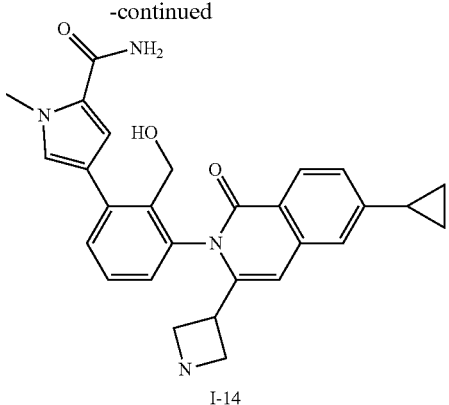
I-14

To a solution of I-8 (9.0 g, 14 mmol), R-5 (5.3 g, 21 mmol), tricyclohexylphosphine (1.2 g, 4.2 mmol), and potassium carbonate (3.9 g, 28 mmol) in DME (120 mL) and water (30 mL) is added palladium acetate (0.44 g, 2.0 mmol). The mixture is heated at 100° C. for 1.5 h then cooled to ambient temperature and triturated with water (100 mL). The solid is filtered, rinsed with water (10 mL), collected and dried then purified by flash chromatography (SiO$_2$, EtOAc) to give I-13 (5.5 g, 57%) m/z 683.6 [M+H].

A solution of I-13 (5.5 g) in TFA (10 mL) is stirred for 1 h at ambient temperature. The volatiles are removed in vacuo, dissolved in CH$_2$Cl$_2$ (100 mL) and treated with 1M aqueous NaOH (20 mL). The mixture is stirred for 1 h then layers are separated. The aqueous is extracted with 10% MeOH in CH$_2$Cl$_2$ and all organics are combined and concentrated in vacuo to afford I-14 (4.1 g, 79%) m/z 565.3 [M+H].

The following intermediates are prepared in similar fashion from the corresponding boronic ester or boronic acid listed in the table:

| Reagent | Structure | Intermediate | m/z |
|---|---|---|---|
| R-6 | 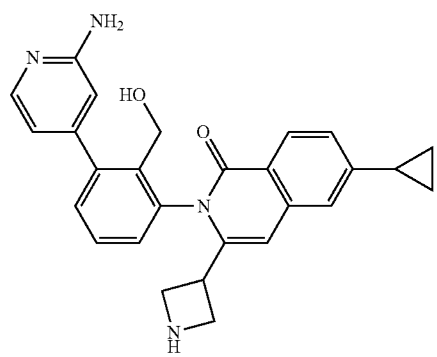 [SMILES: Nc1cc(-c2cccc(-n3c(C4CNC4)cc4cc(C5CC5)ccc4c3=O)c2CO)ccn1] | I-15 | 439.1 [M + H] |
| R-7 | 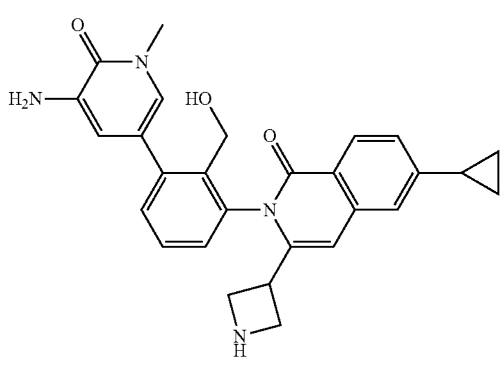 [SMILES: Cn1cc(-c2cccc(-n3c(C4CNC4)cc4cc(C5CC5)ccc4c3=O)c2CO)cc(N)c1=O] | I-16 | 469.3 [M + H] |

-continued

| Reagent | Structure | Intermediate | m/z |
|---------|-----------|--------------|-----|
| R-8 | 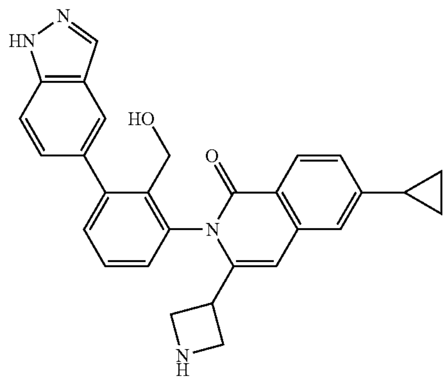 [SMILES: O=c1c2ccc(C3CC3)cc2cc(C2CNC2)n1-c1cccc(-c2ccc3[nH]ncc3c2)c1CO] | I-17 | 463.2 [M + H] |
| R-9 | 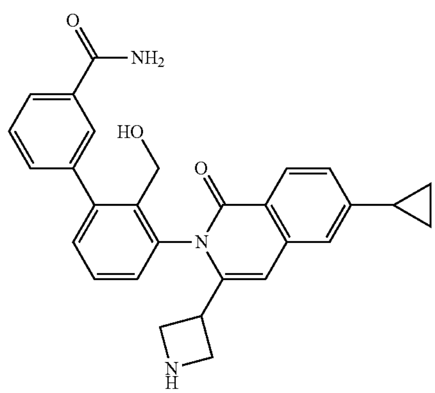 [SMILES: NC(=O)c1cccc(-c2cccc(-n3c(C4CNC4)cc4cc(C5CC5)ccc4c3=O)c2CO)c1] | I-18 | 466.2 [M + H] |
| R-10 | 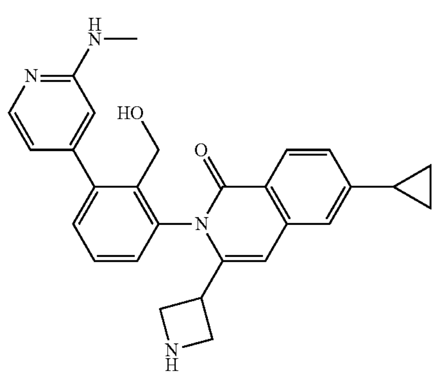 [SMILES: CNc1cc(-c2cccc(-n3c(C4CNC4)cc4cc(C5CC5)ccc4c3=O)c2CO)ccn1] | I-19 | 453.3 [M + H] |

Method 6

Synthesis of Intermediate I-21

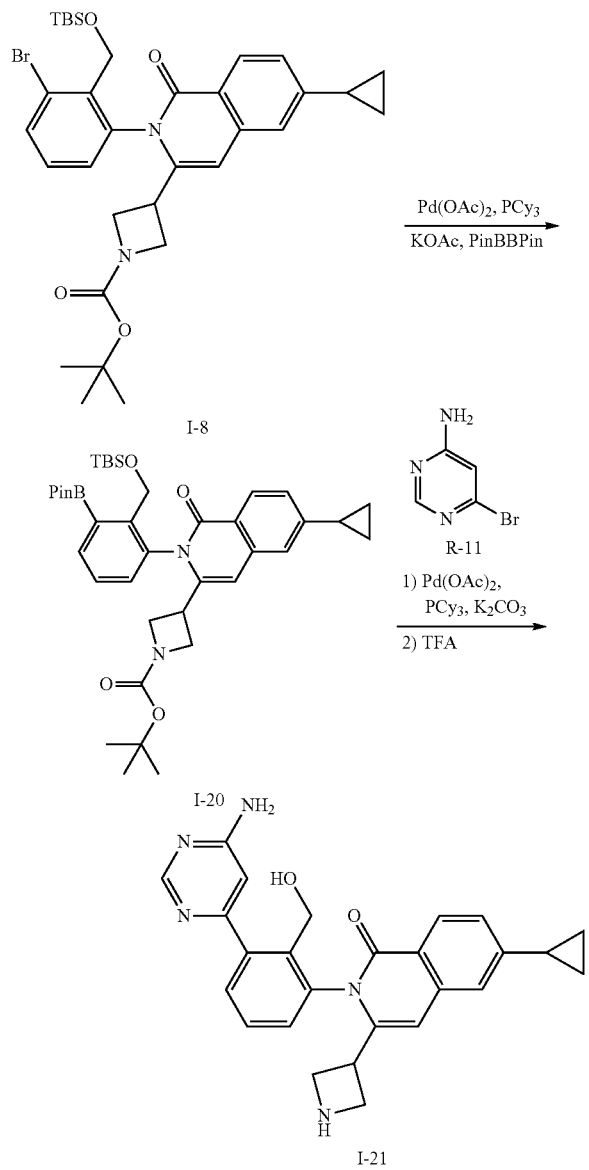

A vial is charged with I-8 (1.00 g, 1.56 mmol), bis(pinacolato)diboron (1.19 g, 4.69 mmol), palladium acetate (18 mg, 0.08 mmol), tricyclohexylphosphine (26 mg, 0.09 mmol) and potassium acetate (0.61 g, 6.25 mmol) then suspended in dioxane (15 mL). The mixture is heated at 100° C. for 4 h then cooled to ambient temperature and concentrated in vacuo. The residue is portioned between EtOAc and water, organics washed with water and brine, dried over sodium sulfate, filtered and concentrated. The residue is purified by flash chromatography (SiO$_2$, Hep to EtOAc) to give I-20 (1.0 g, 93%) m/z 687.4 [M+H].

A mixture of I-20 (1.10 g, 1.12 mmol), R-11 (195 mg, 1.12 mmol), palladium acetate (76 mg, 0.34 mmol), tricyclohexylphosphine (189 mg, 0.67 mmol), and potassium carbonate (465 mg, 3.36 mmol) in DME (12 mL) and water (3 mL) is heated at 100° C. for 4 h then cooled to ambient temperature and concentrated in vacuo. The residue is portioned between EtOAc and water, washed with brine, dried over sodium sulfate, filtered and concentrated. The residue is purified by flash chromatography (SiO$_2$, 0-8% MeOH in CH$_2$Cl$_2$) to give a residue that is dissolved in TFA (4 mL) and stirred for 3 h. The mixture is concentrated, dissolved in CH$_2$Cl$_2$, washed with 1M aqueous NaOH then organics are separated, collected, and concentrated in vacuo to afford I-21 (400 mg, 81%) m/z 440.2 [M+H].

The following intermediates were made in similar fashion from the corresponding intermediates:

| Bromo Intermediate | Structure | Intermediate | m/z |
|---|---|---|---|
| I-9 | ![structure] | I-22 | 454.2 |

Method 7

Synthesis of Intermediate I-25

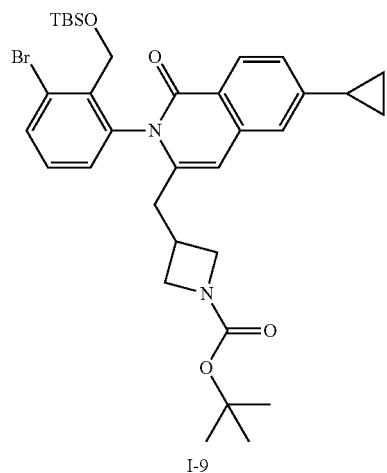

I-9

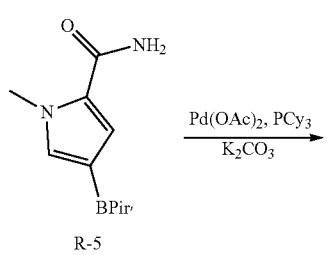

R-5

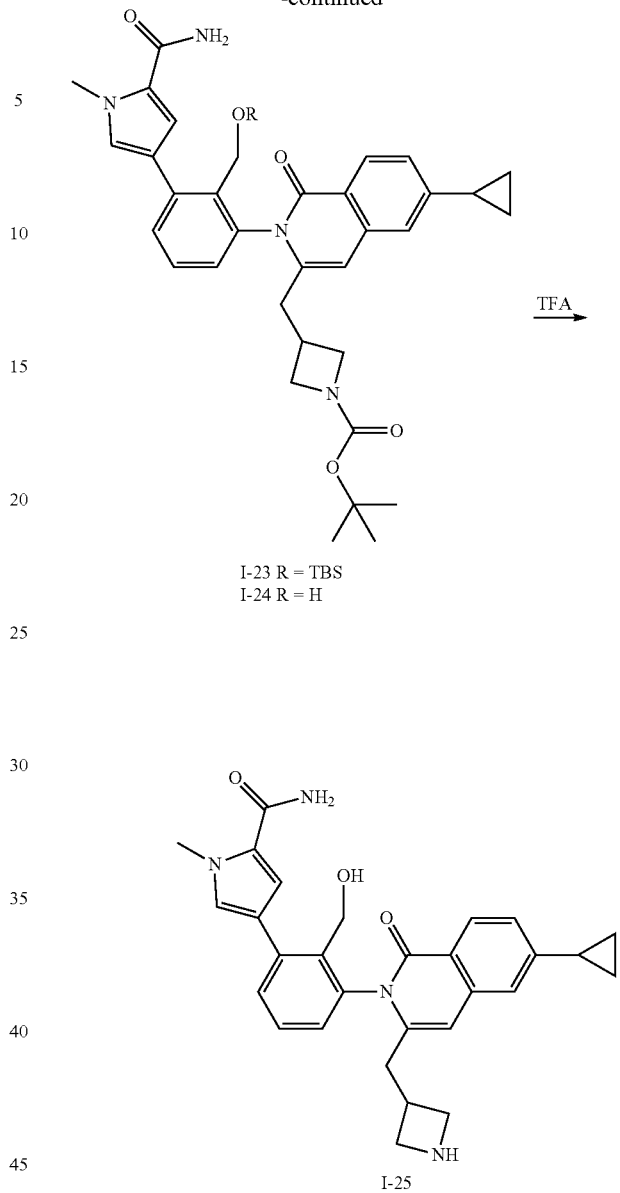

I-23 R = TBS
I-24 R = H

I-25

To a solution of I-9 (0.50 g, 0.77 mmol), R-5 (0.29 g, 1.1 mmol), tricyclohexylphosphine (43 mg, 0.15 mmol), and potassium carbonate (0.21 g, 1.5 mmol) in DME (8 mL) and water (2 mL) is added palladium acetate (17 mg, 0.08 mmol). The mixture is heated at 100° C. for 1 h then cooled to ambient temperature and triturated with water (100 mL). The solid is filtered, rinsed with water (10 mL), collected and dried then purified by flash chromatography (SiO$_2$, EtOAc) to give I-23 (280 mg, 53%) m/z 697.4 [M+H] and I-24 (185 mg, 42%) m/z 583.3 [M+H].

The isolated mixture of both I-23 (280 mg) and I-24 (185 mg) is dissolved in TFA (2 mL) and stirred for 3 h at ambient temperature then concentrated in vacuo. The residue is dissolved in CH$_2$Cl$_2$, washed with 1M aqueous NaOH, organics collected and concentrated to afford I-25 (266 mg, 84%) m/z 483.2 [M+H].

The following intermediates are prepared in similar fashion from the corresponding intermediates:

| Bromo Intermediate | Structure | Intermediate | m/z |
|---|---|---|---|
| I-10 | 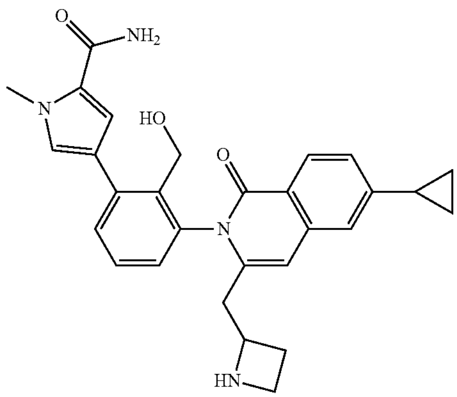 [SMILES: Cn1cc(-c2cccc(-n3c(CC4CCN4)cc4cc(C5CC5)ccc4c3=O)c2CO)cc1C(N)=O] | I-26 | 454.2 |
| I-11 | 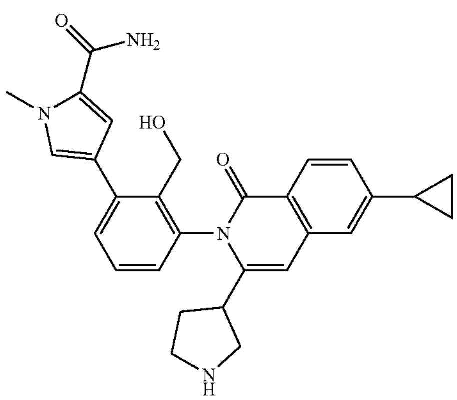 [SMILES: Cn1cc(-c2cccc(-n3c(C4CCNC4)cc4cc(C5CC5)ccc4c3=O)c2CO)cc1C(N)=O] | I-27 | 483.4 |
| I-12 | 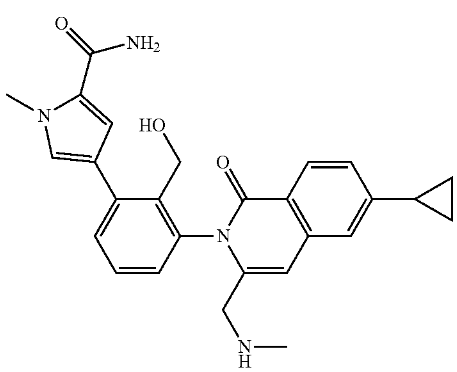 [SMILES: CNCc1cc2cc(C3CC3)ccc2c(=O)n1-c1cccc(-c2cc(C(N)=O)n(C)c2)c1CO] | I-28 | 457.2 |

Method 8

Synthesis of Intermediate I-30

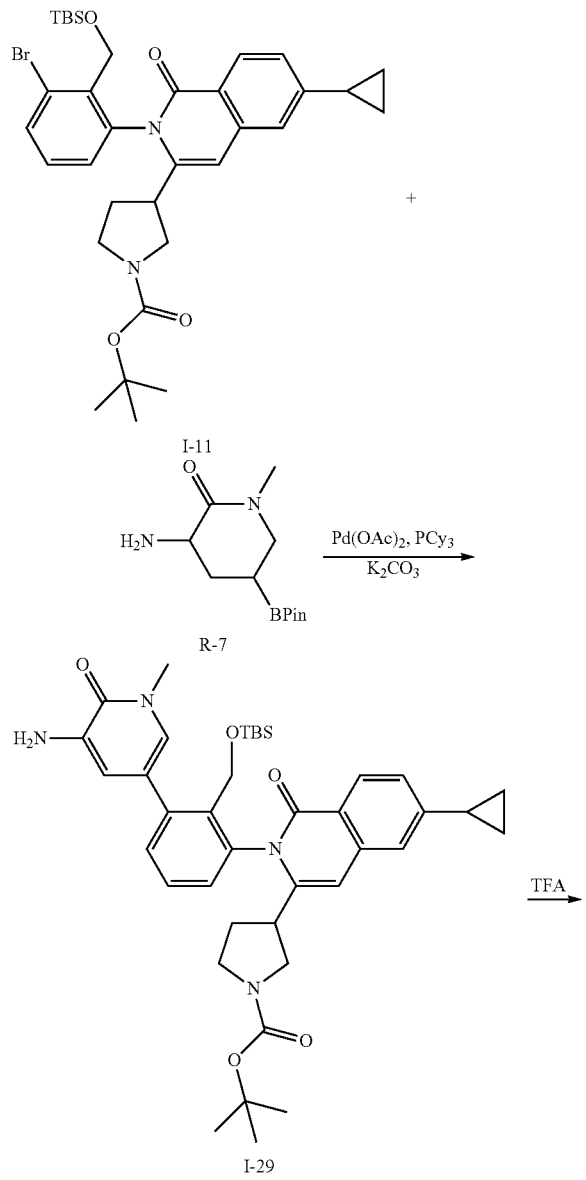

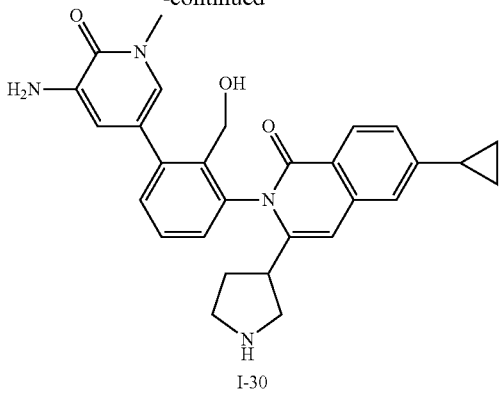

To a solution of I-11 (460 mg, 0.70 mmol), R-7 (264 mg, 1.1 mmol), tricyclohexylphosphine (120 mg, 0.42 mmol), and potassium carbonate (292 mg, 2.1 mmol) in dioxane (8 mL) and water (2 mL) is added palladium acetate (47 mg, 0.21 mmol). The mixture is heated at 100° C. for 1 h then cooled to ambient temperature and triturated with water (100 mL). The solid is filtered, rinsed with water (10 mL), collected and dried then purified by flash chromatography (SiO$_2$, 12-100% EtOAc in Hep) to give I-29 (330 mg, 67%) m/z 697.4 [M+H].

I-29 (330 mg) is dissolved in TFA (2 mL) and stirred for 3 h at ambient temperature then concentrated in vacuo. The residue is dissolved in CH$_2$Cl$_2$, washed with 1M aqueous NaOH, organics collected and concentrated to afford I-30 (230 mg) m/z 483.2 [M+H].

The following intermediates are prepared in similar fashion from the corresponding boronic ester or boronic acid listed in the table:

| Reagent | Structure | Intermediate | m/z |
|---|---|---|---|
| R-12<br>4-pyridyl-B(OH)$_2$ | (4-pyridyl substituted product structure) | I-31 | 438.0 [M + H] |

| Reagent | Structure | Intermediate | m/z |
|---|---|---|---|
| 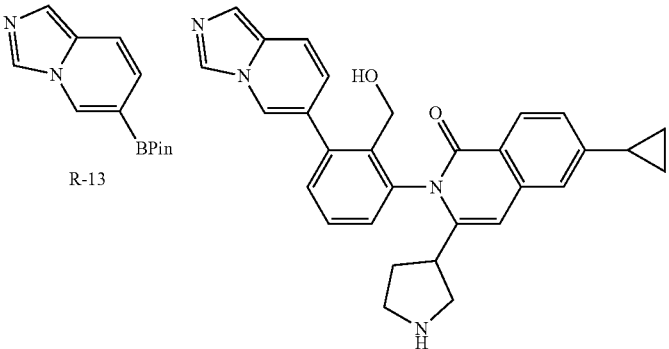<br>R-13 | 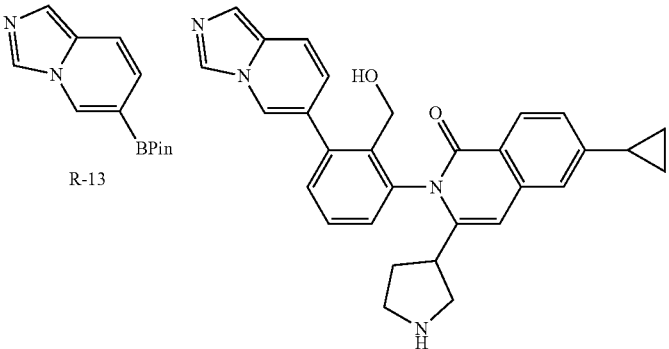 | I-32 | 469.3 [M + H] |

Method 9

Synthesis of Intermediate I-34

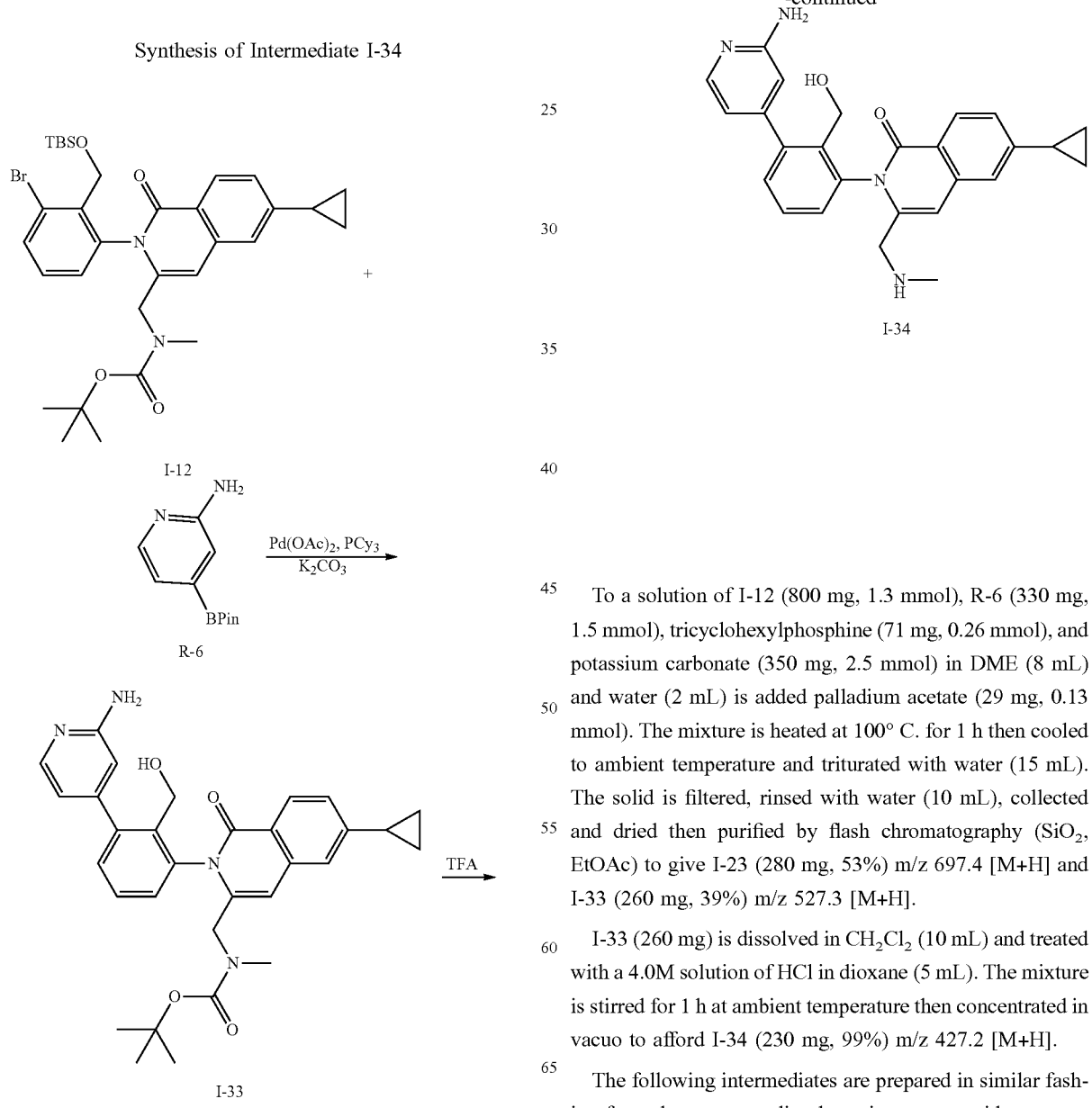

To a solution of I-12 (800 mg, 1.3 mmol), R-6 (330 mg, 1.5 mmol), tricyclohexylphosphine (71 mg, 0.26 mmol), and potassium carbonate (350 mg, 2.5 mmol) in DME (8 mL) and water (2 mL) is added palladium acetate (29 mg, 0.13 mmol). The mixture is heated at 100° C. for 1 h then cooled to ambient temperature and triturated with water (15 mL). The solid is filtered, rinsed with water (10 mL), collected and dried then purified by flash chromatography (SiO$_2$, EtOAc) to give I-23 (280 mg, 53%) m/z 697.4 [M+H] and I-33 (260 mg, 39%) m/z 527.3 [M+H].

I-33 (260 mg) is dissolved in CH$_2$Cl$_2$ (10 mL) and treated with a 4.0M solution of HCl in dioxane (5 mL). The mixture is stirred for 1 h at ambient temperature then concentrated in vacuo to afford I-34 (230 mg, 99%) m/z 427.2 [M+H].

The following intermediates are prepared in similar fashion from the corresponding boronic ester or acid:

| Reagent Structure | | Intermediate | m/z |
|---|---|---|---|
| R-7 | 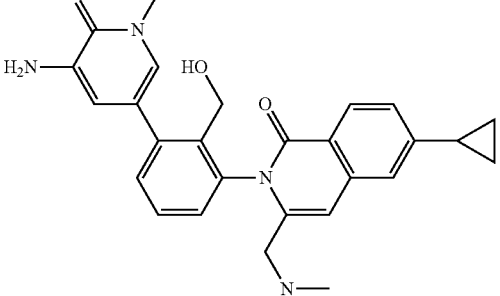 | I-35 | 457.2 |
| R-9 | 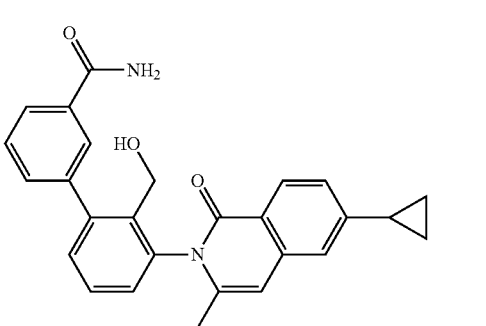 | I-36 | 454.2 |
Method 10
Synthesis of Intermediate I-39
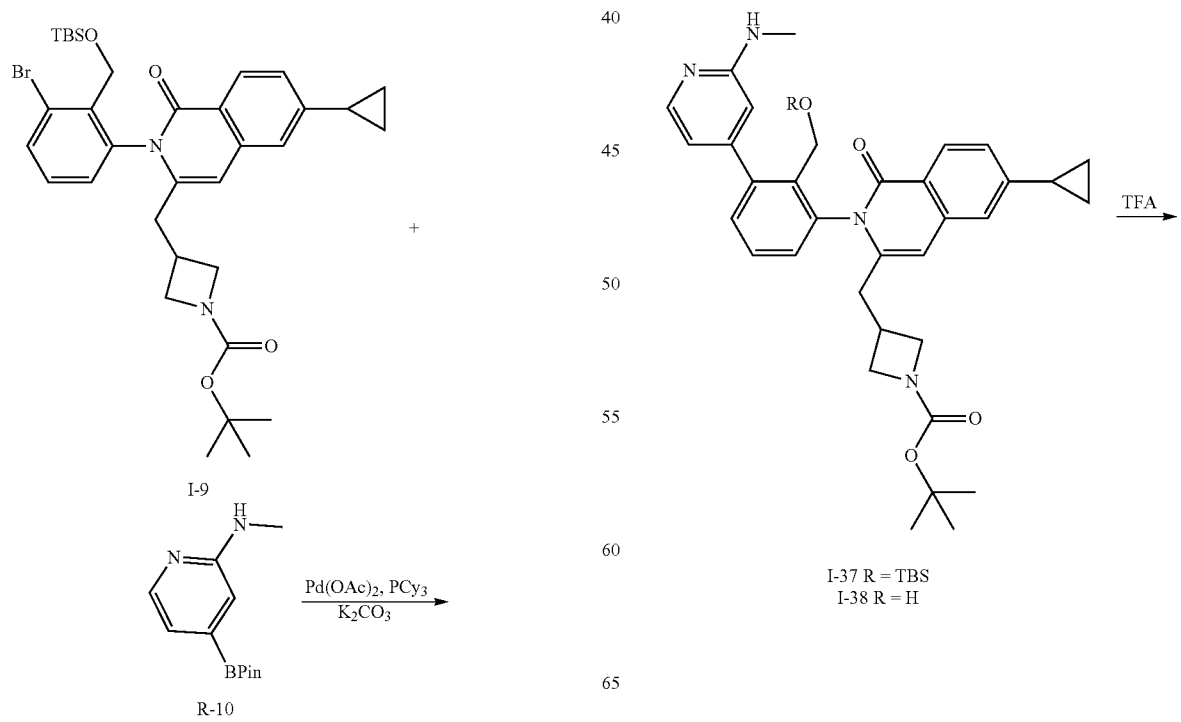
I-37 R = TBS
I-38 R = H

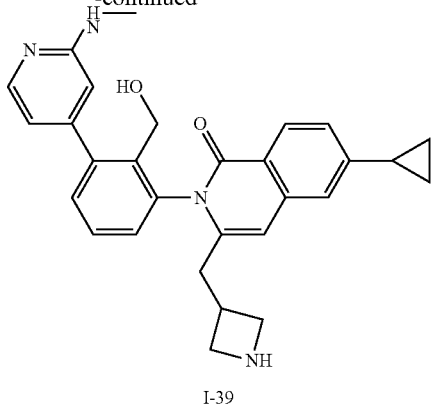

I-39

To a solution of I-9 (800 mg, 1.2 mmol), R-10 (430 mg, 1.8 mmol), tricyclohexylphosphine (100 mg, 0.37 mmol), and potassium carbonate (340 mg, 2.5 mmol) in DME (8 mL) and water (2 mL) is added palladium acetate (38 mg, 0.17 mmol). The mixture is heated at 100° C. for 1 h then cooled to ambient temperature and triturated with water (15 mL). The solid is filtered, rinsed with water (10 mL), collected and dried then purified by flash chromatography (SiO₂, EtOAc) to give I-37 (350 mg, 42%) m/z 681.4 [M+H] and I-38 (200 mg, 29%) m/z 567.3 [M+H].

The isolated mixture of both I-37 (280 mg) and I-38 (185 mg) is dissolved in TFA (5 mL) and stirred for 3 h at ambient temperature then concentrated in vacuo. The residue is dissolved in CH₂Cl₂, washed with 1M aqueous NaOH, organics collected and concentrated to afford I-39 (130 mg, 35%) m/z 467.2 [M+H].

The following intermediates are prepared in similar fashion from the corresponding boronic ester:

Method 11

Synthesis of Intermediate I-42

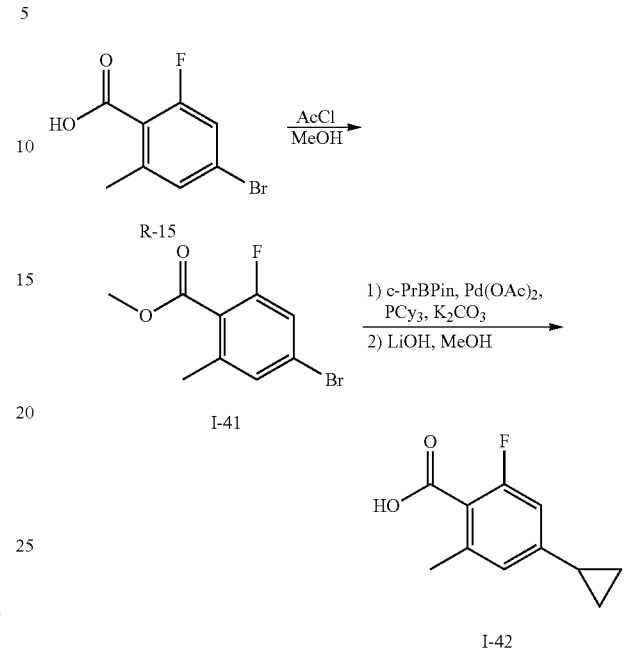

To a solution of R-15 (10 g, 43 mmol) in MeOH (200 mL) is added acetyl chloride (30 mL). The solution is stirred at ambient temperature for 1 day then treated with acetyl chloride (15 mL) and stirred at 55° C. for 2 days. The volatiles are removed in vacuo then residue is dissolved in EtOAc, washed with saturated aqueous sodium bicarbonate to give I-41 (10 g, 99%) nik 249.5 [M+H].

Ester I-41 (10 g, 40 mmol), c-PrBPin (10.2 g, 61 mmol), palladium acetate (1.4 g, 6.1 mmol), tricyclohexylphosphine (1.7 g, 6.1 mmol) and potassium carbonate (17 g, 121 mmol) in DME (400 mL) and water (100 mL) is heated at 120° C. for 16 h. The mixture is cooled to ambient temperature, diluted with EtOAc, washed with brine, dried over sodium sulfate, filtered and concentrated. The residue is purified by flash chromatography (SiO₂, Hep to 50% EtOAc in Hep) to give a residue that is dissolved in MeOH (100 mL) and treated with 2M aqueous NaOH (55 mL). The mixture is heated at 80° C. for 1 h then organics are removed in vacuo

| Reagent | Structure | Intermediate | m/z |
|---|---|---|---|
| R-13 | 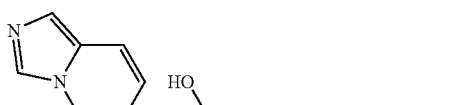 | I-40 | 477.3 | and treated with 1M aqueous HCl. The solid is filtered, washed with water, collected and dried to give I-42 (5.2 g, 66%) nik 195.0 [M+H]

Method 12

Synthesis of I-44

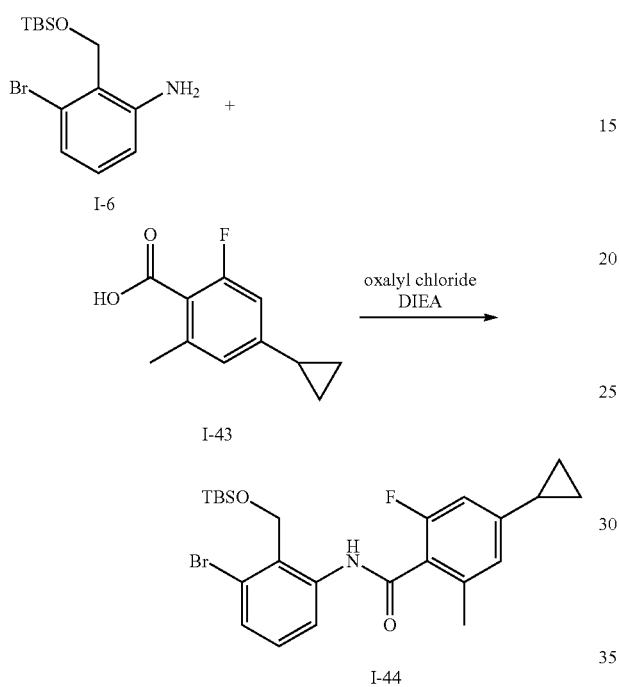

I-6

I-43

I-44

Acid I-42 (775 mg, 3.99 mmol) is dissolved in CH$_2$Cl$_2$ (10 mL) and treated with DMF (0.1 mL) then cooled to 0° C. and oxalyl chloride (0.41 mL, 4.79 mmol) is added. The mixture is stirred for 2 h then volatiles are removed in vacuo. The residue is dissolved in CH$_2$Cl$_2$ (10 mL) and treated with I-6 (1.26 g, 3.99 mmol) and DIEA (2.1 mL). The mixture is stirred for 14 h then volatiles are removed in vacuo, diluted with EtOAc, washed with water and brine, dried over sodium sulfate, filtered and concentrated. The residue is purified by flash chromatography (SiO$_2$, 0-50% EtOAc in Hep) to give I-43 (1.50 g, 76%) m/z 494.2 [M+H].

Method 13

Synthesis of I-45

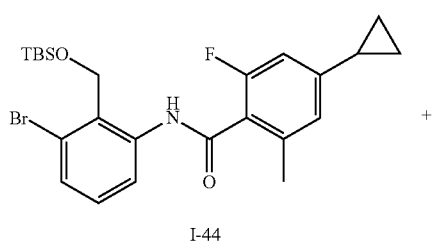

I-44

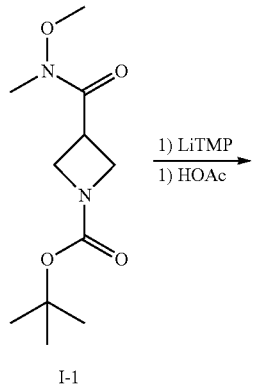

I-1

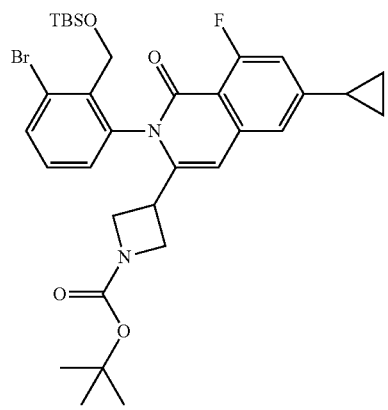

I-45

A solution of TMP (0.66 mL, 3.9 mmol) in THF (3 mL) is cooled to −15° C. and treated with a 2.5M n-BuLi solution in heptane (1.25 mL). The mixture is stirred for 10 min then a solution of I-44 (640 mg, 1.3 mmol) in THF (3 mL) is added dropwise. The mixture is stirred at −20° C. for 30 min then treated with a solution of I-1 (635 mg, 2.6 mmol) in THF (4 mL). The mixture is allowed to warm to ambient temperature and stirred for 1 h. The mixture is treated with saturated aq NH$_4$Cl, extracted with EtOAc, washed with brine, dried over Na$_2$SO$_4$, filtered and concentrated. The residue is dissolved in acetic acid (15 mL) and heated at 85° C. for 3 h then concentrated in vacuo, diluted with EtOAc, washed with aqueous saturated bicarbonate, dried over sodium sulfate, filtered and concentrated to afford a residue that is purified by flash chromatography (SiO$_2$, Hep to 70% EtOAc in Hep) to afford I-45 (440 mg, 52%) m/z 659.3 [M+H].

The following intermediates are prepared in similar fashion from I-2:

| Structure | Intermediate | m/z |
|---|---|---|
| 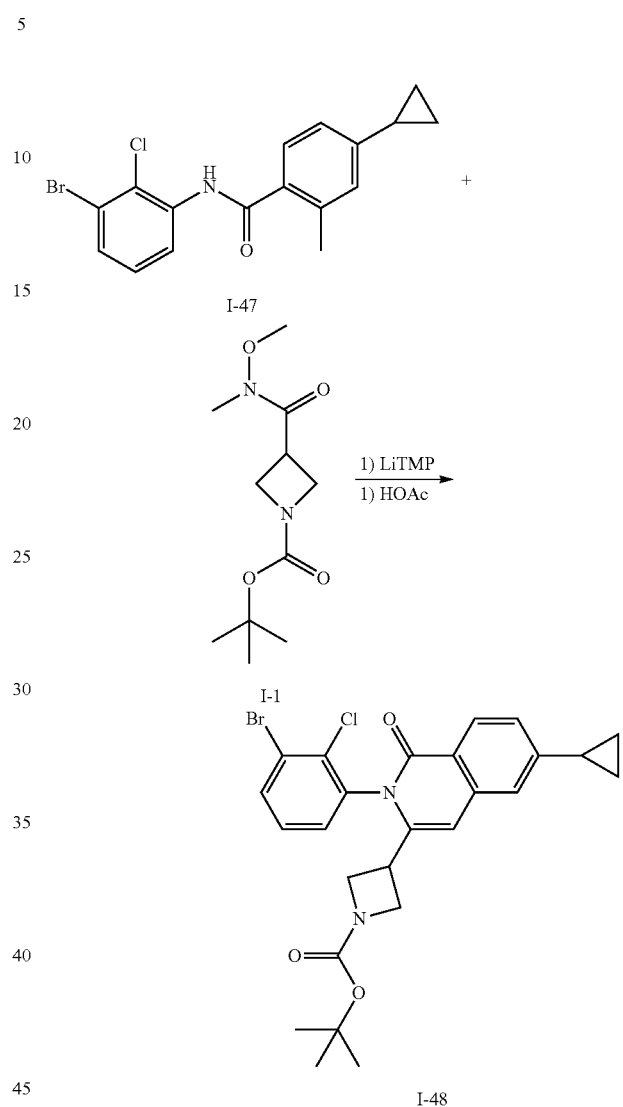 | I-46 | 657.3 [M + H] |

Method 14

Synthesis of I-47

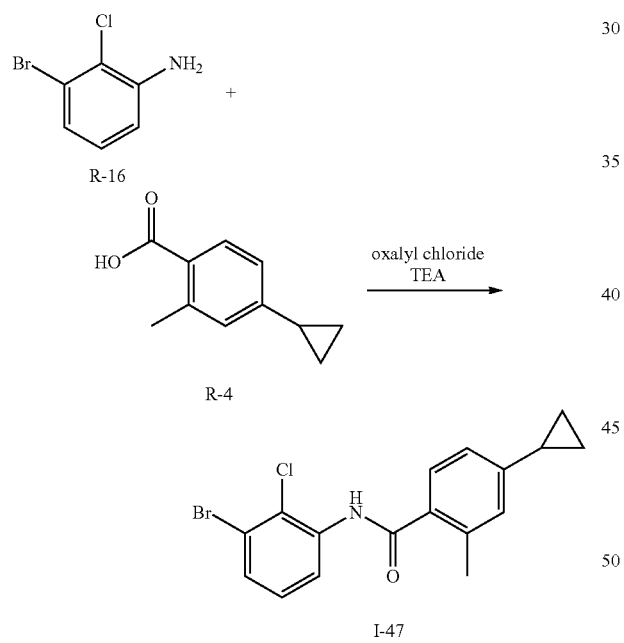

Acid R-4 (7.5 g, 43 mmol) is dissolved in CH₂Cl₂ (200 mL) and treated with DMF (1.0 mL) then cooled to 0° C. and oxalyl chloride (4.3 mL, 51 mmol) is added. The mixture is stirred for 2 h then volatiles are removed in vacuo. The residue is dissolved in CH₂Cl₂ (100 mL) and treated with R-16 (8.8 g, 43 mmol) and TEA (17 mL). The mixture is stirred for 14 h then volatiles are removed in vacuo, diluted with EtOAc, washed with water and brine, dried over sodium sulfate, filtered and concentrated. The residue is purified by flash chromatography (SiO₂, 6% EtOAc in Hep) to give I-47 (8.4 g, 54%) m/z 366.1 [M+H].

Method 15

Synthesis of I-48

A solution of TMP (4.7 mL, 27 mmol) in THF (70 mL) is cooled to −20° C. and treated with a 2.7M n-BuLi solution in heptane (9.1 mL). The mixture is stirred for 10 min then a solution of I-47 (2.0 g, 5.5 mmol) in THF (10 mL) is added dropwise. The mixture is stirred at −20° C. for 30 min then treated with a solution of I-1 (2.7 g, 11 mmol) in THF (10 mL). The mixture is allowed to warm to ambient temperature and stirred for 1 h. The mixture is treated with saturated aq NH₄Cl, extracted with EtOAc, washed with brine, dried over Na₂SO₄, filtered and concentrated. The residue is dissolved in acetic acid (50 mL) and heated at 85° C. for 3 h then concentrated in vacuo, diluted with EtOAc, washed with aqueous saturated bicarbonate, dried over sodium sulfate, filtered and concentrated to afford a residue that is purified by flash chromatography (SiO₂, Hep to 20% EtOAc in Hep) to afford I-48 (0.95 g, 33%) m/z 531.1 [M+H].

Method 16

Synthesis of I-51

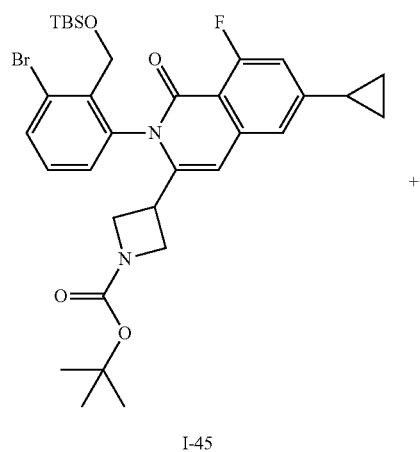

I-45

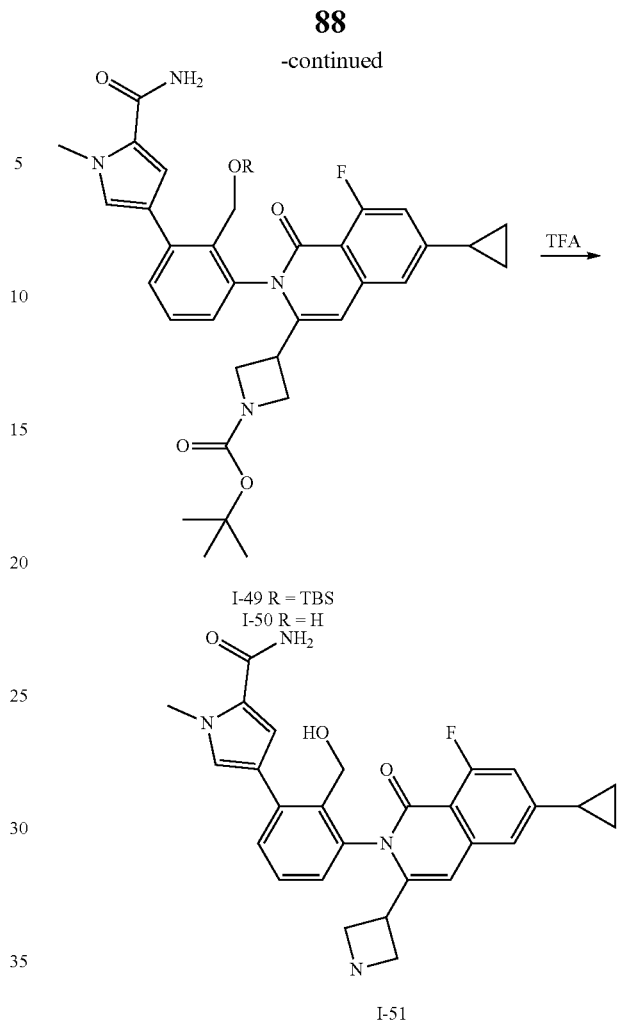

I-49 R = TBS
I-50 R = H

I-51

To a solution of I-45 (120 mg, 0.18 mmol), R-5 (68 mg, 0.27 mmol), tricyclohexylphosphine (15 mg, 0.055 mmol), and potassium carbonate (50 mg, 0.37 mmol) in DME (5 mL) and water (2 mL) is added palladium acetate (6 mg, 0.026 mmol). The mixture is heated at 100° C. for 1.5 h then cooled to ambient temperature and triturated with water (10 mL). The solid is filtered, rinsed with water (10 mL), collected and dried then purified by flash chromatography ($SiO_2$, EtOAc) to give I-49 (52 mg, 41%) m/z 701.4 [M+H] and I-50 (18 mg, 17%) m/z 587.2 [M+H].

A solution of I-49 (52 mg) and I-50 (18 mg) in TFA (5 mL) is stirred for 1 h at ambient temperature. The volatiles are removed in vacuo, dissolved in EtOAc (15 mL) and treated with potassium carbonate (100 mg) in water (10 mL). The mixture is stirred overnight then layers are separated. The aqueous is extracted with EtOAc and all organics are combined and concentrated in vacuo to afford I-51 (48 mg, 99%) m/z 487.1 [M+H].

The following intermediate are prepared in similar fashion from the corresponding bromo intermediate:

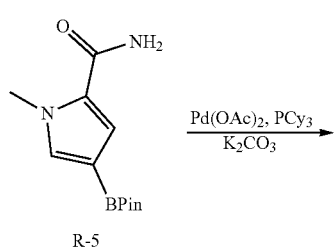

R-5

| Bromo Intermediate | Structure | Intermediate | m/z |
|---|---|---|---|
| I-46 | 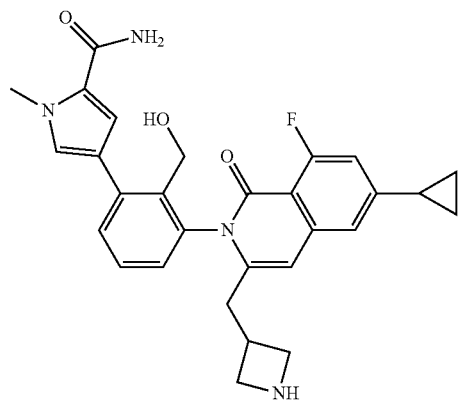 [SMILES: Cn1cc(-c2cccc(-n3c(CC4CNC4)cc4cc(C5CC5)cc(F)c4c3=O)c2CO)cc1C(N)=O] | I-52 | 501.3 [M + H] |

Method 17

Synthesis of I-54

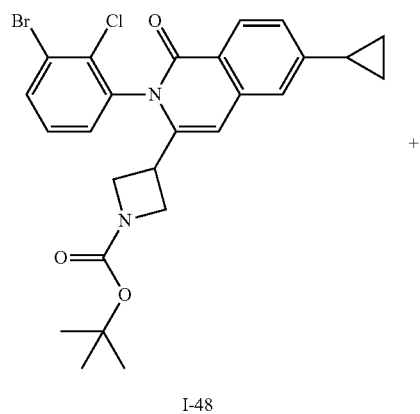

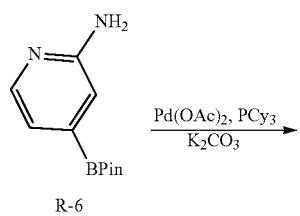

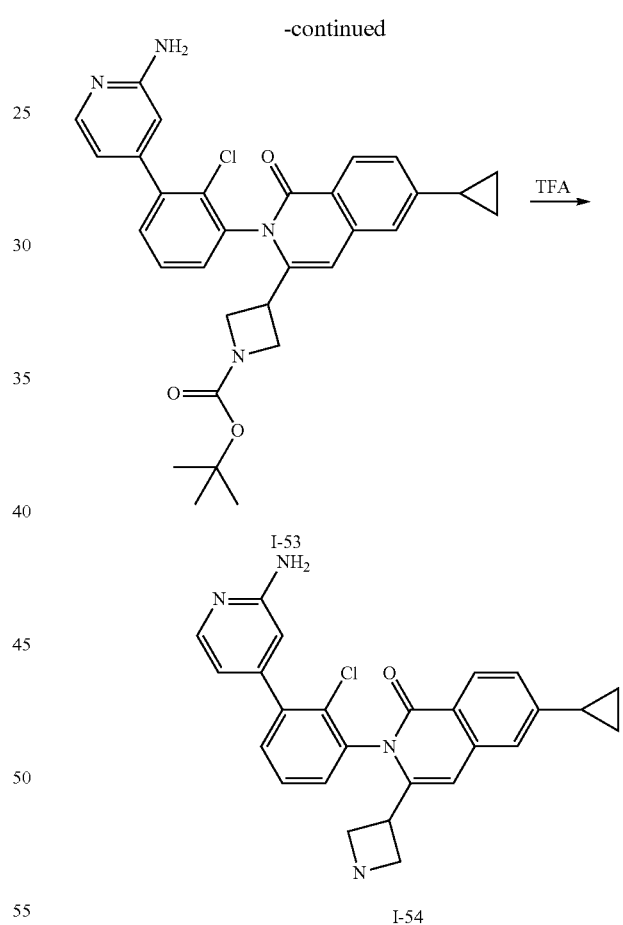

To a solution of I-48 (450 mg, 0.85 mmol), R-6 (374 mg, 1.7 mmol), tricyclohexylphosphine (48 mg, 0.17 mmol), and potassium carbonate (350 mg, 2.5 mmol) in DME (12 mL) and water (3 mL) is added palladium acetate (19 mg, 0.085 mmol). The mixture is heated at 100° C. for 1.5 h then volatiles are removed in vacuo. The residue is extracted with EtOAc, washed with water, brine, dried over sodium sulfate, filtered and concentrated. The residue is purified by flash chromatography (SiO$_2$, 0-5% MeOH in CH$_2$Cl$_2$) to give I-53 (140 mg, 30%) m/z 543.3 [M+H].

A solution of I-53 (140 mg) in CH$_2$Cl$_2$ (1 mL) is treated with TFA (2 mL) and is stirred for 1 h at ambient temperature. The volatiles are removed in vacuo and residue is extracted with CH$_2$Cl$_2$, washed with 1M aqueous NaOH, dried over sodium sulfate, filtered and concentrated in vacuo to afford I-54 (100 mg, 88%) m/z 443.01 [M+H].

Method 18

Synthesis of Example 1

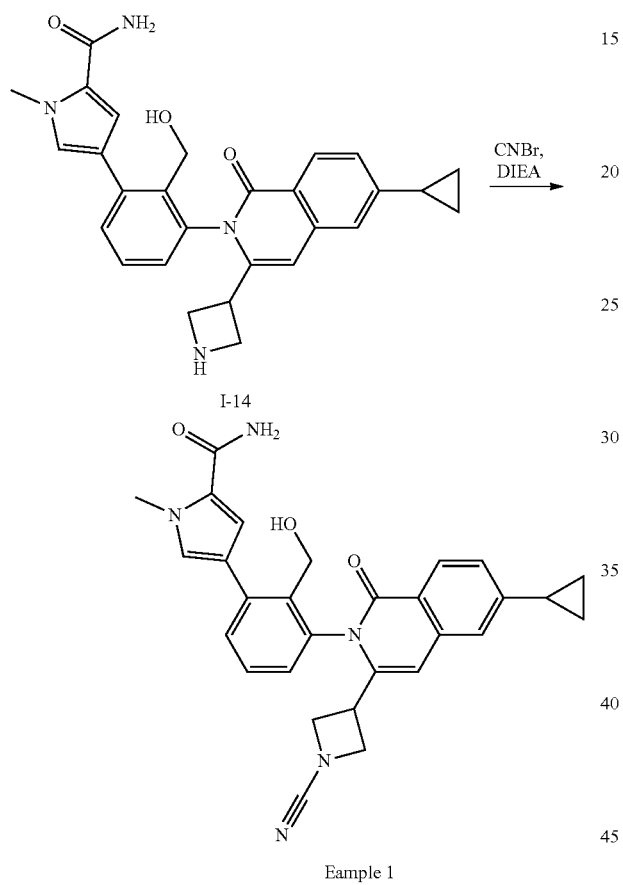

Eample 1

To a solution of I-14 (75 mg, 0.16 mmol) in CH$_2$Cl$_2$ (2 mL) is added DIEA (0.9 mL, 0.48 mmol) and CNBr (0.5 mL, 0.15 mmol). The mixture is stirred for 2 h then directly purified by RHPLC to afford Example 1 (18 mg, 23%).

The following compounds are prepared in similar fashion from the corresponding amine intermediates

| Example | Amine Intermediate |
|---|---|
| 3 | I-17 |
| 4 | I-18 |
| 9 | I-16 |
| 12 | I-21 |
| 31 | I-30 |
| 32 | I-35 |

Method 19

Synthesis of Example 7

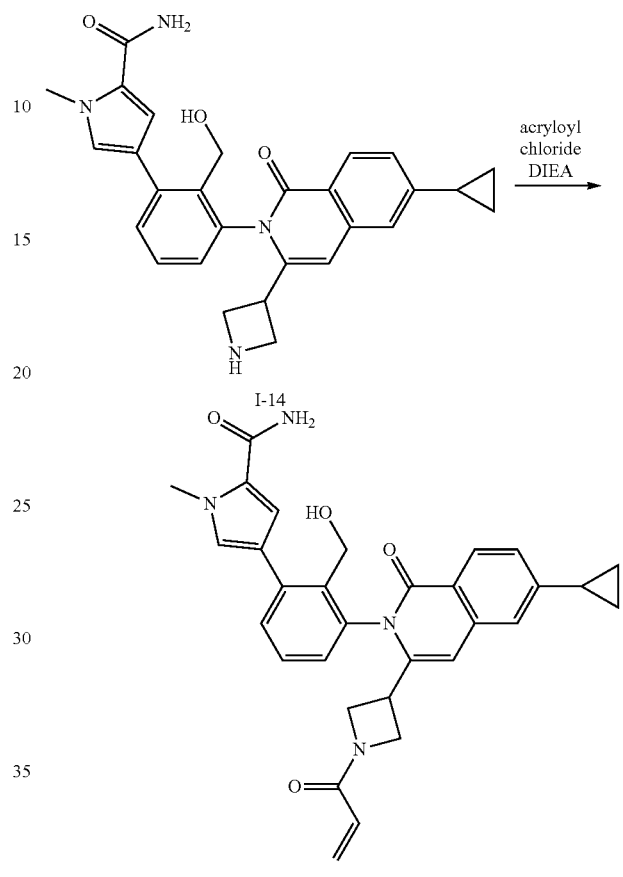

Eample 7

A solution of I-14 (4.5 g, 7.7 mmol) in CH$_2$Cl$_2$ (30 mL) is treated with DIEA (2.7 mL, 15 mmol) followed by acryloyl chloride (0.53 mL, 6.5 mmol). The mixture is stirred for 0.5 h then diluted with EtOAc (100 mL), washed with saturated aqueous ammonium chloride, brine, dried over sodium sulfate, filtered and concentrated. The residue is purified by flash chromatography (SiO$_2$, 0-5% MeOH in EtOAc) to give a residue that is triturated with EtOAc to give a solid that is filtered, collected, and dried to afford Example 7 (2.6 g, 66%).

The following compounds are prepared in similar fashion from the corresponding amine intermediates

| Example | Amine Intermediate |
|---|---|
| 2 | I-25 |
| 5 | I-18 |
| 6 | I-26 |
| 10 | I-17 |
| 11 | I-16 |
| 13 | I-27 |
| 14 | I-22 |
| 15 | I-19 |
| 16 | I-30 |
| 17 | I-15 |
| 18 | I-28 |

-continued

| Example | Amine Intermediate |
|---|---|
| 20 | I-54 |
| 21 | I-21 |
| 22 | I-31 |
| 23 | I-34 |
| 24 | I-35 |
| 25 | I-32 |
| 26 | I-14 |
| 27 | I-40 |
| 29 | I-19 |
| 33 | I-39 |
| 36 | I-36 |
| 37 | I-33 |

Method 20

Synthesis of Example 19

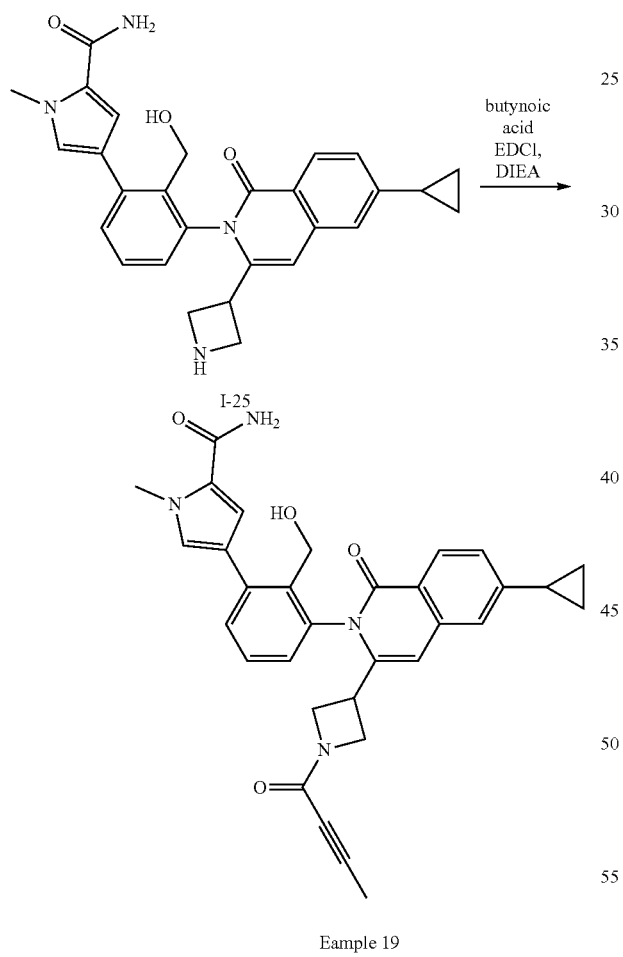

Example 19

To a solution of I-25 (75 mg, 0.16 mmol), butynoic acid (12 mg, 0.14 mmol), and EDCI (46 mg, 0.24 mmol) in DMF (1 mL) is added DIEA (110 µL). The mixture is stirred at ambient temperature for 2 h then purified by RHPLC to give Example 19 (14 mg, 16%).

The following compounds are prepared in similar fashion from the corresponding amine intermediates

| Example | Amine Intermediate |
|---|---|
| 8 | I-25 |
| 28 | I-16 |
| 30 | I-17 |
| 34 | I-28 |
| 35 | I-19 |
| 39 | I-26 |

Method 21

Synthesis of Example 40

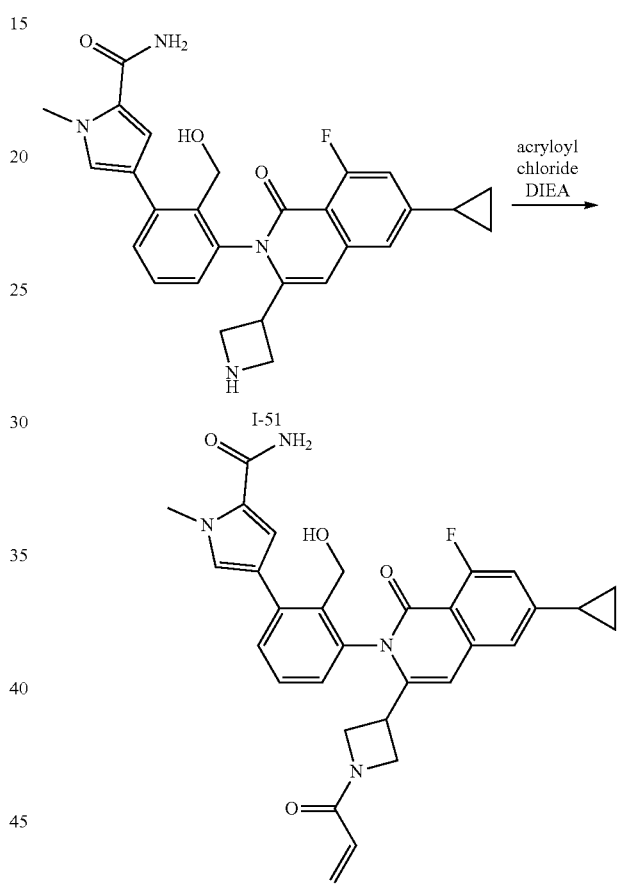

Example 40

A solution of I-51 (40 mg, 0.082 mmol) in $CH_2Cl_2$ (2 mL) is treated with DIEA (30 µL, 0.16 mmol) followed by acryloyl chloride (6 µL, 0.070 mmol). The mixture is stirred for 0.5 h then diluted with EtOAc (10 mL), washed with saturated aqueous ammonium chloride, brine, dried over sodium sulfate, filtered and concentrated. The residue is purified by flash chromatography ($SiO_2$, 0-5% MeOH in EtOAc) to afford Example 40 (24 mg, 54%).

The following compounds are prepared in similar fashion from the corresponding amine intermediates

| Example | Amine Intermediate |
|---|---|
| 38 | I-52 |
| 41 | I-52 |

Method 22

Resolution of Example 7 to Provide Examples 42 and 43

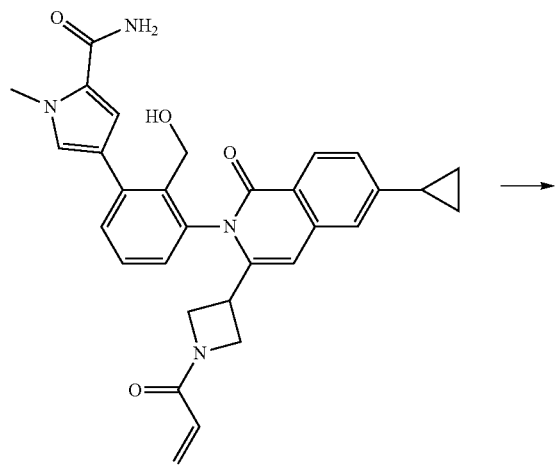

Example 7

Example 42 and 43

Example 7 (100 mg, 190 mmol) is separated on ChromegaChiral CCS (ES Indutries, 5 micron, 250×30 mm, gradient: 35% MeOH (4 mM ammonia):acetonitrile in supercritical carbon dioxide for 15 min at 80 g/min, temperature 40° C., pressure 140 bar) to give 39 mg of Example 42 (retention time 10.0 min) and 41 mg of Example 43 (retention time 13.1 min).

Description of Biological Properties

BTK v. EGFR Inhibition Assay

BTK Lanthscreen® Eu Kinase Binding assay:

A Lanthscreen® Eu Kinase Binding assay (Life Technologies) was performed to quantitate the ability of test compounds to bind to BTK. The assay is based on the binding and displacement of Alexa Fluor647-labeled Kinase Tracer #236 to the ATP-binding site of human full length His-tagged BTK (Life Technologies cat # PV3587) with TR-FRET detection using a europium-labeled anti-His antibody. The assay was assembled in 384-well low volume NBS black plates (Corning) where 2 nM BTK and test compound in DMSO at varying concentrations were pre-incubated for 30 min at 28° C. in assay buffer consisting of 50 mM HEPES, pH 7.4, 10 mM $MgCl_2$, 1 mM EGTA. 100 µM $Na_3VO_4$ and 0.01% Brij 35. Then, 2 nM of Eu-anti His antibody and 30 nM Kinase Tracer were added and incubated for 60 mM at 28° C. Following incubation, TR-FRET signal was read on an Envision plate reader (Excitation: 340 nm; Emissions: 615 and 665 nm). The 665: 615 nm emission ratio was calculated and converted to POC compared to control and blank wells.

Inhibition of IL-6 Production in B Cells Co-Stimulated with ODN 2006 and Anti-hIgD Primary CD19+ B cells (AllCells # PB010F) are thawed and plated in RPMI containing 10% HI FBS in a 384-well tissue cultured plate at 20,000 cells/well. The cells are treated with test compound (0.5% DMSO final concentration) and incubated for 1 hour at 37° C., 5% CO2. Cells are then stimulated with 5 µg/mL Goat F(ab')2 anti-human IgD (SouthernBiotech #2032) and 2 uM ODN 2006 (InvivoGen # till-2006) and incubated for 18-24 hours at 37° C., 5% $CO_2$. IL-6 in the supernatant is measured using Meso Scale Discovery kit # K211AKB-6.

Inhibition of EGFR Autophosphorylation in A431 Human Epithelial Cells Stimulated with Epithelial Growth Factor A431 cells (ATCC # CRL-1555 FZ) are thawed and plated in DMEM containing 10% FBS in a 384-well tissue culture treated plate at 15,000 cells/well. After incubating for 24 hours at 37° C., 5% $CO_2$, the cells are treated with test compound (1% DMSO final concentration) and incubated for 16 hours at 37° C., 5% $CO_2$. EGF (Millipore, 01-107) is added at a final concentration of 60 ng/mL and incubated for 10 minutes. The medium is removed, the cells are lysed, and phospho EGFR is measured (Meso Scale Diagnostics, N31CB-1).

Preferred compounds of the present invention, which can be used for the treatment of autoimmune disorders, exhibited a highly selective BTK inhibition over other related kinases such as EGFR. The compounds described herein show a range of selectivity against EGFR as measured in cellular assays (BTK activity measured by IL-6 production in primary CD19+ cells; EGFR activity measured by EGFR phosphorylation in A431 cells). See Table II.

TABLE II

| Example | B-cell IL-6 $IC_{50}$ (nM) | A431 p-EGFR $IC_{50}$ (nM) |
| --- | --- | --- |
| 1 | 4.3 | 4700 |
| 2 | 36 | >10000 |
| 5 | 100 | >10000 |
| 6 | 16 | 4500 |
| 7 | 5.6 | >10000 |
| 8 | 96 | >10000 |
| 11 | 21 | >10000 |
| 12 | 28 | 4500 |
| 13 | 12 | >10000 |
| 14 | 85 | >10000 |
| 15 | 8.8 | >10000 |
| 16 | 92 | >10000 |
| 17 | 3.7 | >10000 |
| 18 | 160 | >10000 |
| 20 | 37 | 3200 |
| 21 | 1.9 | >10000 |
| 40 | 4.6 | >10000 |
| 43 | 3.6 | >10000 |

Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good inhibitory effect upon BTK.

Such diseases include for example: rheumatoid arthritis, systemic lupus erythromatosis, lupus nephritis, Sjogren's disease, vasculitis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis.

The compounds of formula (I) may be used on their own or in combination with at least one other active substance according to the invention, and/or optionally also in combination with at least one other pharmacologically active substance. The other pharmacologically active substance may be an immunomodulatory agent, anti-inflammatory agent, or a chemotherapeutic agent. Examples of such agents include but are not limited to cyclophosphamide, mycophenolate (MMF), hydroxychloroquine, glucocorticoids, corticosteroids, immunosuppressants, NSAIDs, non-specific and COX-2 specific cyclooxygenase enzyme inhibitors, tumour necrosis factor receptor (TNF) receptors antagonists and methotrexate.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

All patent and non-patent documents or literature cited in this application are herein incorporated by reference in their entirety.

The invention claimed is:

1. A compound of the formula (I):

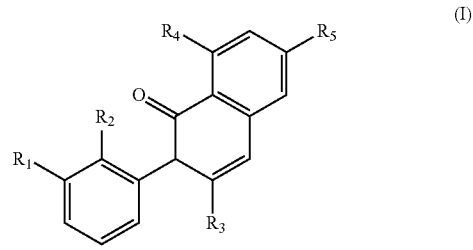

wherein $R_1$ is chosen from

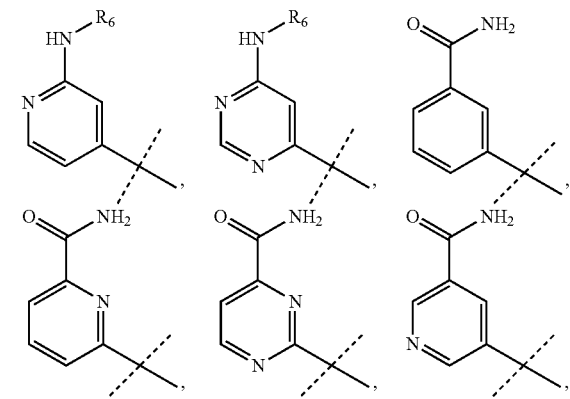

-continued

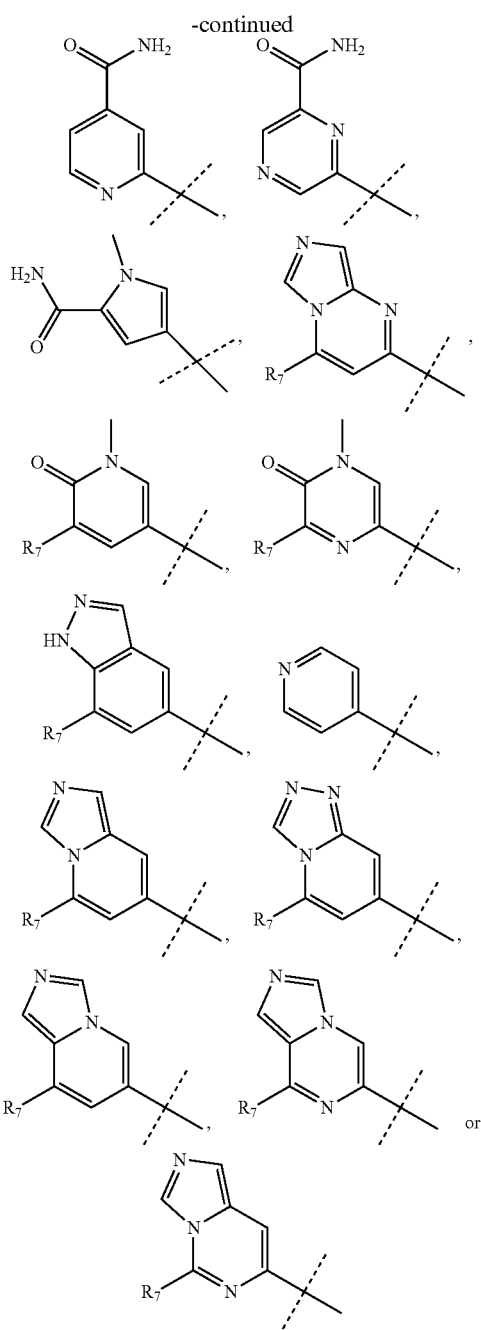

wherein R₆ is H or CH₃ and;
R₇ is H, NH₂, —NH—C₁₋₄ alkyl or —NH—C₃₋₄ cycloalkyl
R₂ is chosen from H, F, Cl, CH₃, or CH₂OH;
R₃ is chosen from;

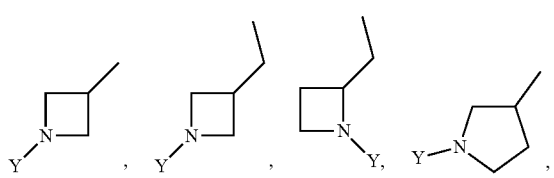

-continued

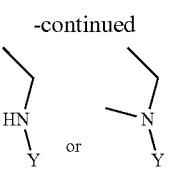

wherein Y is CN,

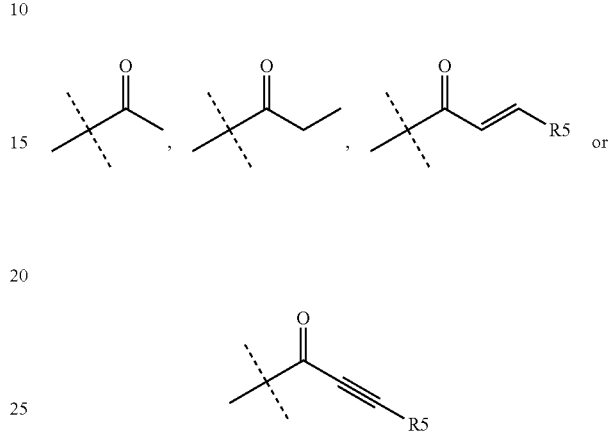

R₄ is chosen from H, F, Cl or OMe
each R₅ is independently chosen from H, C₁₋₄ alkyl, or C₃₋₄ cycloalkyl;
each group defined above for R₁-R₅ is, where possible, partially or fully halogentated.

2. The compound of the formula (I) according to claim 1, wherein R₁ is chosen from

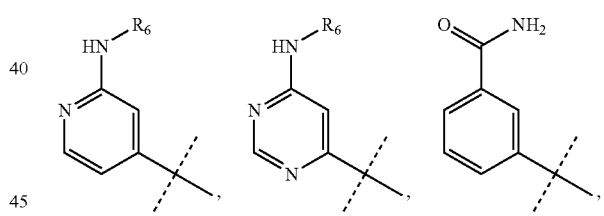

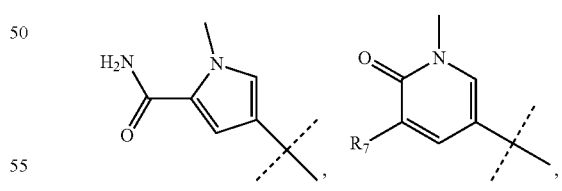

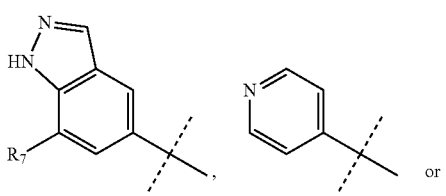

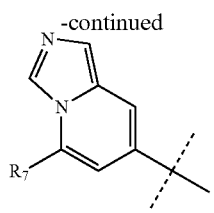

wherein R₆ is H or CH₃ and;
R₇ is H, NH₂, —NH—C₁₋₄ alkyl or —NH—C₃₋₄ cycloalkyl
R₂ is chosen from H, F, Cl, CH₃, or CH₂OH;
R₃ is chosen from;

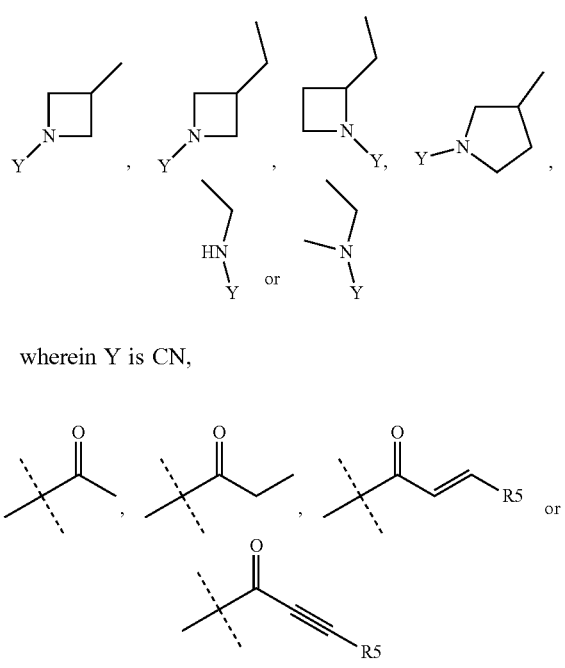

wherein Y is CN,

R₄ is chosen from H, F, Cl or OMe
each R₅ is independently chosen from H, C₁₋₄ alkyl, or C₃₋₄ cycloalkyl;
each group defined above for R₁-R₅ is, where possible, partially or fully halogentated.

3. The compound of the formula (I) according to claim 1, wherein R₁ is chosen from

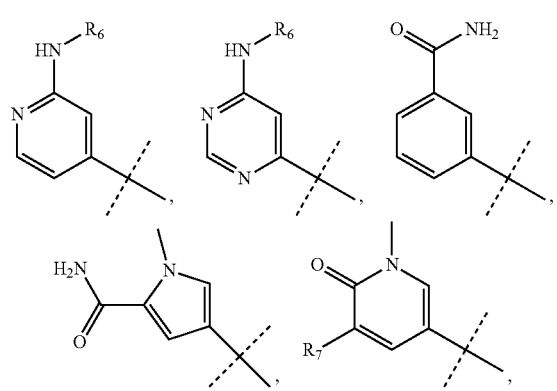

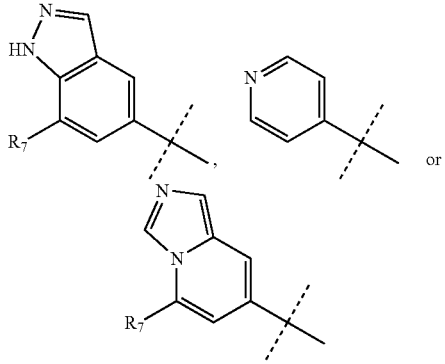

wherein R₆ is H or CH₃ and;
R₇ is H or NH₂
R₂ is chosen from H, F, Cl, CH₃ or CH₂OH;
R₃ is chosen from;

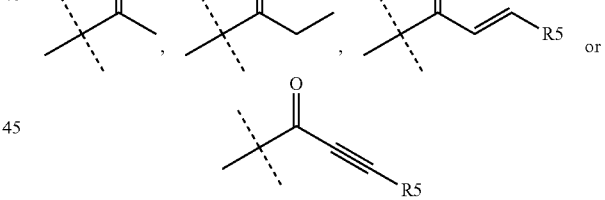

Wherein Y is CN,

R₄ is chosen from H, F, Cl or OMe
each R₅ is independently chosen from H, C₁₋₄ alkyl, or C₃₋₄ cycloalkyl;
each group defined above for R₁-R₅ is, where possible, partially or fully halogentated.

4. The compound of the formula (I) according to claim 1, wherein R₁ is chosen from

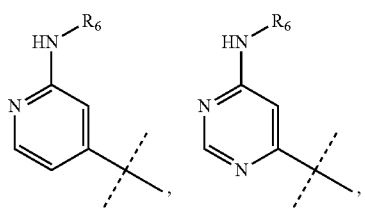

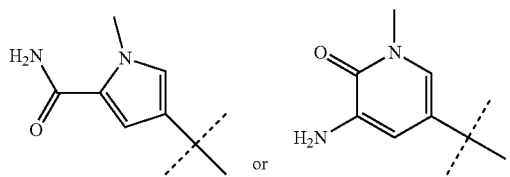
wherein $R_6$ is H or $CH_3$ and;
$R_2$ is $CH_2OH$;
$R_3$ is chosen from;
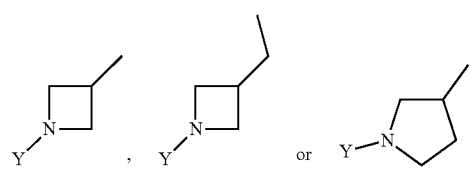
wherein Y is
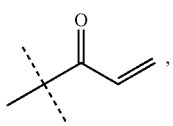
$R_4$ is chosen from H or F
each $R_5$ is independently chosen from H, $C_{1-4}$ alkyl, or $C_{3-4}$ cycloalkyl;
each group defined above for $R_1$-$R_5$ is, where possible, partially or fully halogentated.
5. A compound chosen from any of the compounds shown in the following table:
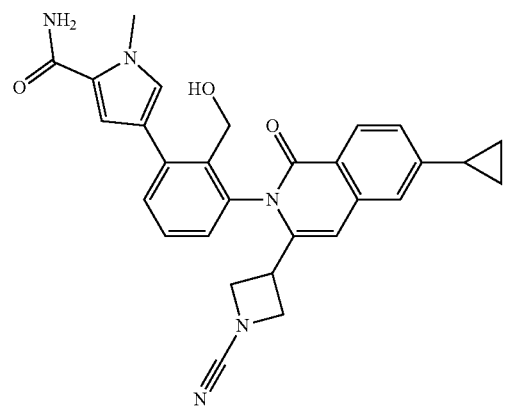
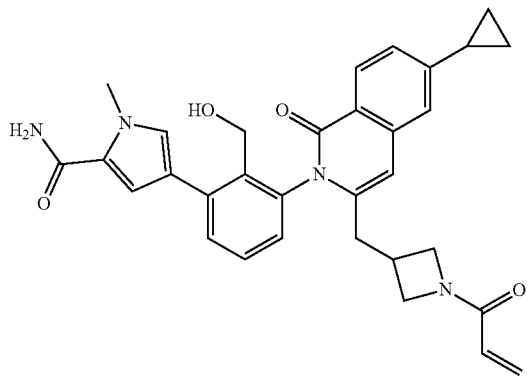
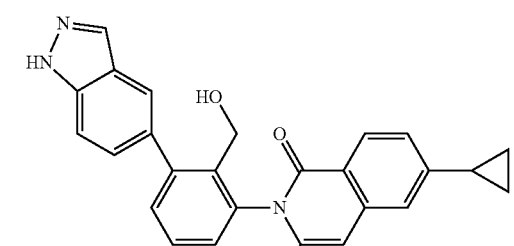
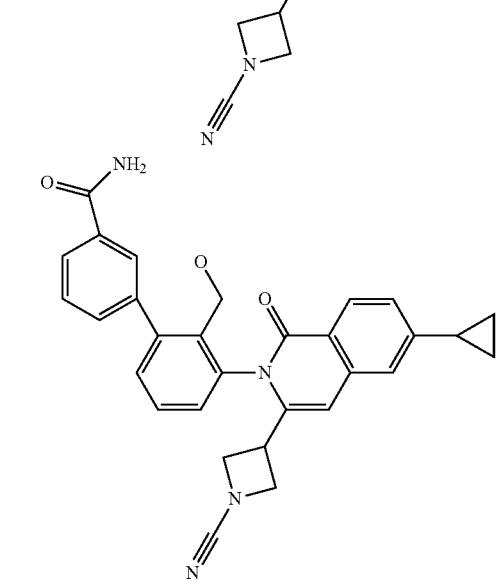
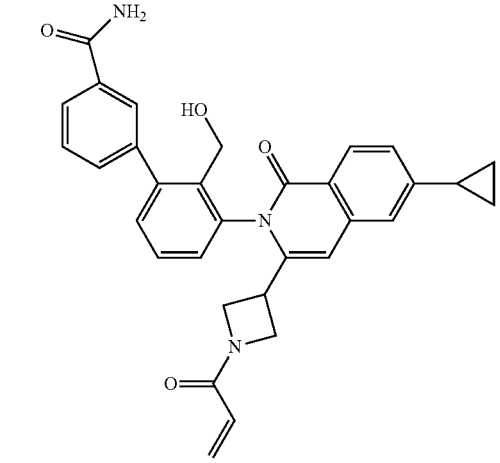

105
-continued
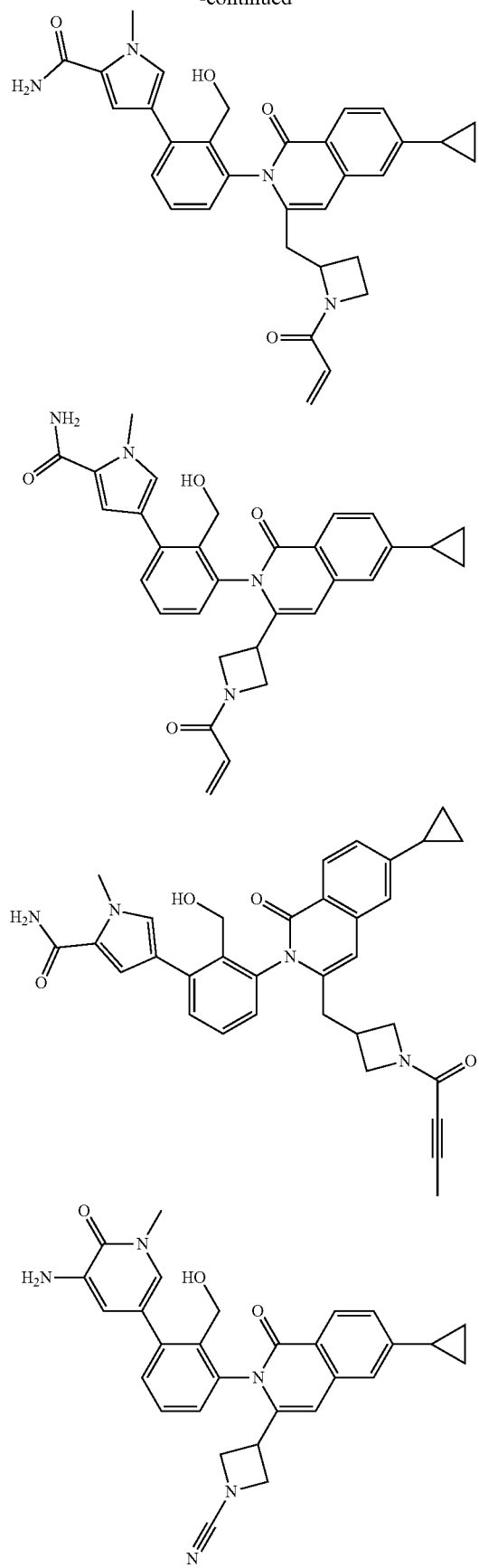
106
-continued
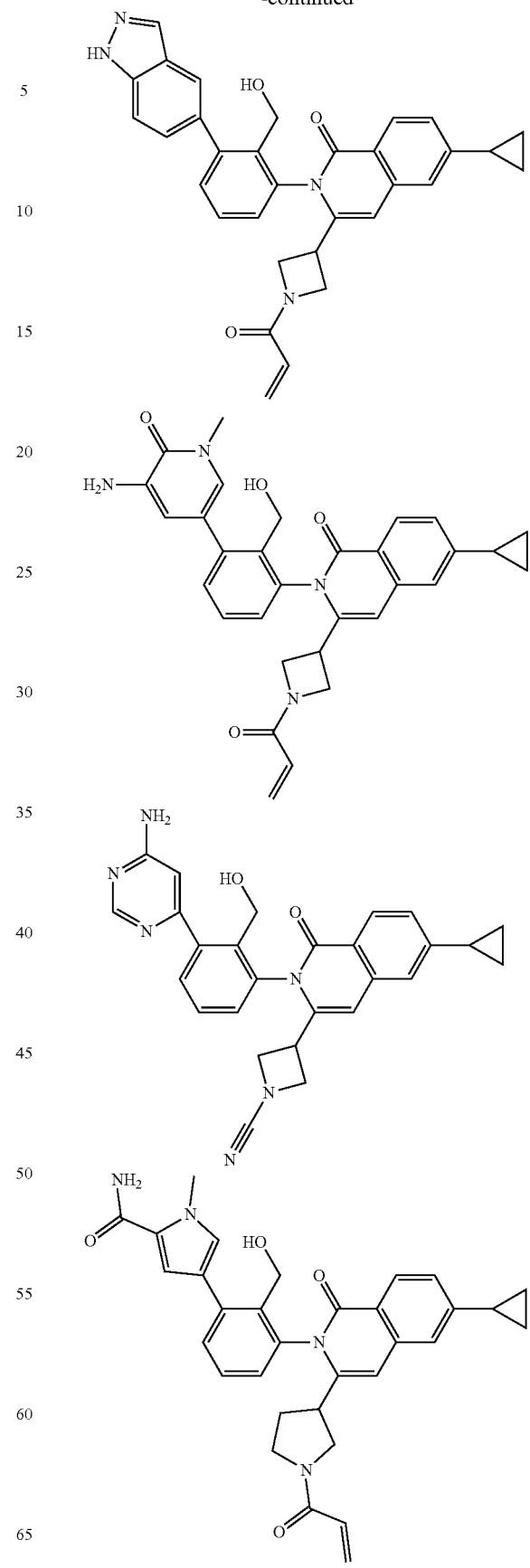

107
-continued
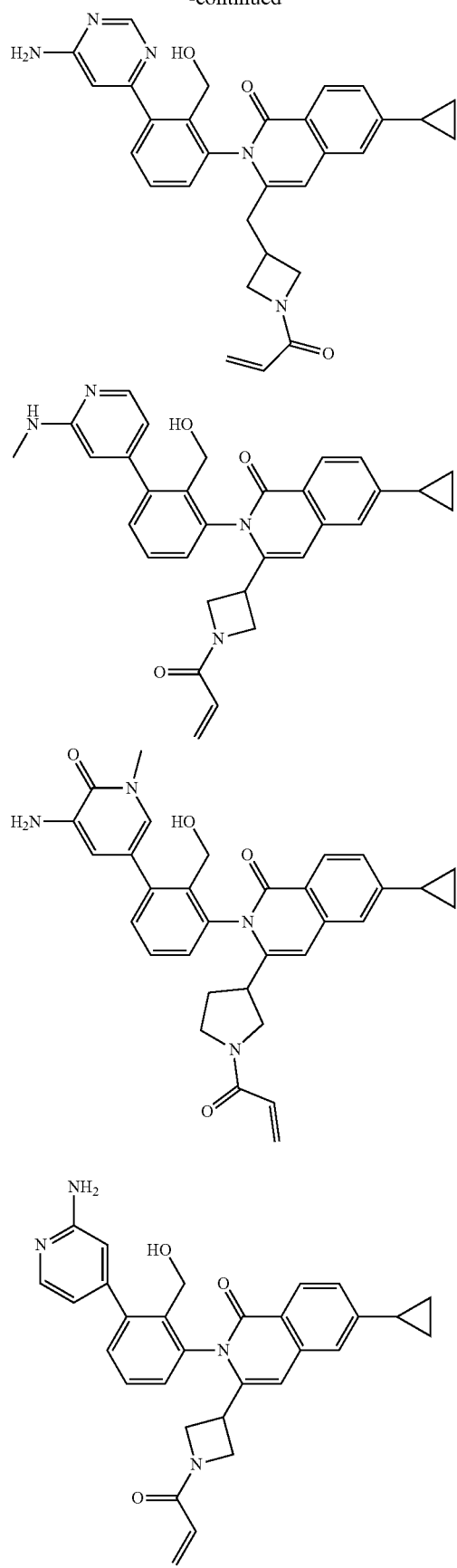
108
-continued
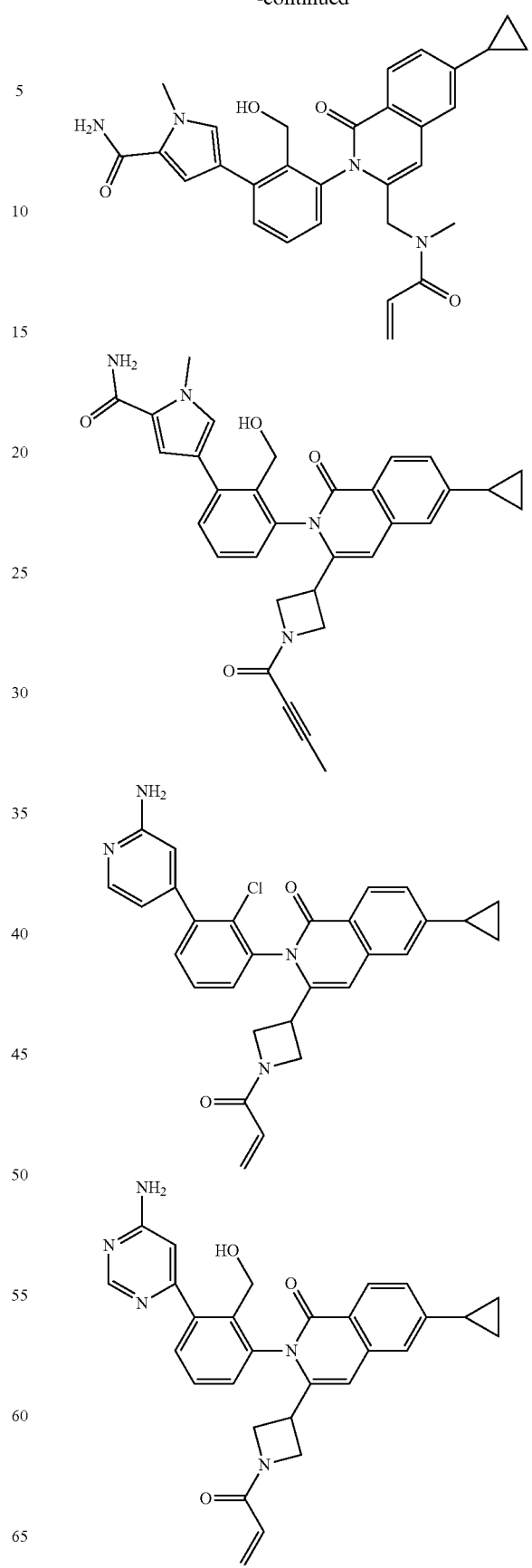

109
-continued
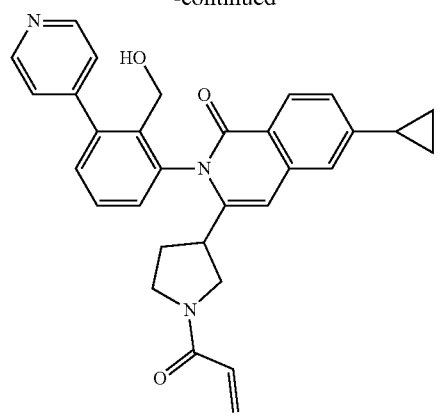
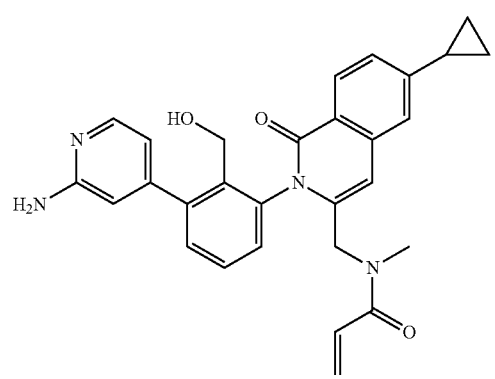
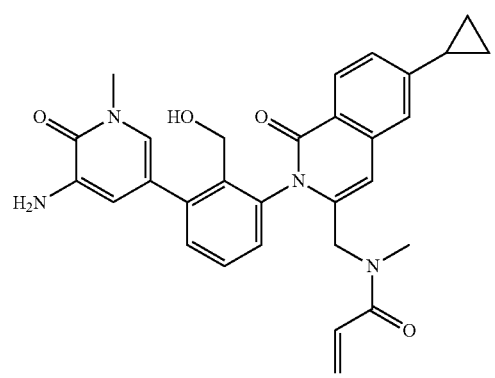
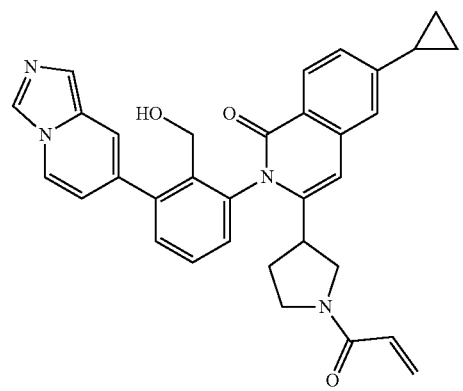
110
-continued
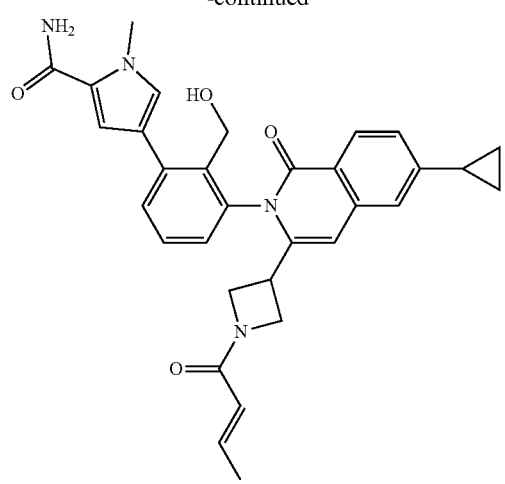
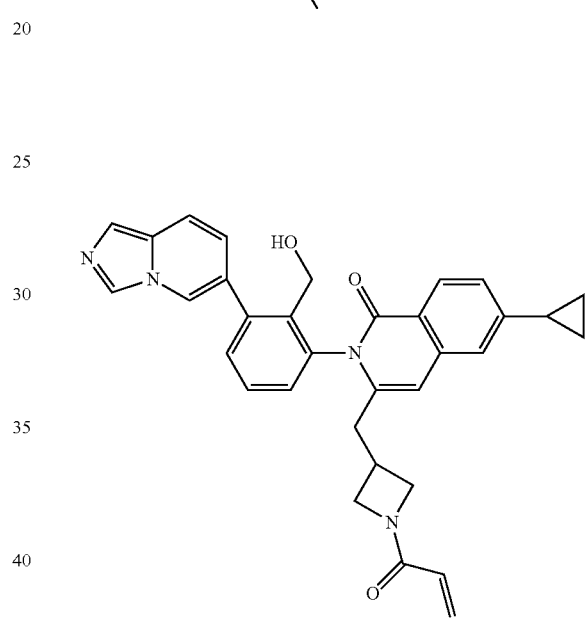
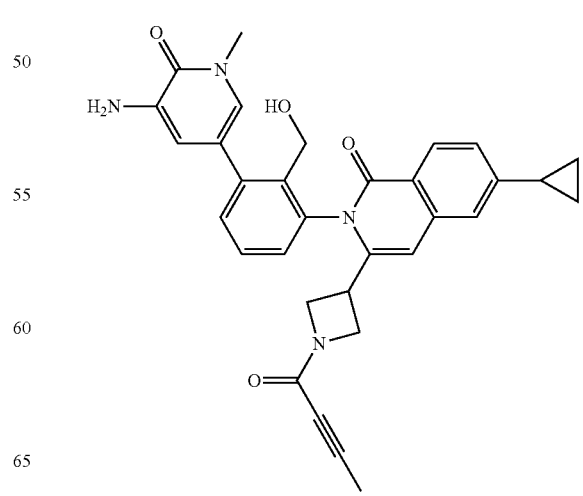

111
-continued
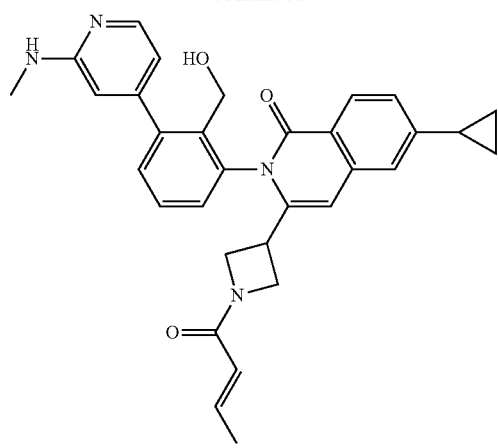
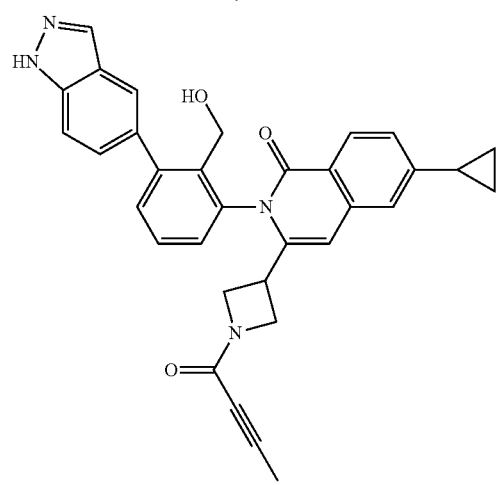
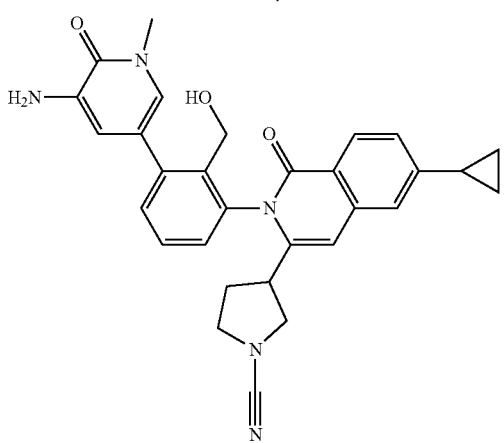
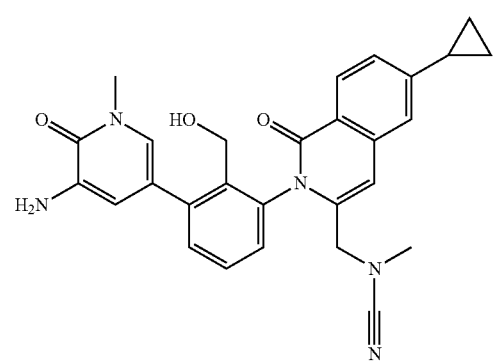
112
-continued
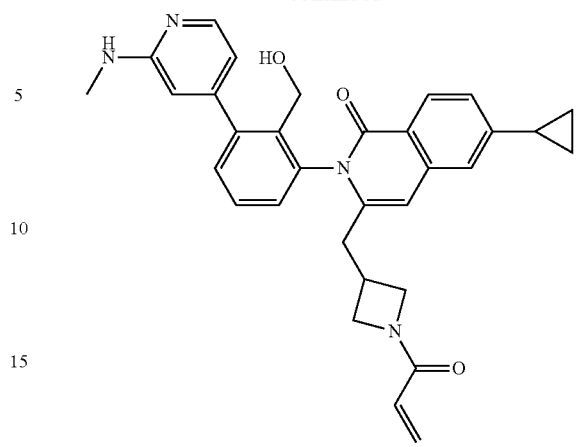
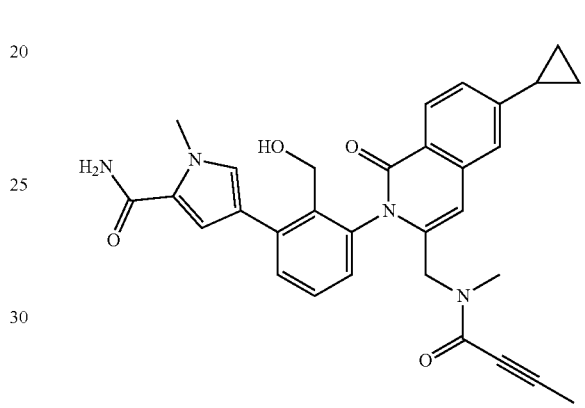
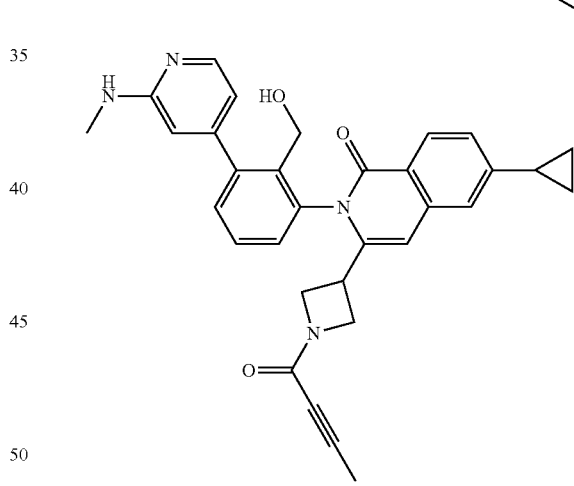
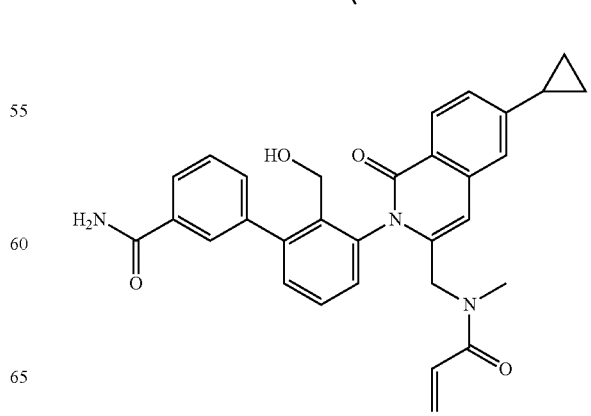

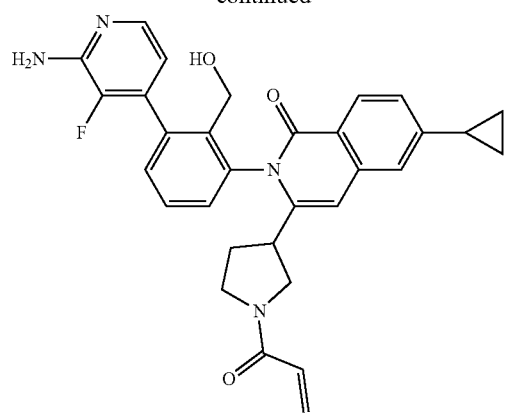
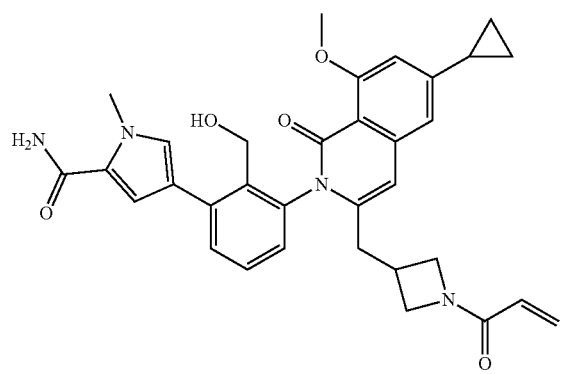
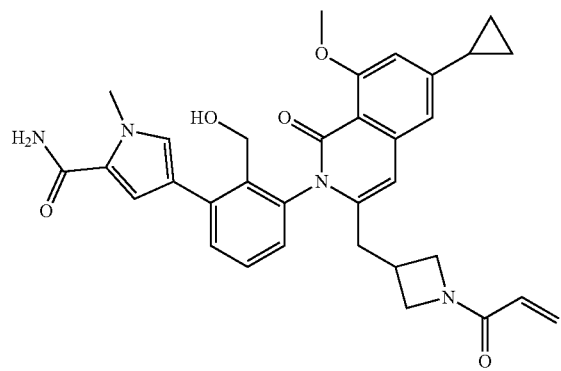
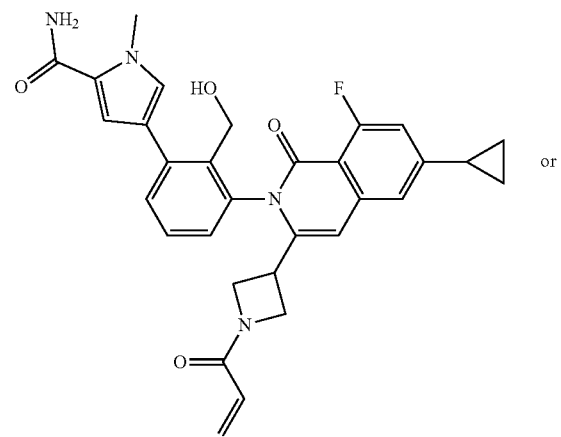
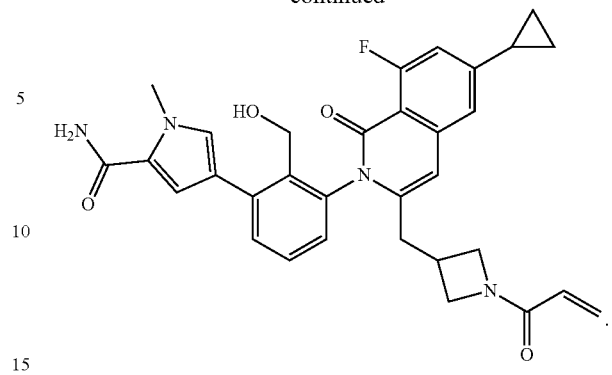
6. A pharmaceutical composition comprising a therapeutically effective amount of a compound according to claim 1.
7. A compound of the formula (I):
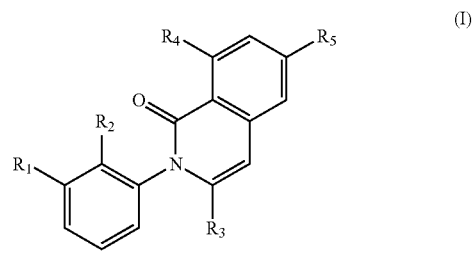
wherein $R_1$ is chosen from
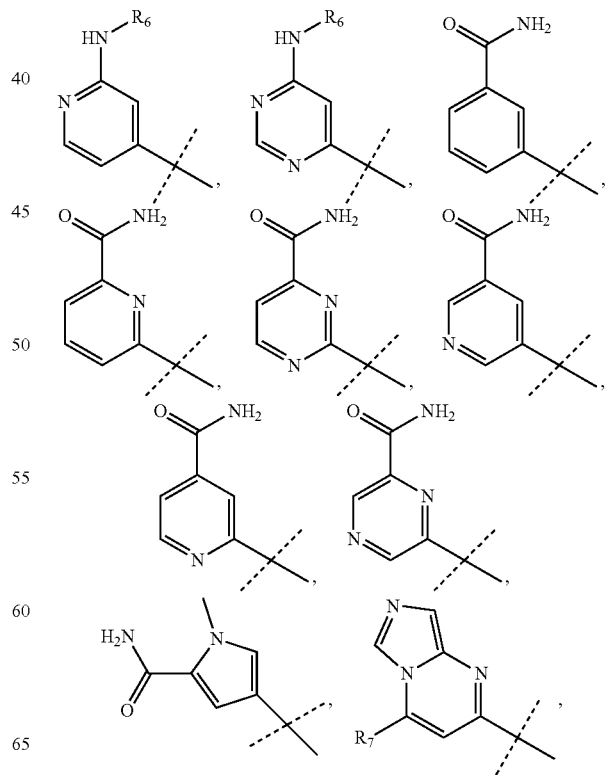

115
-continued

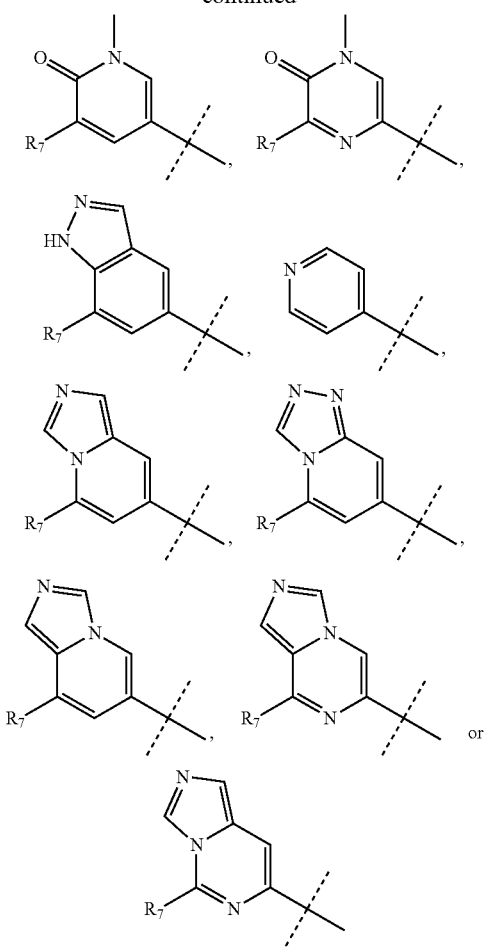

wherein R<sub>6</sub> is H or CH<sub>3</sub> and;
R<sub>7</sub> is H, NH<sub>2</sub>, —NH—C<sub>1-4</sub> alkyl or —NH—C<sub>3-4</sub> cycloalkyl
R<sub>2</sub> is chosen from H, F, Cl, CH<sub>3</sub>, or CH<sub>2</sub>OH;
R<sub>3</sub> is chosen from;

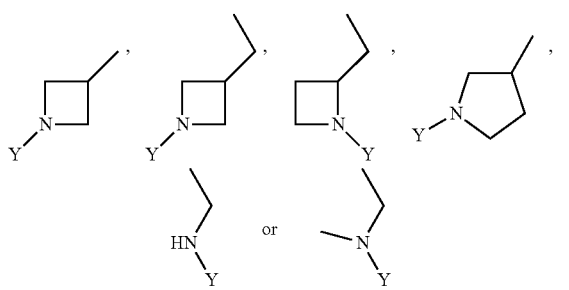

wherein Y is CN,

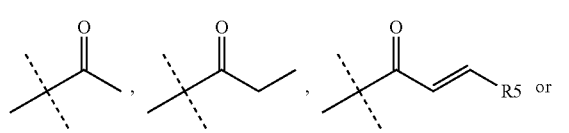

116
-continued

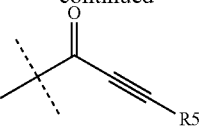

$R_4$ is chosen from H, F, Cl or OMe
each $R_5$ is independently chosen from H, $C_{1-4}$ alkyl, or $C_{3-4}$ cycloalkyl;
each group defined above for $R_1$-$R_5$ is, where possible, partially or fully halogentated; or a pharmaceutically acceptable salt thereof.

8. The compound of the formula (I) according to claim 7, wherein $R_1$ is chosen from

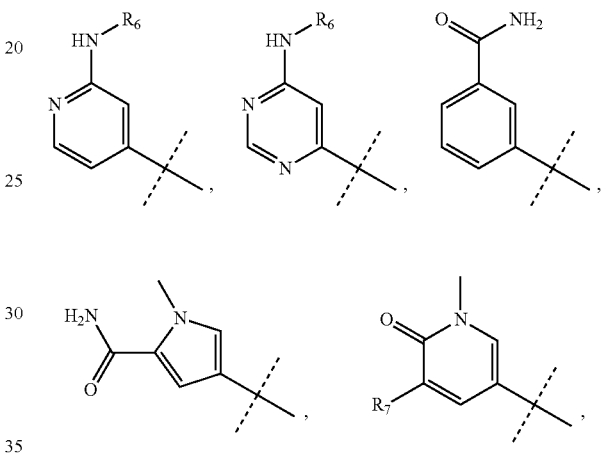

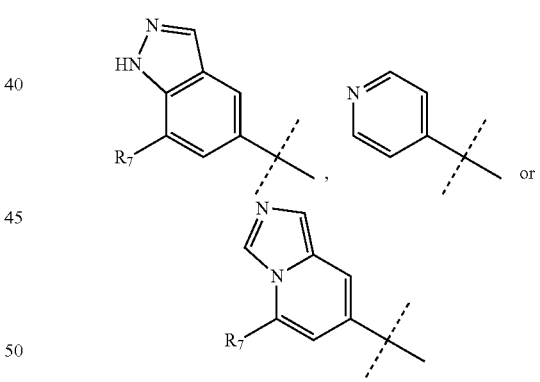

wherein $R_6$ is H or CH<sub>3</sub> and;
$R_7$ is H, NH<sub>2</sub>, —NH—C<sub>1-4</sub> alkyl or —NH—C<sub>3-4</sub> cycloalkyl, or —NH-Heterocycle
$R_2$ is chosen from H, F, Cl, CH<sub>3</sub>, or CH<sub>2</sub>OH;
$R_3$ is chosen from;

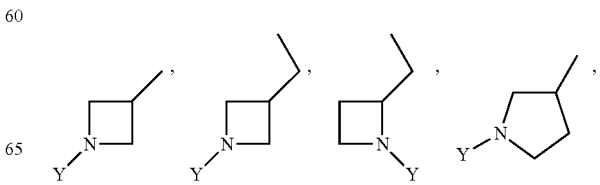

-continued

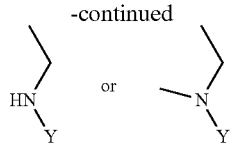

wherein Y is CN,

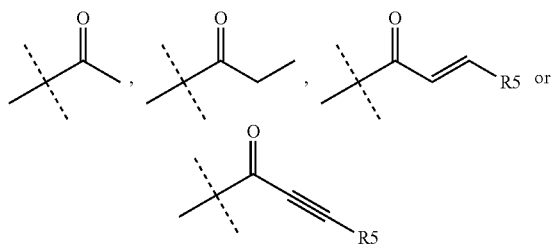

R$_4$ is chosen from H, F, Cl or OMe each R$_5$ is independently chosen from H, C$_{1-4}$ alkyl, or C$_{3-4}$ cycloalkyl;

each group defined above for R$_1$-R$_5$ is, where possible, partially or fully halogentated; or a pharmaceutically acceptable salt thereof.

9. The compound of the formula (I) according to claim 7, wherein R$_1$ is chosen from

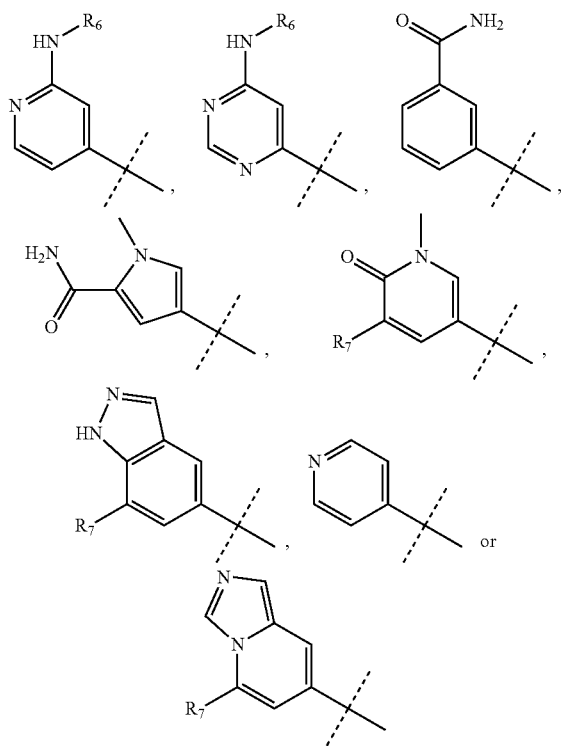

wherein R$_6$ is H or CH$_3$ and;
R$_7$ is H or NH$_2$
R$_2$ is chosen from H, F, Cl, CH$_3$ or CH$_2$OH;
R$_3$ is chosen from;

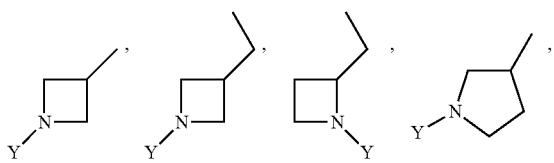

-continued

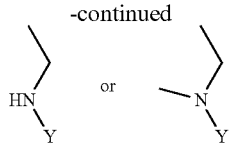

Wherein Y is CN,

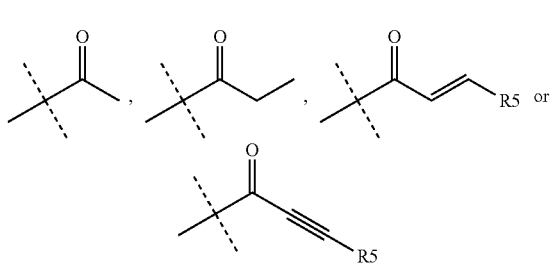

R$_4$ is chosen from H, F, Cl or OMe each R$_5$ is independently chosen from H, C$_{1-4}$ alkyl, or C$_{3-4}$ cycloalkyl;

each group defined above for R$_1$-R$_5$ is, where possible, partially or fully halogentated; or a pharmaceutically acceptable salt thereof.

10. The compound of the formula (I) according to claim 7, wherein R$_1$ is chosen from

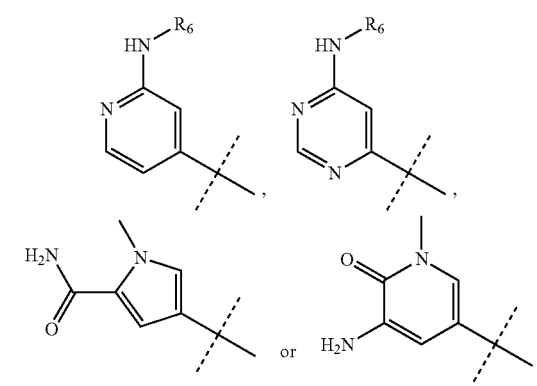

wherein R$_6$ is H or CH$_3$ and;
R$_2$ is CH$_2$OH;
R$_3$ is chosen from;

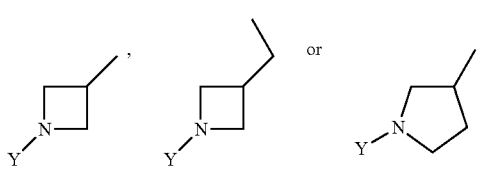

wherein Y is

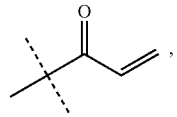

R₄ is chosen from H or F
each R₅ is independently chosen from H, C₁₋₄ alkyl, or C₃₋₄ cycloalkyl;
each group defined above for R₁-R₅ is, where possible, partially or fully halogentated; or a pharmaceutically acceptable salt thereof.
11. A compound chosen from any of the compounds shown in the following table:
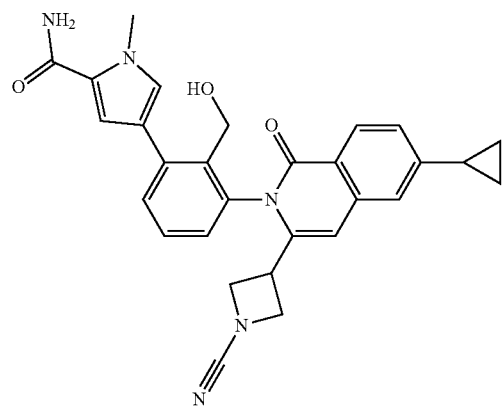
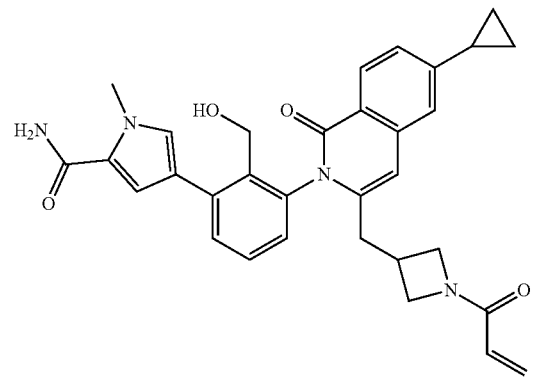
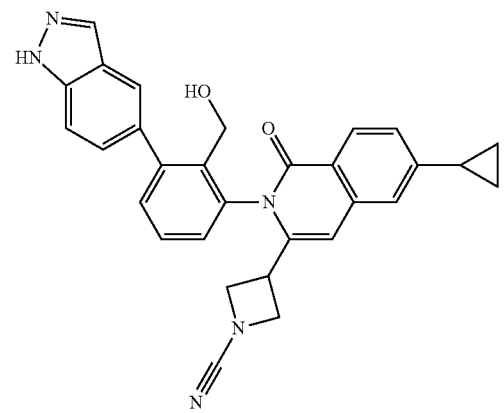
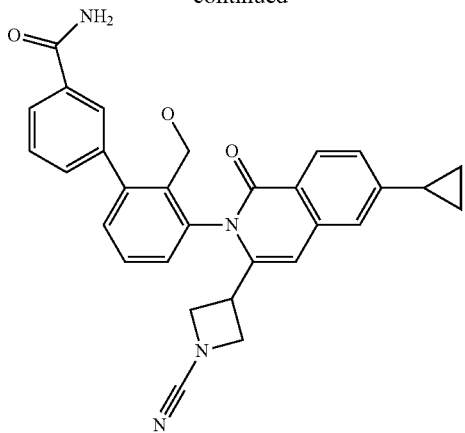
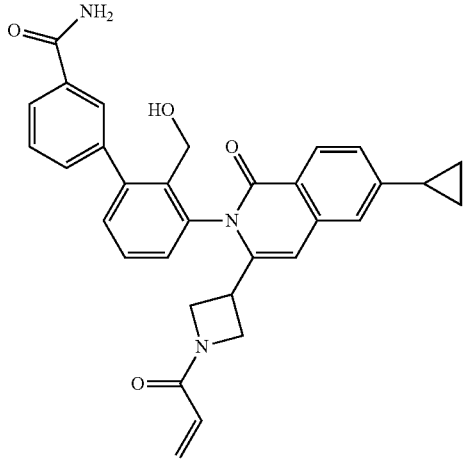
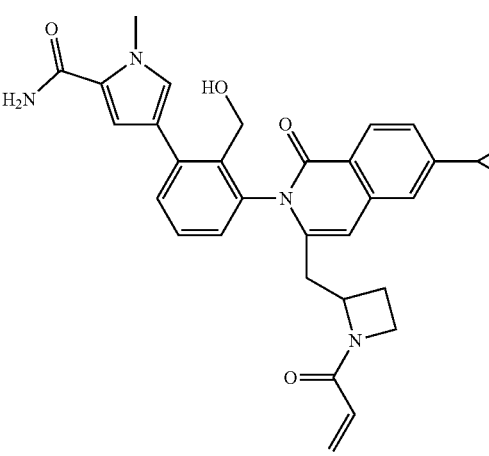

121
-continued
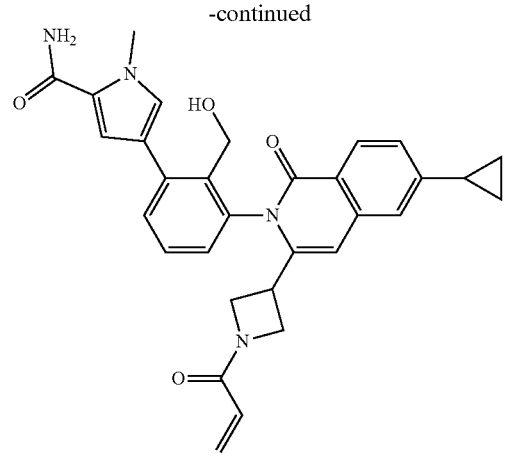
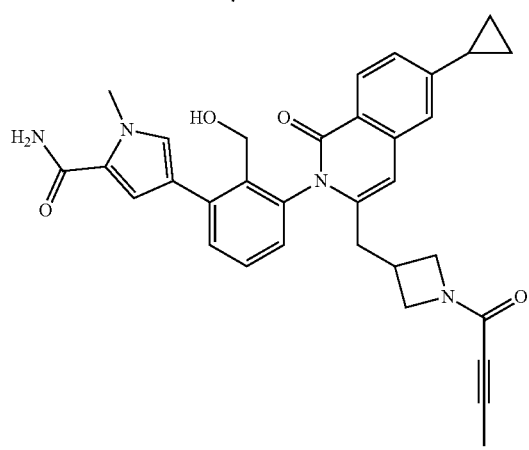
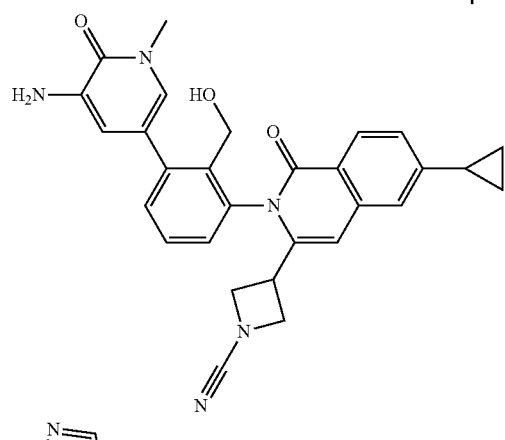
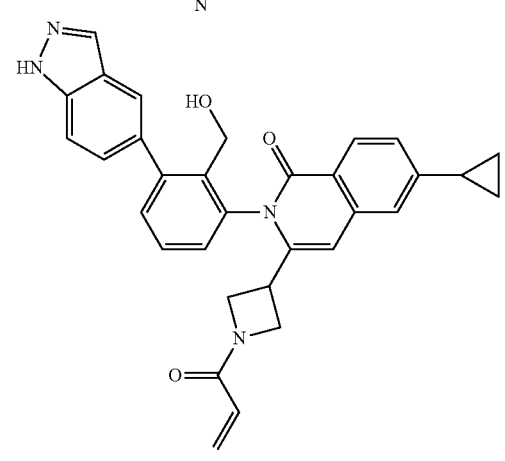
122
-continued
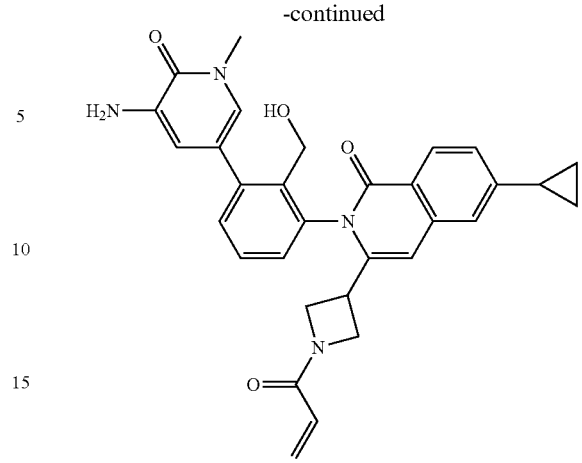
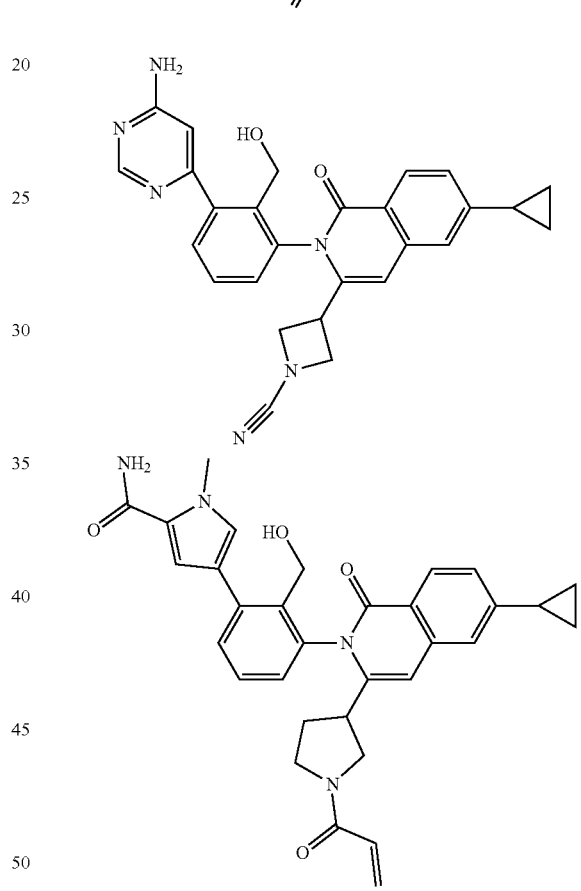
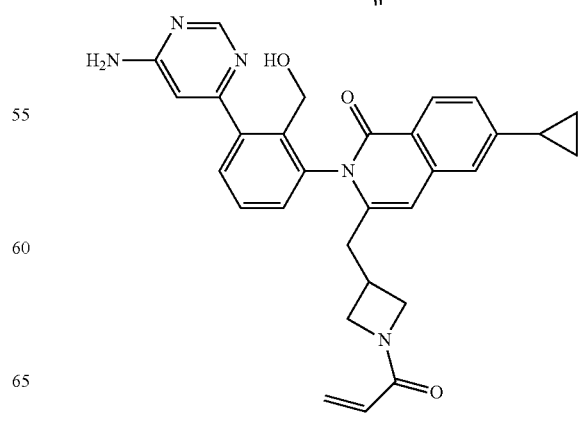

123
-continued
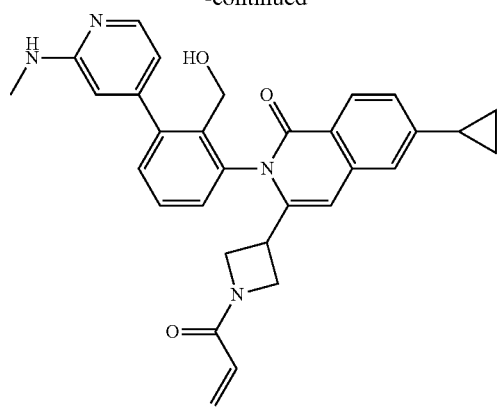
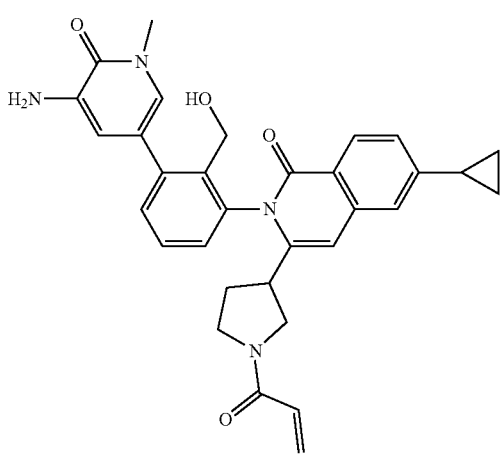
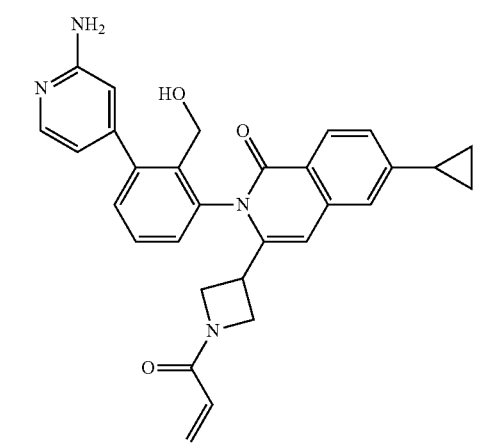
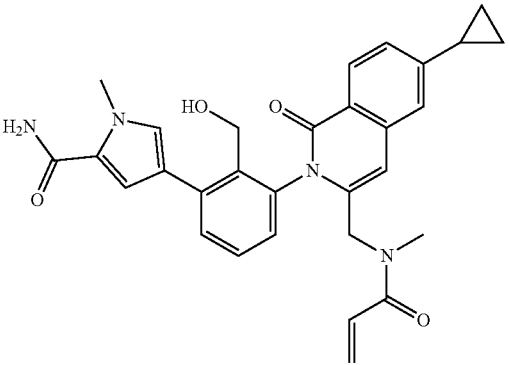
124
-continued
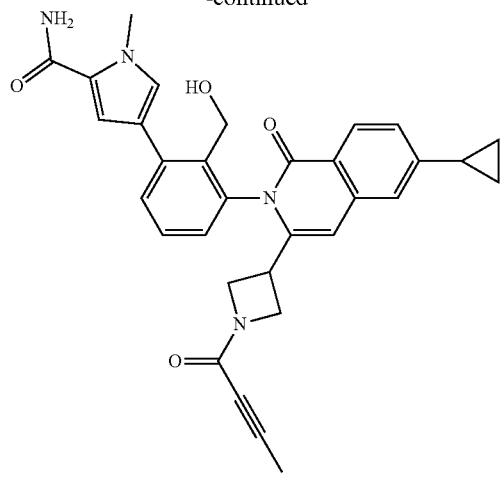
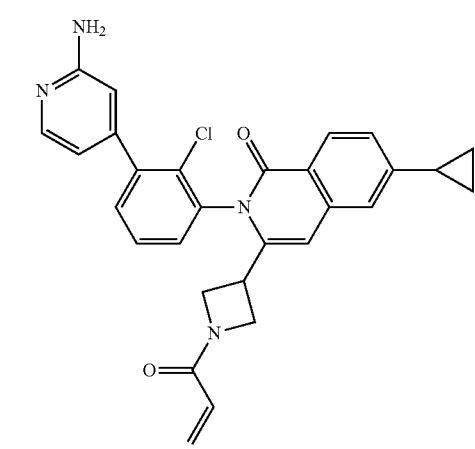
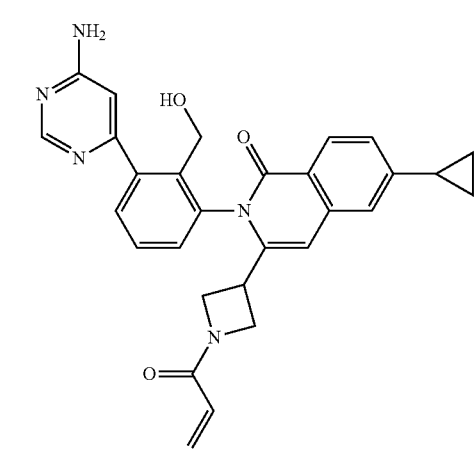

125
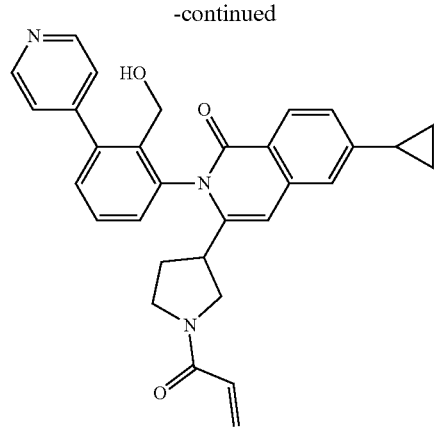
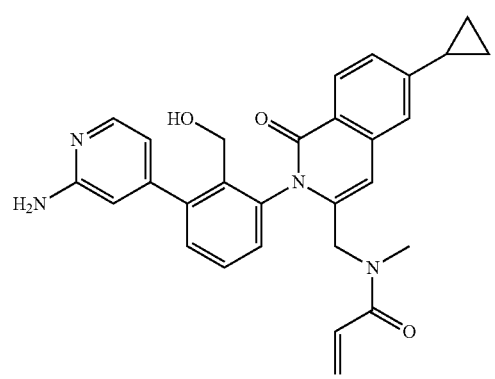
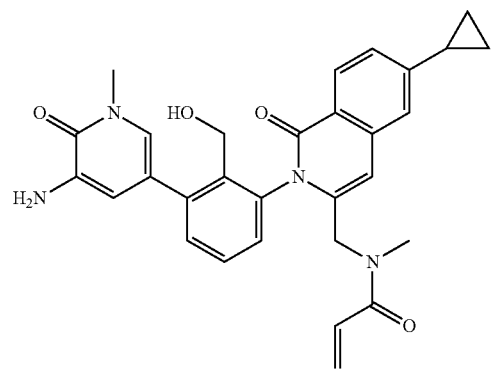
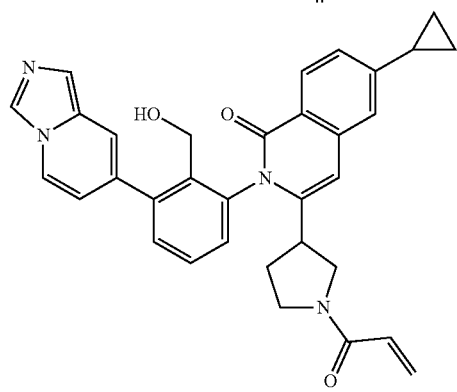
126
-continued
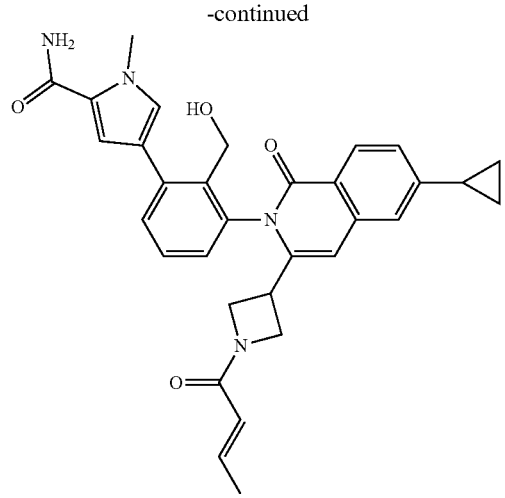
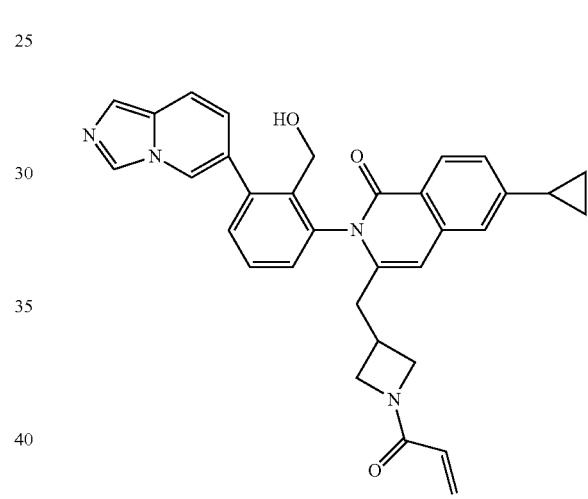
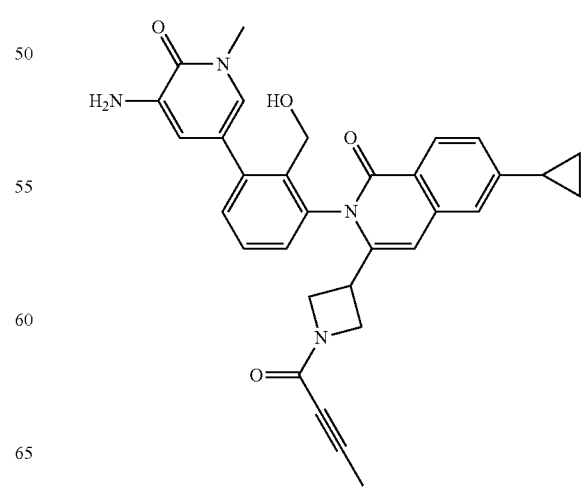

127
-continued
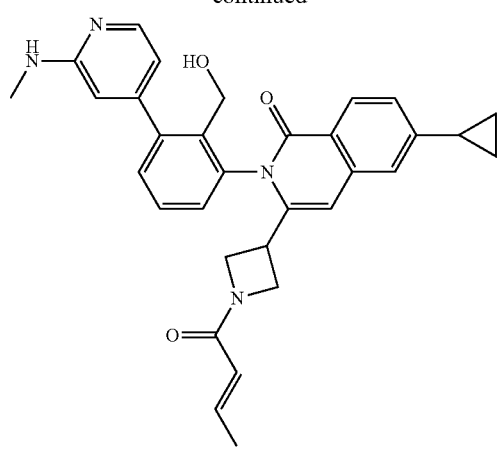
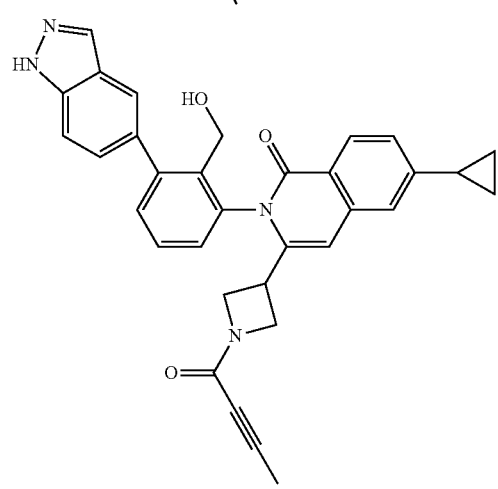
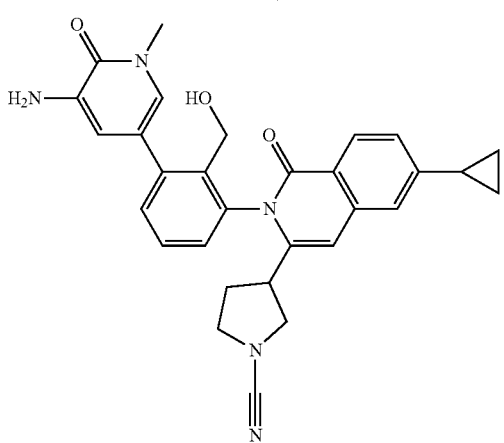
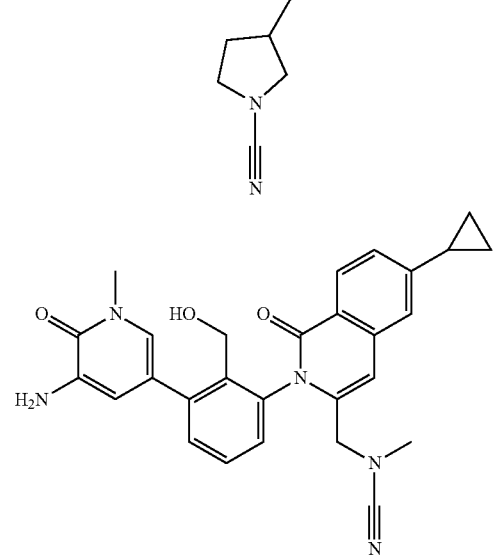
128
-continued
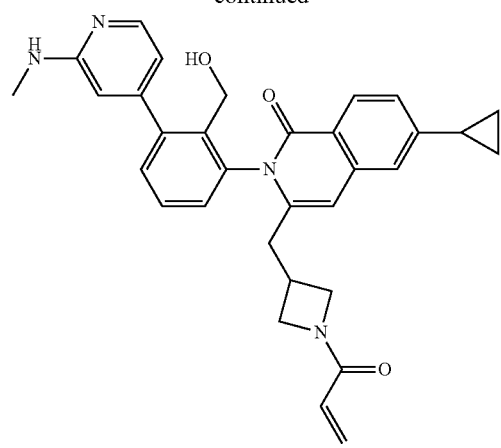
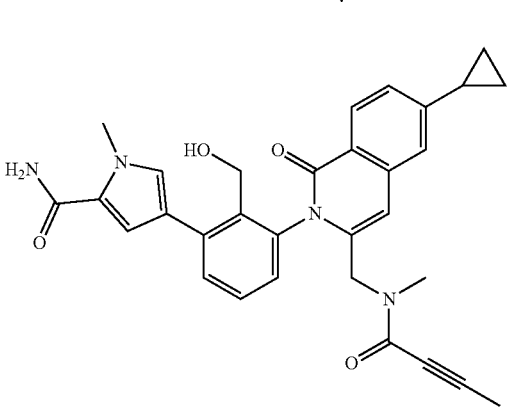
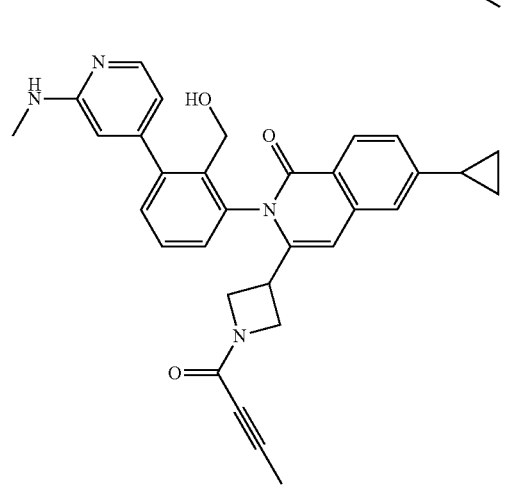
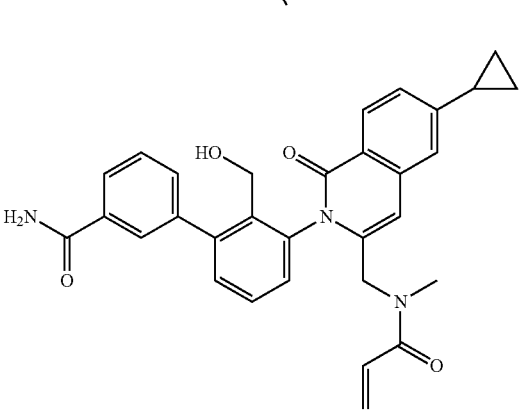

129
-continued
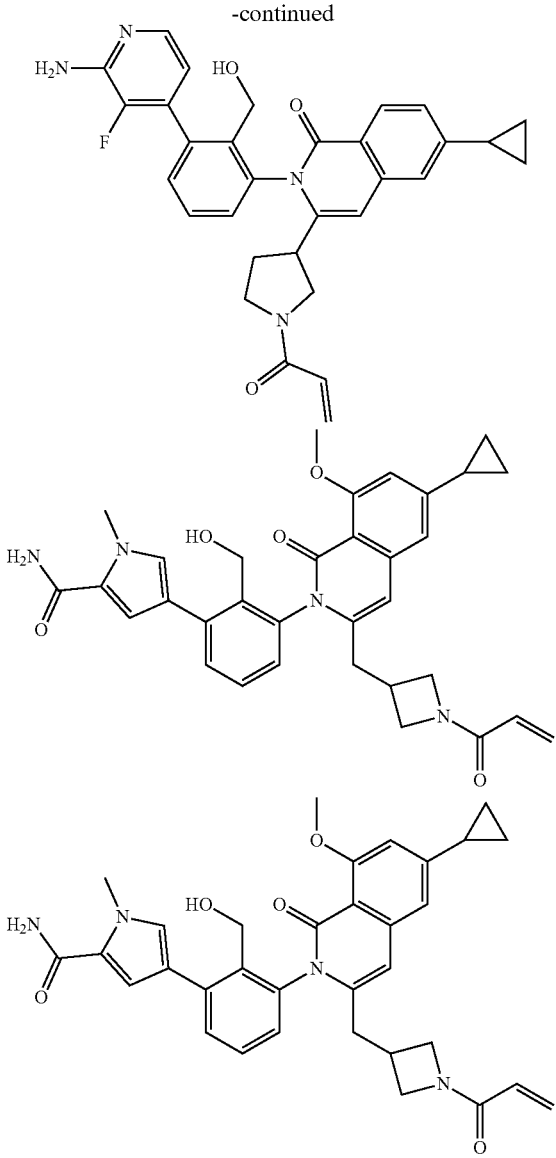
130
-continued
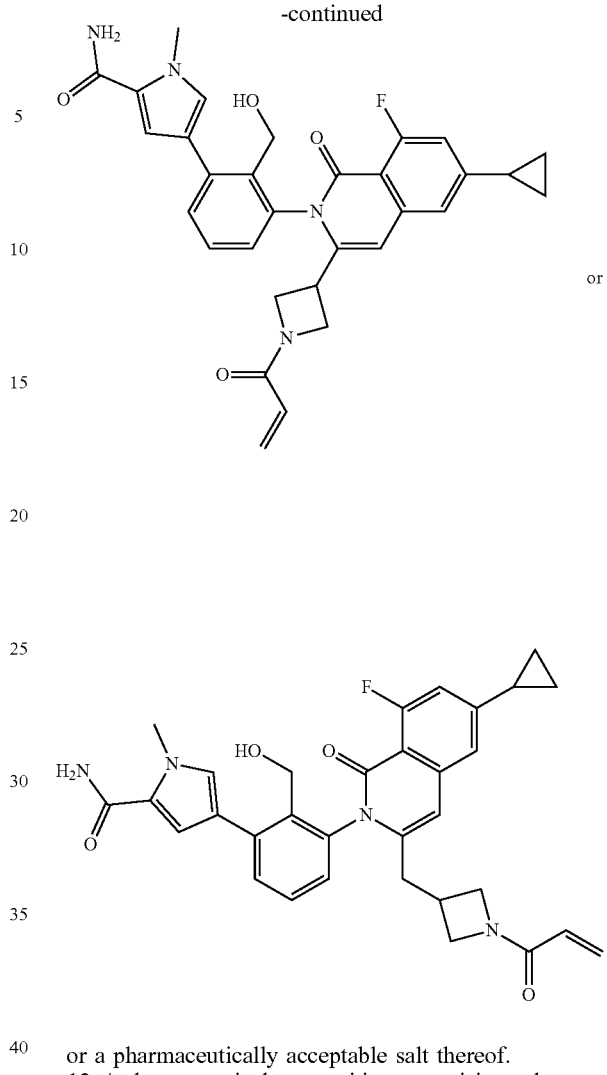
or a pharmaceutically acceptable salt thereof.
12. A pharmaceutical composition comprising a therapeutically effective amount of a compound according to claim 7 or a pharmaceutically acceptable salt thereof.
* * * * *